United States Patent [19]

Yeung et al.

[11] Patent Number: 5,695,626
[45] Date of Patent: Dec. 9, 1997

[54] CAPILLARIES FOR USE IN A MULTIPLEXED CAPILLARY ELECTROPHORESIS SYSTEM

[75] Inventors: Edward S. Yeung, Ames, Iowa; Huan-Tsang Chang, Silver Spring, Md.; Eliza N. Fung, Ames, Iowa

[73] Assignee: Iowa State University Research Foundation, Ames, Iowa

[21] Appl. No.: 667,950

[22] Filed: Jun. 18, 1996

Related U.S. Application Data

[62] Division of Ser. No. 444,565, May 19, 1995, Pat. No. 5,582,705.

[51] Int. Cl.⁶ .................. G01N 27/26; G01N 27/447
[52] U.S. Cl. .................. 204/605; 204/451; 204/455; 204/601
[58] Field of Search .................. 204/451, 452, 204/453, 454, 456, 601, 602, 603, 604, 605

[56] References Cited

U.S. PATENT DOCUMENTS

| | | | |
|---|---|---|---|
| 4,675,300 | 6/1987 | Zare et al. | 436/172 |
| 4,729,947 | 3/1988 | Middendorf et al. | 435/6 |
| 4,811,218 | 3/1989 | Hunkapiller et al. | 364/413.01 |
| 4,855,225 | 8/1989 | Fung et al. | 435/6 |
| 4,891,120 | 1/1990 | Sethi et al. | 204/299 |
| 4,927,265 | 5/1990 | Brownlee | 356/73 |
| 5,006,210 | 4/1991 | Yeung et al. | 204/180.1 |
| 5,021,646 | 6/1991 | Weinberger et al. | 250/227.11 |
| 5,089,111 | 2/1992 | Zhu et al. | 204/451 |
| 5,114,551 | 5/1992 | Hjerten et al. | 204/180.1 |
| 5,139,630 | 8/1992 | Chen | 204/180.1 |
| 5,141,609 | 8/1992 | Sweedler et al. | 204/452 |
| 5,164,055 | 11/1992 | Dubrow | 204/605 X |
| 5,171,534 | 12/1992 | Smith et al. | 422/82.05 |
| 5,188,934 | 2/1993 | Menchen et al. | 435/6 |
| 5,235,409 | 8/1993 | Burgi et al. | 204/45 X |
| 5,258,538 | 11/1993 | Fung et al. | 558/81 |
| 5,264,101 | 11/1993 | Demorest et al. | 204/299 R |
| 5,273,638 | 12/1993 | Konrad et al. | 204/299 R |
| 5,274,240 | 12/1993 | Mathies et al. | 250/458.1 |
| 5,277,780 | 1/1994 | Kambara | 204/603 |
| 5,312,535 | 5/1994 | Waska et al. | 204/603 |
| 5,324,401 | 6/1994 | Yeung et al. | 204/180.1 |
| 5,366,608 | 11/1994 | Kambara | 204/603 |
| 5,366,860 | 11/1994 | Bergot et al. | 435/6 |
| 5,366,877 | 11/1994 | Keith | 435/91.2 |
| 5,374,527 | 12/1994 | Grossman | 435/6 |
| 5,395,502 | 3/1995 | Pawliszyn | 204/299 R |
| 5,399,317 | 3/1995 | Stolowitz | 422/99 |
| 5,403,451 | 4/1995 | Riviello et al. | 204/153.1 |
| 5,439,578 | 8/1995 | Dovichi et al. | 204/603 |

FOREIGN PATENT DOCUMENTS

| | | |
|---|---|---|
| 350 194 A2 | 7/1988 | European Pat. Off. . |
| 294 996 A2 | 12/1988 | European Pat. Off. . |
| 523 982 A1 | 1/1993 | European Pat. Off. . |
| 4139211 | 6/1992 | Germany ............ 204/612 |
| 5-93711 | 4/1993 | Japan ............... 204/601 |
| WO 93/05389 | 3/1993 | WIPO . |
| WO 93/15395 | 8/1993 | WIPO . |
| WO 94/18552 | 8/1994 | WIPO .......... G01N 27/26 |

OTHER PUBLICATIONS

András Guttman et al, "Influence of Temperature on the Sieving Effect of Different Polymer Matrices in Capillary SDS Gel Electrophoresis of Proteins" Analytical Chemistry, vol. 65, No. 3 (Feb. 1993) 199–203.

András Guttman, "On the Separation Mechanism of Capillary Sodium Dodecyl Sulfate–gel Electrophoresis of Proteins", Electrophoresis, vol. 16, No. 4 (1995) 611–616 No month available.

András Guttman et al, "Effect of Operational Variables on the Separation of Proteins by Capillary Sodium Dodecyl Sulfate–gel Electrophoresis" Electrophoresis, vol. 15 (1994) 221–224 No month available.

S. Carson et al., "DNA Sequencing by Capillary Electrophoresis: Use of a Two–Laser–Two–Window Intensified Diode Array Detection System", Anal. Chem., 65, 3219–3226 (Nov. 15, 1993).

H.–T. Chang, "Development of novel separation techniques for biological samples in capillary electrophoresis", Abstract of Ph.D. Thesis obtained from Dialog Dissertation Abstracts Online database, Order No. AAD95–03536 No date available.

H.–T. Chang, "Development of novel separation techniques for biological samples in capillary electrophoresis", Ph.D. Thesis, Iowa State University, 1994 No month available.

D. Chen et al., "Two–label peak–height encoded DNA sequencing by capillary gel electrophoresis: three examples", Nucl. Acids Res., 20, 4873–4880 (1992) No month available.

G.M. Church et al., "Multiplex DNA Sequencing," Science, 240, 185–188 (Apr. 8, 1988).

A.S. Cohen et al., "Rapid separation and purification of oligonucleotides by high–performance capillary gel electrophoresis," Proc. Natl. Acad. Sci., U.S.A., 85, 9660–9663 (Dec. 1988).

P.M. Epperson et al., "Applications of Charge Transfer Devices in Spectroscopy", Anal. Chem., 60, 327A–335A (Mar. 1, 1988).

(List continued on next page.)

Primary Examiner—Kathryn L. Gorgos
Assistant Examiner—John S. Starsiak, Jr.
Attorney, Agent, or Firm—Mueting, Raasch, Gebhardt & Schwappach, P.A.

[57] ABSTRACT

The invention provides a side-entry optical excitation geometry for use in a multiplexed capillary electrophoresis system. A charge-injection device is optically coupled to capillaries in the array such that the interior of a capillary is imaged onto only one pixel. In Sanger-type 4-label DNA sequencing reactions, nucleotide identification ("base calling") is improved by using two long-pass filters to split fluorescence emission into two emission channels. A binary poly(ethyleneoxide) matrix is used in the electrophoretic separations.

20 Claims, 17 Drawing Sheets

OTHER PUBLICATIONS

D.N. Heiger et al., "Separation of DNA restriction fragments by high performance capillary electrophoresis with low and zero crosslinked polyacrylamide using continuous and pulsed electric fields", *J. Chromatogr.*, 516, 33–48 (1990) No month available.

S. Hjerten, "High–Performance Electrophoresis Elimination of Electroendosmosis and Solute Adsorption", *J. Chromatogr.*, 347, 191–198 (1985) No month available.

X.C. Huang et al., "Capillary Array Electrophoresis Using Laser–Excited Confocal Fluorescence Detection", *Anal. Chem.*, 64, 967–972 (Apr. 15, 1992).

X.C. Huang et al., "DNA Sequencing Using Capillary Array Electrophoresis", *Anal. Chem.*, 64, 2149–2154 (Sep. 15, 1992).

A.E. Karger et al., "Multiwavelength fluorescence detection for DNA sequencing using capillary electrophoresis", *Nucl. Acids Res.*, 19, 4955–4962 (1991) No month avaialble.

M.H. Kleemiss et al., "Capillary electrophoresis of DNA restriction fragments with solutions of entangled polymers", *Electrophoresis*, 14, 515–522 (1993) no month available.

L.B. Koutny et al., "Expert System for Data Acquisition to Achieve a Constant Signal–to–Noise Ratio: Application to Imaging of DNA Sequencing Gels", *Anal. Chem.*, 65, 148–152 (Jan. 15, 1993).

T.T. Lee et al., "Facilitating Data Transfer and Improving Precision in Capillary Zone Electrophoresis with Migration Indices", *Anal. Chem.*, 63, 2842–2848 (Dec. 15, 1991).

T.T. Lee et al., "Compensating for Instrumental and Sampling Biases Accompanying Electrokinetic Injection in Capillary Zone Electrophoresis," *Anal. Chem.*, 64, 1226–1231 (Jun. 1, 1992).

W.A. Mac Crehan et al., "Size–Selective Capillary Electrophoresis (SSCE) Separation of DNA Fragments", *J. Liq. Chromatogr.*, 15, 1063–1080 (1992) No month available.

R.A. Mathies et al., "New Directions in High–Sensitivity Fluorescence Detection of DNA and Capillary Array Electrophoresis", Abstract #133, DOE Human Genome Workshop IV, Santa Fe, NM, Nov. 13–17, 1994 No month avialable.

D.A. McGregor et al., "Interactive Control of Pulsed Field Gel Electrophoresis via RealTime Monitoring", *Anal. Chem.*, 64, 1–6 (Jan. 1, 1992).

D.A. McGregor et al., "Optimization of capillary electrophoretic separation of DNA fragments based on polymer filled capillaries", *J. Chromatogr.*, 652, 67–73 (1993) No month available.

R.E. Milofsky et al., "Native Fluorescence Detection of Nucleic Acids and DNA Restriction Fragments in Capillary Electrophoresis," *Anal. Chem.*, 65, 153–157 (Jan. 15, 1993).

S. Nathakarnkitkool et al., "High–resolution capillary electrophoretic analysis of DNA in free solution", *Electrophoresis*, 13, 18–31 (1992) No month avaialble.

J.M. Prober et al., "A System for Rapid DNA Sequencing with Fluorecent Chain–Terminating Dideoxynucleotides", *Science*, 238, 336–341 (Oct. 16, 1987).

M.A. Quesada et al., "High–Sensitivity DNA Detection with a Laser–Excited Confocal Fluorescence Gel Scanner," *Bio Techniques*, 10, 616–625 (1991) No month available.

M.C. Ruiz–Martinez et al., "DNA Sequencing by Capillary electrophoresis with Replaceable Linear Polyacrylamide and Laser–Induced Fluorescence Detection", *Anal. Chem.*, 65, 2851–2858 (Oct. 15, 1993).

F. Sanger et al., "DNA sequencing with chain–terminating inhibitors", *Proc. Natl. Acad. Sci. USA*, 74, 5463–5467 (Dec. 1977).

M. Starita–Geribaldi et al., "Lane distortions in gel electrophoresis patterns", *Electrophoresis*, 14, 773–781 (1993) No month available.

J.V. Sweedler et al, "High–Performance Charge Transfer Device Detectors," *Anal. Chem.*, 60, 282A–291A (Feb. 15, 1988).

J.V. Sweedler et al., "Fluorescence Detection in Capillary Zone Electrophoresis Using a Charge–Coupled Device with Time–Delayed Integration", *Anal. Chem.*, 63, 496–502 (Mar. 1, 1991).

H. Swerdlow et al., "Three DNA Sequencing Methods Using Capillary Gel Electrophoresis and Laser–Induced Fluorescence", *Anal. Chem.*, 63, 2835–2841 (Dec. 15, 1991).

H. Swerdlow et al., "Stability of capillary gels for automated sequencing of DNA", *Electrophoresis*, 13, 475–483 (1992) No month available.

S. Takahashi et al., "Installation of Multi–Capillary Electrophoresis," *Proceedings of Capillary Electrophoresis Symposium*, Dec. 1992 (with English–language Abstract).

S. Takahashi et al., "Multiple Sheath–Flow Gel Capillary–Array Electrophoresis for Multicolor Fluorescent DNA Detection", *Anal. Chem.*, 66, 1021–1026 (Apr. 1, 1994).

J.A. Taylor et al., "Axial–Beam Laser–Excited Fluorescence Detection in Capillary Electrophoresis," *Anal. Chem.*, 64, 1741–1744 (Aug. 1, 1992).

J.A. Taylor et al., "Multiplexed Fluorescence Detector for Capillary Electrophoresis using Axial Optical Fiber Illumination", *Anal. Chem.*, 65, 956–960 (Apr. 1, 1993).

R. Tomisaki et al., "High–Speed DNA Sequencer Using Capillary Gel Electrophoresis with a Laser–Induced Four–Color Fluorescent DNA Detector", *Anal. Sci.*, 10, 817–820 (Oct. 1994).

G.L. Trainor, "DNA Sequencing, Automation, and the Human Genome," *Anal. Chem.*, 62, 418–426 (Mar. 1, 1990).

K. Ueno et al., "Simultaneous Monitoring of DNA Fragments Separated by Electrophoresis in a Multiplexed Array of 100 Capillaries", *Anal. Chem.*, 66, 1424–1431 (May 1, 1994).

H.M. Wenz, "Capillary electrophoresis as a technique to analyze sequence–induced anomalously migrating DNA fragments", *Nucleic Acids Res.*, 22, 4002–4008 (1994) No month available.

C.–W. Whang et al., "Temperature Programming in Capillary Zone Electrophoresis", *Anal. Chem.*, 64, 502–506 (Mar. 1, 1992).

E.S. Yeung, "Quantitation in Electrophoresis Based on Lasers", Abstract of Grant No. OHER–RPIS 4922 obtained from the Dialog On–Line database Federal Research in Progress No date available.

E.S. Yeung, "Genome", Abstract of Grant No. WPAS–93/CH–AMES/00 obtained from the Dialog On–Line database Federal Research in Progress No date available.

E.S. Yeung et al., "Laser Fluorometric Detection in Liquid Chromatography," *Anal. Chem.*, 52, 1465A–1481A (Nov. 1980).

E.S. Yeung et al., "Laser fluorescence detector for capillary electrophoresis", *J. Chromatogr.*, 608, 73–77 (1992) No month avaialble.

E.S. Yeung et al., "High Speed DNA Sequencing by Using Capillary Electrophoresis", *Pittcon '95 Abstracts,* Abstract No. 379, presented at the 1995 Pittsburgh Conference, New Orleans, Louisiana (Mar. 5–10, 1995).

T. Zewert et al., "Polyhydroxy and polyethyleneglycol (meth)acrylate polymers: Physical properties and general studies for their use as electrophoresis matrices", *Electrophoresis,* 13, 817–824 (1992) no month avialable.

X. Lu et al., "Optimization of Excitation and Detection Geometry for Multiplexed Capillary Array Electrophoresis of DNA Fragments", *Applied Spectroscopy,* 49, 605–609 (May 1995).

Y. Kurosu et al., "Fluorescence Detection with an Immersed Flow Cell in Capillary Electrophoresis", *J. High Resolution,* 14, 186–187 (Mar. 1991).

M. Albin et al., "Fluorescence Detection in Capillary Zone Electrophoresis: Evaluation of Derivatizing Reagents and Techniques", *Anal. Chem.,* 63, 417–422 (Mar. 1991).

Y. Baba et al., "Gel–Filled capillaries for nucleic acid separations in capillary electrophoresis," *Trends in Anal. Chem.,* 11, 280–287 No month available.

J. Balch et al., "Sequencing of DNA by Gel Electrophoresis in Micromachined Channels", Abstract #134, DOE Human Genome Workshop IV, Santa Fe, NM, Nov. 13–17, 1994.

N. Best et al., "Separation of Fragments up to 570 Bases in Length by Use of 6% T Non–Cross–Linked Polyacrylamide for DNA Sequencing in Capillary Electrophoresis", *Anal. Chem.,* 66, 4063–4067 (Nov. 15, 1994).

CAPILLARIES FOR USE IN A MULTIPLEXED CAPILLARY ELECTROPHORESIS SYSTEM

This is a division of application Ser. No. 08/444,565, filed May 19,1995 now U.S. Pat. No. 5,582,705.

GOVERNMENT RIGHTS

This invention was made with government support under Contract No. W-7405-Eng-82 awarded by the U.S. Department of Energy. The Government has certain rights in this invention.

BACKGROUND OF THE INVENTION

The use of capillary electrophoresis (CE) has greatly improved DNA sequencing rates compared to conventional slab gel electrophoresis. Part of the improvement in speed, however, has been offset by the loss of the ability (inherent in slab gels) to accommodate multiple lanes in a single run. Highly multiplexed capillary electrophoresis, by making possible hundreds or even thousands of parallel sequencing runs, represents an attractive approach to overcoming the current throughput limitations of existing DNA sequencing instrumentation.

Excitation and Detection Geometry. Various excitation and detection systems have been developed to accommodate parallel arrays in capillary electrophoresis. Laser-induced fluorescence (LIF) detection has been the major method employed in the automation of DNA sequencing. The incident laser beam and the collected fluorescence light are typically perpendicular to each other in order to reduce background noise due to light scattering. On-column excitation and detection are generally performed from above the parallel array through transparent windows formed in the capillaries. For example, in one system a beam expander and a cylindrical lens are used to distribute the laser light into a thin line that intersects the axes of the capillaries, which are mounted in a grooved block so as to reduce cross-talk (K. Ueno et al., *Anal. Chem.*, 66, 1424 (1994)). Although a low detection limit and uniform distribution of excitation intensities can be achieved with this system, a long laser line compared to the array width has to be used due to the Gaussian intensity distribution. Thus, half of the laser light in the array region is wasted due to the longer laser line and the presence of the spacer grooves. Cross-talk, though manageable, is still in the range of 10% of the observed signal.

On-column detection has also been carried out using axial-beam laser-induced fluorescence detection by inserting optical fibers into an end of each separation capillary (J. A. Taylor et al., *Anal. Chem.*, 65, 956 (1993)). However, the intrusion of optical fibers into the separation capillaries affects the electroosmotic flow and increases the possibility for contamination and clogging. Furthermore, the detection limit is higher.

A type of side-entry excitation in a single capillary system has also been reported (R. N. Zare et al., U.S. Pat. No. 4,675,300 (1987)). In that system, an optical fiber is used to deliver coherent light to a translucent portion of a capillary, and fluorescence is detected through the translucent portion using a second optical fiber positioned perpendicular to the first optical fiber. This method suffers from excess stray light contamination and lower collimation efficiency.

Increased laser power is generally advantageous in providing a larger analyte signal. However, fluorophores are easily bleached, i.e., their fluorescing characteristic is destroyed by the laser beam, even at the milliwatt level, negating any increase in excitation intensity. Thus an LIF geometry that produces high resolution analyte signals while using a lower power laser (i.e., less than 50 mW) would represent a needed improvement in the art.

Detection Methods and Devices. Highly multiplexed CE imposes great demands on the detection system. For example, in one approach, a two-color confocal fluorescence scanner is employed for 25 capillaries (X. C. Huang et al., *Anal. Chem.*, 64, 967 (1992)). A mechanical stage is used to translate the capillary array across the optical region. Since data acquisition is sequential and not truly parallel, its use for hundreds of capillaries is limited. To be compatible with the high speed provided by CE and the high throughput of a large capillary array, a fast, sensitive, image array detector is required.

Recently, charge-coupled devices (CCDs) have been used as two-dimensional (n×m) image array detectors to pursue high-speed, high-throughput DNA sequencing. For example, a multiple sheath-flow apparatus and four-color detection system are used by S. Takahashi et al. (*Anal. Chem.*, 66, 1021 (1994)). Two laser beams are combined into one to cross the flow streams in an array of 20 capillaries in a line for excitation, and a CCD is used for simultaneous detection perpendicular to the excitation beam. Superior stray-light rejection can be achieved with this system. However, many challenges remain in scaling up from 20 to hundreds or thousands of capillaries. Misalignment of individual sheath flows, turbulence in the flow paths, improper matching of the laser beam waist over a long distance with the core diameters containing the eluted fragments, and the possible need to incorporate an extra space between the capillaries to accommodate the sheath flow are just a few of the problems associated with scale-up. Moreover, CCD detectors make major data analysis and storage demands on a system. CCDs read one array row at a time, and the time spent reading any particular row cannot be lengthened or shortened as desired in response to the amount of information in that row. A two-dimensional image array detection system that allowed random addressing and variable exposure times would significantly reduce data storage and analysis demands, and save considerable amounts of time as well.

Nucleotide Identification in DNA Sequencing Experiments—"Base Calling". It is unlikely that capillary electrophoresis will ever provide migration times that are reproducible enough among a group of capillaries to allow running four sets of fragments generated from a single DNA sample in a DNA sequencing analysis (one set of fragments for each for nucleotide bases A,T,C, and G) in separate capillaries. Thus, methods have been developed to distinguish the four bases run on a single capillary. The one-color, four-intensity scheme is least desirable because of difficulties in controlling the polymerase and maximizing the signal-to-noise ratio (S/N) (H. Swerdlow et al., *Anal. Chem.*, 63, 2835–2841 (1991)). The two-color, two-intensity scheme provides the advantages of a simpler optical arrangement, good light collection, and a straightforward algorithm (R. A. Mathies et al., *Anal. Chem.*, 64, 2149–2154 (1992); D. Chen et al., *Nucl. Acids Res.*, 20, 4873–4880 (1992)). However, like the one-color, four-intensity scheme, this scheme also assumes uniform incorporation of label by the polymerase which is often an incorrect assumption.

The technology in most common use is therefore still the four-color scheme originally reported by F. Sanger et al. (*Proc. Natl. Acad. Sci. U.S.A.*, 74, 5463–5467 (1977)). Many optical arrangements have been developed for base calling with four-dye labels (S. Carson et al., *Anal. Chem.*, 65, 3219–3226 (1993); R. Tomisaki et al., *Anal. Sci.*, 10, 817–820 (1994); A. E. Karger et al., *Nucl. Acids Res.*, 19, 4955–4962 (1991)). The four standard dyes (FAM and JOE, which are fluorescein derivatives, and ROX and TAMRA, which are rhodamine derivatives, available as the PRISM dyes from ABD division of Perkin Elmer, Foster City, Calif.) are by no means spectrally distinct, either in excitation or in emission. Currently available commercial instruments therefore use fairly narrow interference filters for emission and two laser wavelengths for excitation. Still, a complicated set of emmission ratios have to be employed for base calling. Monochromator-based spectral identification of the labels in principle offers the best selectivity. However, one needs to disperse the total fluorescence over many pixels to obtain a spectrum. This adds to the amount of raw data acquired and increases the acquisition time and the data work-up effort. Monochromators also do not have the favorable f-numbers for light collection that simple filters possess.

The so-called two-color sequencing scheme developed at DuPont is actually a four-label method (J. M. Prober et al., *Science*, 238, 336–341 (1987)). The optics are simplified and the ratio-based base calling algorithm is fairly straightforward. However, the four labels have emission bands that are very closely spaced. Even though the intensity ratios (used for base calling) are relatively independent of the incorporation rate of the polymerase reaction, spectral interference and a low S/N (low transmission of the bandpass filters) can lead to ambiguities. Thus, while there exist various proven base calling schemes, there is much room for improvement in terms of accuracy, speed and simplicity.

Sieving Medium. Further gains in sequencing rates should be possible by optimization of the sieving medium, which is also known as a separation medium, sieving matrix, or separation matrix. Crosslinked polymers such as polyacrylamide have been used as matrices in CGE because of their known utility in slab gels for the separation of proteins and DNA. However, due to the instability over time, irreproducibility in the polymerization processes, and the fragile nature of the medium, crosslinked polyacrylamide in CE has not been reported to last for more than a few runs, and is therefore not suitable for large-scale DNA sequencing, especially in multiplexed operation (H. Swerdlow et al., *Electrophoresis*, 13, 475–483 (1992)). Thus, alternative sieving matrices are needed.

Low- to moderate-viscosity entangled polymers have been used to overcome some of the above problems. Unlike crosslinked gels, they are more easily replaceable and more stable for use at higher temperatures and greater electric field strengths. Linear polyacrylamide (0% C, i.e., where the percentage of crosslinker is 0%) has been used for the size separation of DNA or proteins (D. N. Heiger et al., *J. Chromatogr.*, 516, 33–48 (1990); M. C. Ruiz-Martinez et al., *Anal. Chem.*, 65, 2851–2858 (1993). In addition, methyl cellulose (W. A. M. Crehan et al., *J. Liq. Chromatogr.*, 15, 1063–1080 (1992)), hydroxyalkyl cellulose (S. Nathakarn-kitkool et al., *Electrophoresis*, 13, 18–31 (1992)), polyhydroxy- and polyethyleneglycol-methacrylate (T. Zewert et al., *Electrophoresis*, 13, 817–824 (1993)), and polyvinylalcohol (M. H. Kleemiss et al., *Electrophoresis*, 14, 515–522 (1993)) also have been employed for DNA separations.

Several important problems remain before entangled polymers can be routinely used for large-scale DNA sequencing. Replacement of the sieving matrix after every run has not been as easy as expected. The high pressures found to be needed to effect complete matrix replacement (e.g., $1.25\times10^3$ pounds per square inch (psi). $6.46\times10^5$ torr) in M. C. Ruiz-Martinez et al., *Anal. Chem.* 65, 2851–2858 (1993)) may preclude the use of otherwise simple, automated schemes for flushing out a large number of capillaries in an array. In addition, the preparation of the linear polyacrylamide polymer solutions is difficult to control and to reproduce. The polymerization process depends critically on oxygen content, temperature, time for complete reaction, reagent purity and contamination. While one day the Human Genome Project may drive commercial manufacturers to produce "standard" polymer mixtures, at the present time only a 10% solution (700,000 to 1,000,000 $M_n$) and a solid (8,000,000 $M_n$) polyacrylamide product is available.

A separate but related problem is the internal coating of the capillary tubes. Typically, the fused-silica capillaries used in DNA sequencing by CE have been pretreated with a bonded coating. These are mostly variations of a bonded polyacrylamide layer. The reason for the coating is to reduce or eliminate the electroosmotic flow (EOF) that exists in bare fused-silica capillaries. EOF can actually expel the sieving matrix from the capillary. Even when EOF is low, the fact that it is opposite to the migration direction of DNA fragments means long separation times. Since the net motion is dictated by ($\mu_{DNA}-\mu_{EOF}$), representing the corresponding difference in mobilities ($\Delta\mu$), the large fragments are affected much more severely than the short fragments. Where EOF is present, variability in migration times makes it difficult to analyze samples containing larger DNA fragments. Unfortunately, the coating designed to reduce EOF degrades with use. This is not surprising since polyacrylamide, when used as the sieving medium, also breaks down with time on interaction with the typical buffers used for DNA sequencing. There is definitely a need for better surface treatment procedures for the capillary columns to retain their integrity over many runs.

SUMMARY OF THE INVENTION

The present invention provides a number of improved systems and methods for use in multiplexed capillary electrophoresis. A first embodiment of a multiplexed capillary electrophoresis system includes a capillary array of coplanar parallel capillaries, each capillary having an annular wall with a first transparent portion defining a transparent path extending through the capillary array perpendicular to the capillaries; and a coherent light source positioned to direct a beam of coherent light having a wavelength of about 200–1500 nm along the transparent path.

A second embodiment of a capillary electrophoresis system includes: (a) a capillary array having a plurality of coplanar parallel capillaries, each capillary having an annular wall defining an interior portion, each annular wall having a transparent portion for optically coupling the interior portion to an image array detector; and (b) an image array detector having linearly aligned pixels located in a plane parallel to the capillary array such that at least one of the capillaries is optically coupled to less than about six of the pixels.

A third embodiment of a capillary electrophoresis system provided by the present invention includes: (a) at least one capillary having an annular wall defining an interior portion containing a fluorescent target species; (b) a coherent light source positioned to direct a single beam of coherent light so as to contact the interior portion and induce fluorescence emission from the target species; (c) first and second long-pass filters positioned to split the fluorescence emission into first and second emission channels, respectively; and (d) a detector for simultaneously detecting the fluorescence emission in the first and second emission channels.

A fourth embodiment of a capillary electrophoresis system provided by the present invention includes at least one bare capillary having an uncoated bare fused silica wall comprising protonated silanol groups. A fifth embodiment of a capillary electrophoresis system includes at least one capillary containing a polymer matrix comprising about 0.5%–3% poly(ethyleneoxide) having $M_n$ of about 300,000–8,000,000. The present invention also provides a capillary containing a polymer matrix comprising about 0.5%–3% poly(ethyleneoxide) having $M_n$ of about 300,000–8,000,000.

The various methods provided by the present invention include a method for detecting fluorescent target species in a sample using multiplexed capillary electrophoresis. One such method includes the steps of: (a) providing a capillary array of coplanar parallel capillaries, each capillary having an intake end, an outflow end, and an annular wall with a first transparent portion defining a transparent path extending through the capillary array perpendicular to the capillaries; (b) introducing a sample containing a fluorescent target species into the intake end of at least one capillary such that the sample migrates through the capillary toward the outflow end; (c) inducing fluorescence emission from the target species by irradiating the species with a beam of coherent light having a wavelength of about 200–1500 nm directed along the transparent path; and (d) detecting fluorescence emission from the target species.

A second method for detecting fluorescent target species in a sample using capillary electrophoresis includes the steps of: (a) providing a capillary array having a plurality of coplanar parallel capillaries, each capillary having an intake end, an outflow end, and an annular wall, each annular wall defining an interior portion and having a transparent portion for optically coupling the interior portion to an image array detector; (b) optically coupling the capillary array to an image array detector having linearly aligned pixels located in a plane parallel to the capillary array such that at least one of the capillaries is optically coupled to less than about six of the pixels; (c) introducing a sample containing a fluorescent target species into the intake end of at least one of the capillaries such that the sample migrates through the capillary toward the outflow end; (d) inducing fluorescence emission from the target species by irradiating the species with a beam of coherent light having a wavelength of about 200–1500 nm; and (e) detecting the fluorescence emission through the transparent portion of the capillary using the optically coupled pixels.

A third method for detecting a target species in a sample using capillary electrophoresis includes the steps of: (a) providing at least one bare capillary having an intake end, an outflow end, and an uncoated fused silica internal wall comprising silanol groups; (b) contacting the bare capillary with acid for a time effective to protonate the silanol groups on the uncoated fused silica internal wall; (c) introducing a sample containing a target species into the intake end of at least one bare capillary such that the sample migrates through the capillary toward the outflow end; and (d) detecting the target species.

The present invention also provides a method for detecting a fluorescent DNA fragment in a sample using multiplexed capillary electrophoresis. One such method includes: (a) providing a capillary array of coplanar parallel capillaries, each capillary having an intake end, an outflow end, and an annular wall defining an interior portion, each annular wall having a transparent portion optically coupled to a detector; (b) introducing a sample containing a DNA fragment into the intake end of at least one capillary such that the sample migrates through the capillary toward the outflow end; (c) inducing fluorescence emission from the DNA fragment by irradiating the sample with a single beam of coherent light; (d) splitting the fluorescence emission into a first emission channel and a second emission channel using a first long-pass filter and a second long-pass filter, respectively; and (e) detecting fluorescence emission in the first and second emission channels, wherein detection is effected through the transparent portion of the annular wall.

A second method for detecting a fluorescent DNA fragment in a sample using multiplexed capillary electrophoresis includes the steps of: (a) providing a capillary array of coplanar parallel capillaries, each capillary having an intake end and an outflow end; (b) using pressure to inject a sample containing a DNA fragment into the intake end of at least one capillary such that the sample migrates through the capillary toward the outflow end; (c) inducing fluorescence emission from the DNA fragment by irradiating it with a beam of coherent light having a wavelength of about 200–1500 nm; and (d) detecting fluorescence emission from the DNA fragment.

DETAILED DESCRIPTION OF THE INVENTION

Figure 1:
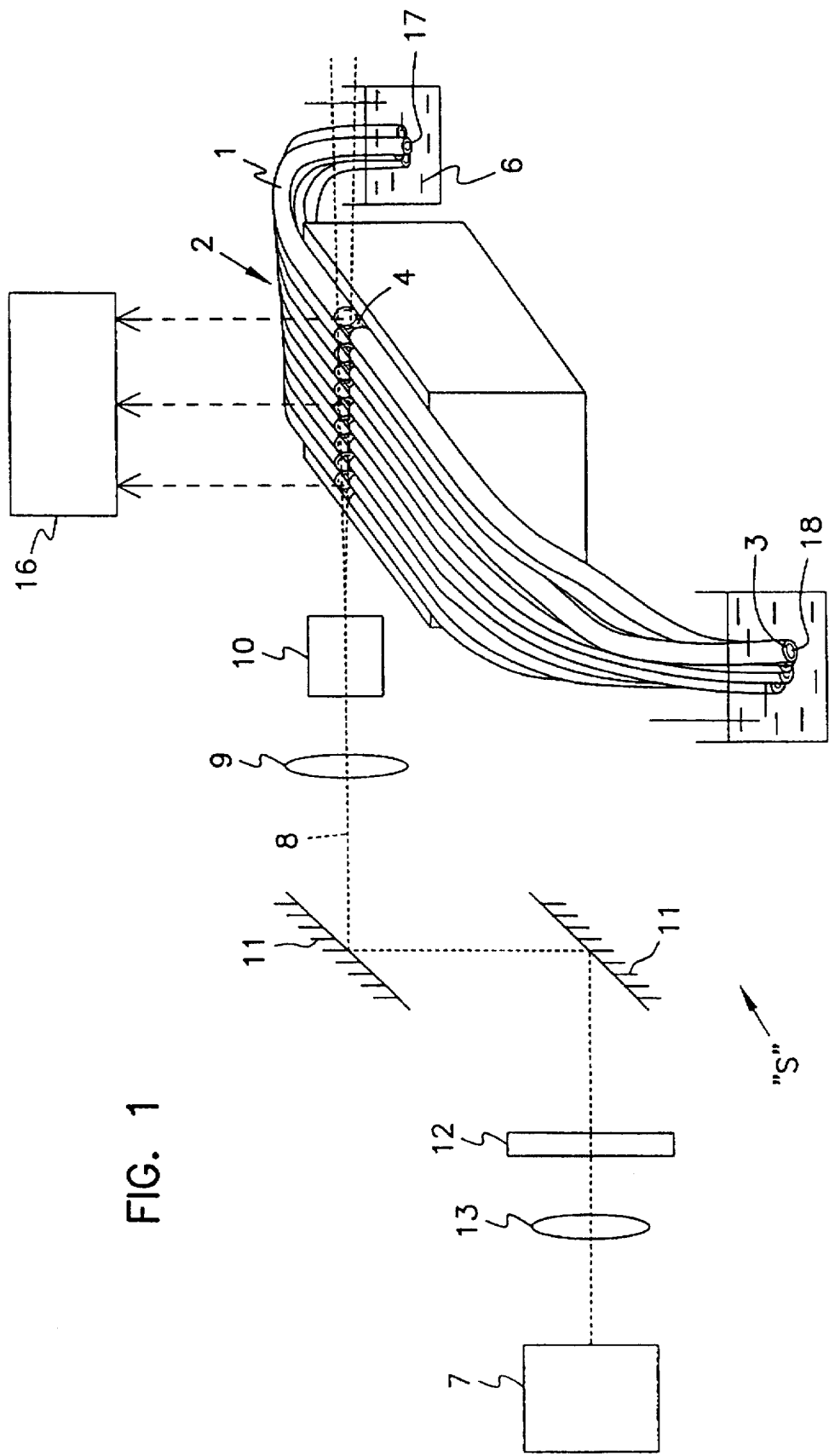
FIG. 1 is a schematic diagram of a side entry excitation geometry for a multiplexed capillary electrophoresis system.

The present invention utilizes an integrated approach toward achieving automation, high speed, high accuracy, and low cost in multiplexed capillary electrophoresis DNA sequencing. As used herein, multiplexed capillary electrophoresis refers to capillary electrophoresis systems containing at least about 10 capillaries. The various embodiments of the invention are particularly well-suited for use in capillary electrophoresis systems containing at least about 100 capillaries, up to and beyond thousands of capillaries. Aspects of the invention are directed to improvement of separation matrices, advances in excitation and detection geometry, an improved two-dimensional array detector, and novel base calling strategies.

In capillary electrophoresis, a buffer-filled capillary is suspended between two reservoirs filled with buffer. An electric field is applied across the two ends of the capillary. The electrical potential that generates the electric field is in the range of kilovolts. Samples containing one or more components or species are typically introduced at the high potential end and under the influence of the electrical field. Alternatively, the sample is injected using pressure or vacuum. The same sample can be introduced into many capillaries, or a different sample can be introduced into each capillary. Typically, an array of capillaries is held in a guide and the intake ends of the capillaries are dipped into vials that contain samples. After the samples are taken in by the capillaries, the ends of the capillaries are removed from the sample vials and submerged in a buffer which can be in a common container or in separate vials. The samples migrate toward the low potential end. During the migration, components of the sample are electrophoretically separated. After separation, the components are detected by a detector. Detection may be effected while the samples are still in the capillaries or after they have exited the capillaries.

The channel length for capillary electrophoresis is selected such that it is effective for achieving proper separation of species. Generally, the longer the channel, the greater the time a sample will take in migrating through the capillary. Thus, the species may be separated from one another with greater distances. However, longer channels contribute to the band broadening and lead to excessive separation time. Generally, for capillary electrophoresis, the capillaries are about 10 cm to about 5 meters long, and preferably about 20 cm to about 200 cm long. In capillary gel electrophoresis, where typically a polymer separation matrix is used, the more preferred channel length is about 10 cm to about 100 cm long.

The internal diameter (i.e., bore size) of the capillaries is not critical, although small bore capillaries are more useful in highly multiplexed applications. The invention extends to a wide range of capillary sizes. In general, capillaries can range from about 5–300 micrometers in internal diameter, with about 20–100 micrometers preferred. The length of the capillary can generally range from about 100–3000 mm, with about 300–1000 mm preferred.

The use of machined channels instead of capillaries has recently been reported (R. A. Mathies et al., Abstract #133, DOE Human Genome Workshop IV, Santa Fe, N. Mex., Nov. 13–17, 1994; J. Balch et al., Abstract #134, DOE Human Genome Workshop IV, Santa Fe, N. Mex., Nov. 13–17, 1994). With conventional technology, however, multiple capillaries are still the more developed format for multiplexed CE runs. However, technologies developed for capillaries, such as those disclosed herein, are readily transferable to machined channels when that technology becomes more developed.

A suitable capillary is constructed of material that is sturdy and durable so that it can maintain its physical integrity through repeated use under normal conditions for capillary electrophoresis. It is typically constructed of non-conductive material so that high voltages can be applied across the capillary without generating excessive heat. Inorganic materials such as quartz, glass, fused silica, and organic materials such as polytetrafluoroethylene, fluorinated ethylene/propylene polymers, polyfluoroethylene, aramide, nylon (i.e., polyamide), polyvinyl chloride, polyvinyl fluoride, polystyrene, polyethylene and the like can be advantageously used to make capillaries.

Where excitation and/or detection are effected through the capillary wall, a particularly advantageous capillary is one that is constructed of transparent material, as described in more detail below. A transparent capillary that exhibits substantially no fluorescence, i.e., that exhibits fluorescence lower than background level, when exposed to the light used to irradiate a target species is especially useful in cases where excitation is effected through the capillary wall. Such a capillary is available from Polymicro Technologies (Phoenix, Ariz.). Alternatively, a transparent, non-fluorescing portion can be formed in the wall of an otherwise nontransparent or fluorescing capillary so as to enable excitation and/or detection to be carried out through the capillary wall. For example, fused silica capillaries are generally supplied with a polyimide coating on the outer capillary surface to enhance its resistance to breakage. This coating is known to emit a broad fluorescence when exposed to wavelengths of light under 600 nm. If a through-the-wall excitation scheme is used without first removing this coating, the fluorescence background can mask a weak analyte signal. Thus, a portion of the fluorescing polymer coating can be removed by any convenient method, for example, by boiling in sulfuric acid, by oxidation using a heated probe such as an electrified wire, or by scraping with a knife. In a capillary of approximately 0.1 mm inner diameter or less, a useful transparent portion is about 0.01 mm to about 1.0 mm in width.

In electrophoresis, the separation buffer is typically selected so that it aids in the solubilization or suspension of the species that are present in the sample. Typically the liquid is an electrolyte which contains both anionic and cationic species. Preferably the electrolyte contains about 0.005–10 moles per liter of ionic species, more preferably about 0.01–0.5 mole per liter of ionic species. Examples of an electrolyte for a typical electrophoresis system include mixtures of water with organic solvents and salts. Representative materials that can be mixed with water to produce appropriate electrolytes includes inorganic salts such as phosphates, bicarbonates and borates; organic acids such as acetic acids, propionic acids, citric acids, chloroacetic acids and their corresponding salts and the like; alkyl amines such as methyl amines; alcohols such as ethanol, methanol, and propanol; polyols such as alkane diols; nitrogen containing solvents such as acetonitrile, pyridine, and the like; ketones such as acetone and methyl ethyl ketone; and alkyl amides such as dimethyl formamide, N-methyl and N-ethyl formamide, and the like. The above ionic and electrolyte species are given for illustrative purposes only. A researcher skilled in the art is able to formulate electrolytes from the above-mentioned species and optionally species such an amino acids, salts, alkalis, etc., to produce suitable support electrolytes for using capillary electrophoresis systems.

The voltage used for electrophoretic separations is not critical to the invention, and may very widely. Typical voltages are about 500 V–30,000 V, preferably about 1,000–20,000 V.

Electrophoretic separation can be conducted with or without using a molecular matrix (also referred to herein as a sieving matrix or medium as well as a separation matrix or medium) to effect separation. Where no matrix is used, the technique is commonly termed capillary zone electrophoresis (CZE). Where a matrix is used, the technique is commonly termed capillary gel electrophoresis (CGE). A preferred separation matrix of the invention for use in CGE is a linear polymer solution, such as a poly(ethyleneoxide) solution. However, other separation matrices commonly used in capillary electrophoresis, such as cross-linked polyacrylamide, can also be used in various aspects of the invention. Suitable matrices can be in the form of liquid, gel, or granules.

The present invention may be used for the separation, detection and measurement of the species present in samples of biological, ecological, or chemical interest. Of particular interest are macromolecules such as proteins, polypeptides, saccharities and polysaccharides, genetic materials such as nucleic acids, polynucleotides, carbohydrates, cellular materials such as bacteria, viruses, organelles, cell fragments, metabolites, drugs, and the like, and combinations thereof. Proteins that are of interest includplproteins that are present in blood plasma, which includes albumin, globulin, fibrinogen, blood clotting factors, hormones, and the like. Other interesting proteins that can be separated and detected using capillary electrophoresis systems are interferons, enzymes, growth factors, and the like. Other chemicals that can be separated and detected using the present invention include, but are not limited to pharmaceuticals such as antibiotics, as well as agricultural chemicals such as insecticides and herbicides.

Of particular interest are the group of macromolecules that are associated with the genetic materials of living organisms. These include nucleic acids and oligonucleotides such as RNA, DNA, their fragments and combinations, chromosomes, genes, as well as fragments and combinations thereof. The invention is especially suited to applications involving DNA diagnostics, such as DNA sequencing, DNA fragment analysis, and DNA fingerprinting. Sequence variations as small as one base or base pair difference between a sample and a control can be detected.

Excitation and Detection Geometry. It is important to understand what works best when single capillaries are used may not be transferable to a large-scale multiplexed capillary array. A case in point is the standard excitation/emission geometry for capillary electrophoresis based on tight focusing of the laser beam and efficient collimation by using microscope objectives with large numerical apertures. The Raleigh range of the tightly focused laser beam and the limited field-of-view of a microscope objective simply cannot be extended to monitor more than a few capillaries at a time.

Figure 2:
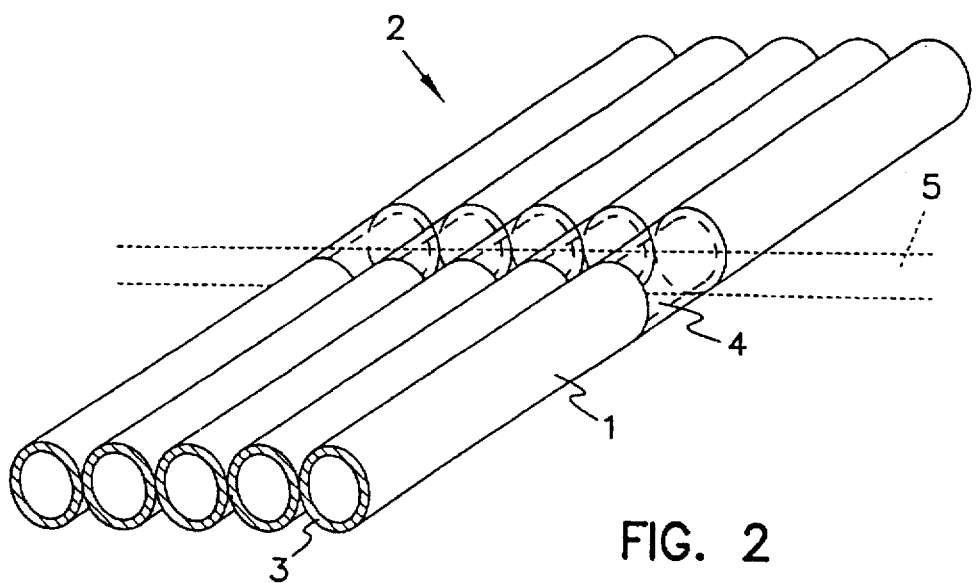
FIG. 2 shows a transparent portion of the annular wall of a capillary extending completely around the capillary.

The present invention provides a multiplexed capillary electrophoresis system "S" having a side-entry excitation geometry. The system is particularly well suited to fluorescence detection of a fluorescent target species in a sample, as will be described further below. FIGS. 1 and 2 show one embodiment of the invention. Capillaries 1 are arranged in a coplanar, parallel capillary array 2. Preferably, the capillary array 2 contains at least about 100 coplanar, parallel capillaries 1. The annular wall 3 of each capillary 1 has a first transparent portion 4. The transparent portion 4 is transparent to light having a wavelength about equal to a wavelength of a beam of coherent light used to irradiate a target species in a capillary, as is described in more detail below. A transparent medium is one that transmits light with substantially no attendant light scattering. Preferably, the transparent portion 4 is transparent to light having a wavelength of about 200–1500 nm, more preferably about 250–800 nm. In a preferred embodiment, the transparent portion 4 extends completely around the capillary, as shown in FIG. 1.

Together, the transparent portions 4 of the annular walls 3 define a transparent path 5 extending through the capillary array 2 perpendicular to the capillaries 1, as shown in FIG. 2. In a particularly preferred embodiment, the transparent path comprises a plane extending through the capillaries, as is the case where the capillaries are fabricated entirely out of transparent material.

Alternatively, each annular wall 3 can contain a translucent portion defining a translucent path extending through the array 2 perpendicular to the capillaries 1. A translucent medium produces some light scattering when transmitting light. Transparency is preferred over translucency because of greater light throughput and reduced detection S/N.

It is much easier to maintain a coplanar parallel configuration if the capillaries 1 are substantially adjacent to each other and mounted on a smooth surface, as shown in FIG. 1, than if they are physically separated from one another. As used herein, the term "substantially adjacent to each other" means that the coplanar parallel capillaries are closely packed in the array so as to be substantially contiguous along their parallel lengths, leaving essentially no space between adjacent capillaries. Substantially adjacent capillaries can be physically touching each other along all or a portion of their parallel lengths, although slight inconsistencies in capillary wall diameter or other features of the array can prevent them from being in contact along their entire coplanar parallel lengths. The capillary array can contain one or more subsets or subarrays of coplanar, parallel capillaries, with space in between the subsets or subarrays. Preferably, the capillaries in the subsets or subarrays are substantially adjacent to each other.

Intentional physical separation of capillaries using space or spacers has generally been required in other capillary geometries known in the art, since bringing the capillaries too close together can create excessive interference with fluorescence detection due to increased levels of cross-talk and scattered light. However, cross-talk and light scattering produced by the side-entry excitation geometry of the invention are sufficiently low to eliminate the need for space or spacers between the capillaries 1 as will be discussed below. Of course, the capillaries 1 may be separated if desired, as by being placed on a block having machined grooves or being separated by spacers, provided they remain parallel and in the same plane.

Light scattering and refraction by the annular walls 3 can be further reduced or eliminated by surrounding at least the transparent portion 4 of the capillary array 2 by a medium having a refractive index similar to that characteristic the capillaries 1. Preferably, the transparent portion 4 is surrounded by a liquid medium having a refractive index of about 1.3–1.5, such as water. It is particularly convenient to immerse the entire capillary array 2 in water.

Side-entry irradiation of target species in a capillary 1 is effected through the transparent portion 4 of the annular wall 3 of each capillary 1 in the array 2, as shown in FIG. 1. Light passes through the transparent portion 4 of each capillary 1 in the array 2 in a sequential manner. A coherent light source 7 is positioned to direct a beam 8 of coherent light along the transparent path 5. A coherent light source produces light waves traveling together in phase. The light preferably has a wavelength of about 200–1,500 nm. Preferably, the coherent light source 7 used is a laser. An argon ion laser operating simultaneously at one or more visible lines is typically used for excitation, although other light sources and wavelengths can also be used. Particularly preferred excitation wavelengths are 488 nm and 514 nm. A pure output laser, i.e., a laser emitting light of a single wavelength, is a particularly preferred light source. Alternatively, the wavelength of the laser can be chosen by an interference filter or a glass prism.

The beam 8 of coherent light can be focused and collimated through a collimating focusing lens 9 interposed between the coherent light source 7 and the capillary array 2. Preferably, the collimated excitation beam 8 has a diameter of less than about 300 μm, more preferably less than about 75 μm while traversing the capillaries 1 in the array 2. For an array of about 100 capillaries, the array width is about 1.5 cm, and a lens with a focal length of about 5–30 cm, preferably about 10 cm, is used to focus and collimate the beam 8 such that the beam diameter remains less than about 75 μm while in the capillaries 1.

The focused line of the laser may be altered with a beam expander 10 in order to more effectively irradiate a large number of capillaries. The laser beam 8 is expanded perpendicular to the capillary array 2, as shown in FIG. 1. This lengthening or "fanning out" of the laser line makes it easier to position the beam so that all capillaries are adequately irradiated. The beam 8 can optionally be altered or redirected, as with a mirror 11, filter L2 or lens 13, prior to contacting the array 2. In FIG. 1 two mirrors 11 are used to provide a convenient means for adjusting the direction of the laser beam 8 to become coplanar with the capillary array 2 perpendicular to the capillaries 1. Also shown in FIG. 1 are a filter and a lens, although the use of mirrors, filters, lenses, or any combination thereof is optional.

Conveniently, the disclosed excitation and detection geometry allows the use of relatively low power output lasers (e.g., several mW, typically 0.5–50 mW. Because the laser beam 8 sequentially passes through all the capillaries, and because of the low concentration of DNA samples (typically about $10^{-10}$M), very little of the laser beam is wasted. Furthermore, the geometry is simple and readily scalable up to at least about a thousand capillaries. For example, detection systems are commercially available to image 2048 capillaries. The array width in that case will be 30 cm, which is still compatible with large-format wide-angle lenses. It may no longer be possible to maintain a 75-μm or narrower beam over this width; however, one can readily use higher laser powers in an unfocused beam to compensate for the mismatch in size between the laser and the capillary cores.

Figure 3:
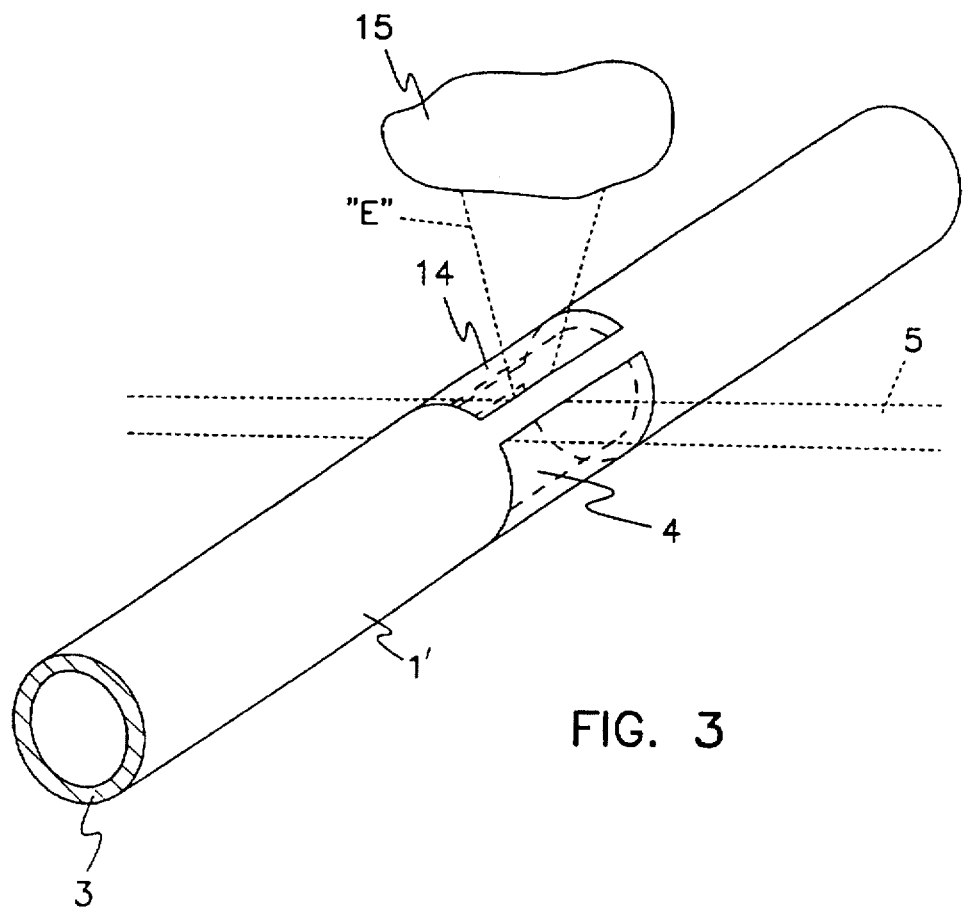
FIG. 3 shows optical coupling of a transparent path to a location external to the capillary array.

FIG. 3 shows an alternative embodiment of the system "S" wherein the annular walls 3 of the capillaries 1' have a second transparent portion 14 for optically coupling the transparent path 5 to a location 15 external to the capillary array, such that electromagnetic radiation can travel between the two sites. This embodiment is especially advantageous for fluorescence detection of target species. The second transparent portion 14 is transparent to light having a wavelength about equal to the wavelength of light emitted by a fluorescing target species, designated "E" in FIG. 3. Preferably, the second transparent portion 14 is transparent to light having a wavelength of about 200–1,500 nm, more preferably about 250–800 nm. The second transparent portion 14 of each annular wall 3 may conveniently be contiguous with or overlap the first transparent portion 4 of each annular wall 3.

As shown in FIG. 1 at least one capillary 1 may be in fluid communication with a sample 6 so that the sample 6 is drawn into the capillary 1. Preferably, the sample contains a fluorescent target species. The first transparent portion 4 of the annular wall 3 preferably exhibits substantially no fluorescence when exposed to the beam of coherent light 8, so as to eliminate background fluorescence from the detected fluorescence. More preferably, the first transparent portion 4 exhibits substantially no fluorescence when exposed light having a wavelength of 200–1500 nm, most preferably 250–800 nm. By substantially no fluorescence is meant that the level of fluorescence emitted by the transparent portion, if any, is less than observed background fluorescence. Detection of a target species is preferably effected through the second transparent portion 14. Accordingly, the second transparent portion preferably exhibits substantially no fluorescence when exposed to light having a wavelength about equal to the wavelength of light emitted by a fluorescing target species, "E". Most preferably, the entire capillary 1' is constructed from a transparent, non-fluorescing material, such as fused silica. Transparent windows may alternatively be formed in commercial capillaries having an external polyimide coating by removing a portion of the coating, as disclosed above.

The location 15 external to the capillary array to which the transparent path 5 may be optically coupled is to be broadly understood as any point, line, or planar surface external to the array, including a single pixel, linear array of pixels, or planar array of pixels. Preferably, the location 15 external to the capillary array comprises a planar surface parallel to the capillary array. The location 15 external to the capillary array preferably contains an optical detector 16. A suitable optical detector is capable of detecting fluorescence emission from a target species in a sample in a capillary. Preferably, the optical detector is a two-dimensional image array detector. More preferably, the optical detector is a charge-coupled device (CCD) or a charge-injection device (CID). Most preferably, the optical detector is a CID.

Where a capillary contains fluorescing target species, fluorescence detection can also be effected by any convenient alternative means, as by using optical fibers. Optical fibers can, for example, be optically coupled to the transparent path 5 axially by inserting one or more optical fiber into a capillary (Yeung et al., U.S. Pat. No. 5,324,401, Jun. 28, 1994, incorporated herein by reference).

Also provided by the invention is a method for detecting fluorescent target species in a sample using a multiplexed capillary electrophoresis system "S" having the side-entry excitation geometry disclosed above. A capillary array 2 of coplanar parallel capillaries 1 as shown in FIG. 1 is provided. As shown in FIG 1 each capillary has an intake end 17, an outflow end 18, and an annular wall 3 with a first transparent portion 4 defining a transparent path 5 extending through the capillary array 2 perpendicular to the capillaries 1. A sample containing a fluorescent target species in introduced into the intake end 17 of at least one capillary 1 such that the sample migrates through the capillary 1 toward the outflow end 18. Preferably, sample introduction is accomplished using pressure injection as disclosed in more detail below. Fluorescence emission is induced from the target species by irradiating it with a beam of coherent light 8 directed along the transparent path 5 (see FIG. 2). Preferably, the coherent light has a wavelength of about 200– 1500 nm. Fluorescence emission from the target species is detected. In a preferred embodiment of the method, the annular wall 3 of each capillary 1' in the array 2 has a second transparent portion 14 for optically coupling the transparent path 5 to a location 15 external to the capillary array, as shown in FIG. 3, through which the fluorescence emission is detected. For example, fluorescence may be detected by a CCD or a CID positioned at the optically coupled location external to the capillary array. Preferably, the first transparent portion 4 exhibits substantially no fluorescence when exposed to the coherent light used to irradiate the target species. More preferably, the first transparent portion 4 exhibits substantially no fluorescence when exposed to light having a wavelength of 200–1500, most preferably 250–800 nm. In a preferred embodiment of the method, the target species comprises DNA fragments.

Detection Methods and Devices. The present invention also provides a capillary electrophoresis system having an image array detector optically coupled to at least one of a plurality of coplanar parallel capillaries in a capillary array. The capillaries in the array each have an annular wall containing a transparent portion for optically coupling the interior portion of the capillary to the image array detector. Preferably, the capillaries are substantially adjacent along their parallel lengths. The capillaries may be grouped into subsets or subarrays, as disclosed above. An image array detector detects images of the interior of a capillary using pixels for collecting electromagnetic radiation in the form of photons. A pixel is an image collecting element of the array detector positioned to electronically detect the pictorial elements of interest during the time the pixel is exposed to electromagnetic radiation (e.g., light). A pixel is typically about 26 micrometers in diameter and adjacent pixels are typically spaced on a planar surface of the detector about 2–3 micrometers apart. A pixel exposed to electromagnetic radiation produces an electronic signal that is directly proportional to the amount of electromagnetic radiation received during the time it is exposed. This signal is then used for data analysis.

Specifically, the capillary electrophoresis system of the invention contains an image array detector having linearly aligned pixels located in a plane parallel to the capillary array such that at least one of the capillaries in the capillary array is optically coupled to less than about six of the pixels. The pixels in the linear array may be optically coupled to the interior portion of the capillary or to one of the capillary side walls. Preferably, at least one pixel is optically coupled to a side wall of a capillary proximate to the interior portion. Pixels optically coupled to a side wall have an unfavorable S/N because they are subject to interference from cross-talk and stray light associated with the capillary walls. These pixels can be conveniently disregarded during data collection and analysis when a charge-injected detector is employed as the image array detector, as further described below. In contrast, pixels optically coupled to the interior portion generally have a favorable S/N ratio. A particularly advantageous pixel alignment is one wherein only one pixel is coupled to an interior portion, and the two pixels on either side of the pixel coupled to the interior portion are each coupled to a side wall. In this arrangement, interference from cross-talk and stray light caused by the capillary walls is essentially confined to the pixels coupled to the side walls and does not affect the signal produced by the pixel coupled to the interior portion. This arrangement is preferred over an arrangement optically coupling two or more pixels to the interior portion because it minimizes dark current, which is a function of the number of pixels coupled to the interior portion of a capillary, although such less preferred arrangements are to be understood as also encompassed by the invention for certain embodiments.

Figure 4:
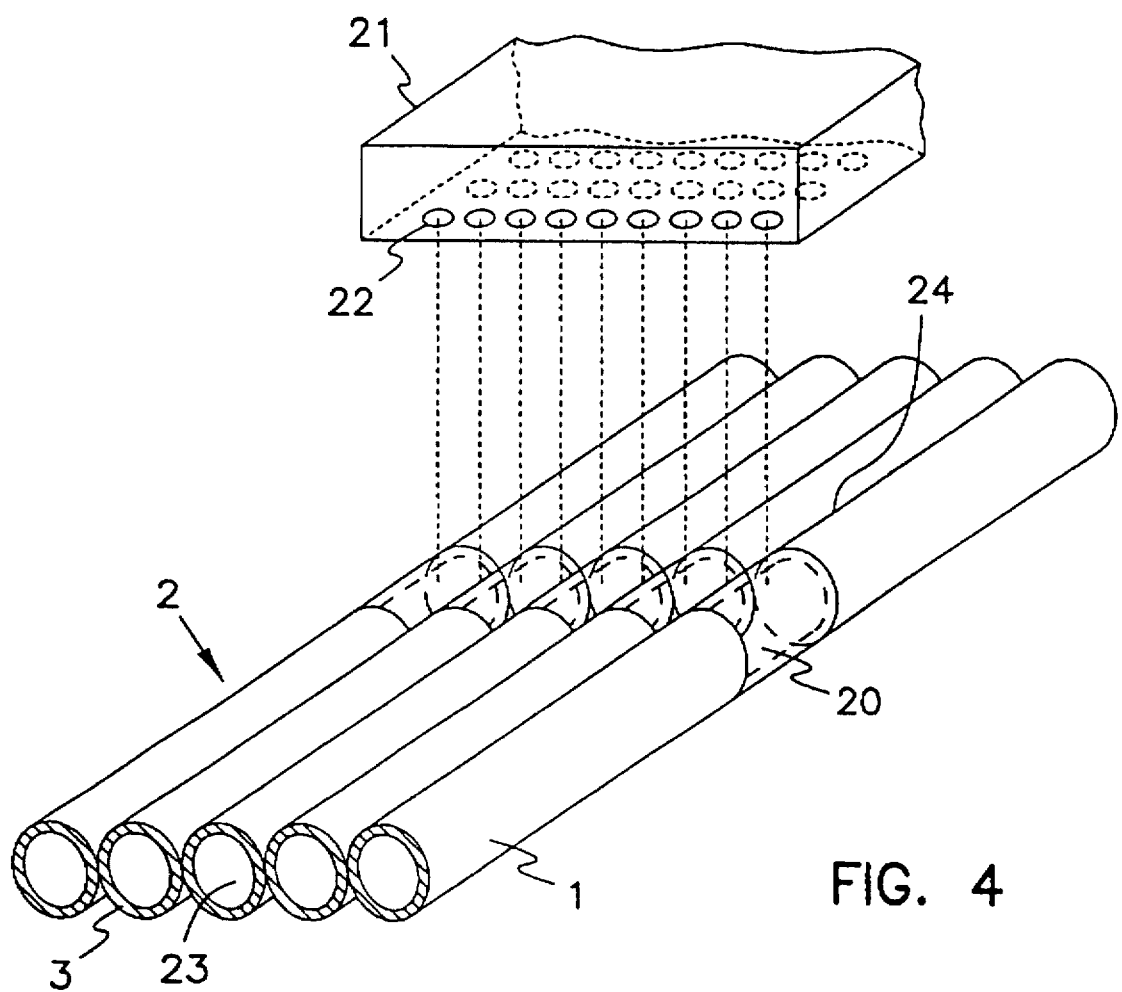
FIG. 4 shows optical coupling of pixels in an image array detector with the interior portion and side walls of a capillary in an array of substantially adjacent coplanar parallel capillaries having a pixel to capillary ratio of 2:1.
Figure 5:
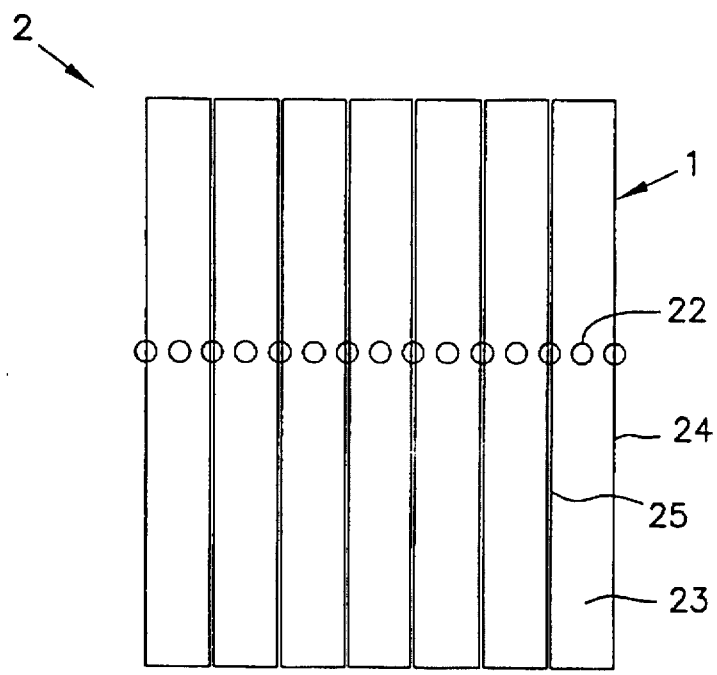
FIG. 5 is an overhead view of the 2:1 optical coupling arrangement shown in FIG. 4.

A particularly preferred embodiment of the invention is shown in FIG. 4. The capillary electrophoresis system contains a capillary array 2 containing a plurality of coplanar parallel capillaries 1. In this embodiment the transparent portion 20 of the annular wall 3 extends around the capillaries 1, and the capillaries 1 in the array 2 are substantially adjacent. An image array detector 21 having a linear array of pixels 22 located in a plane parallel to the capillary array 2 is optically coupled to the interior portions 23 of the capillaries 1. In this embodiment the ratio of pixels 22 to capillaries 1 is 2:1, and the pixels 22 are positioned such that every second pixel in the linear array is optically coupled to a side wall 24 of a capillary 1, and every pixel in between is coupled to an interior portion 23 of a capillary 1. FIG. 5 is an alternative view of the capillary array 2 shown in FIG. 4, showing a projection of the optically coupled pixels 22 onto the interior portions 23 and side walls 24, 25 of the substantially adjacent capillaries 1.

Figure 6:
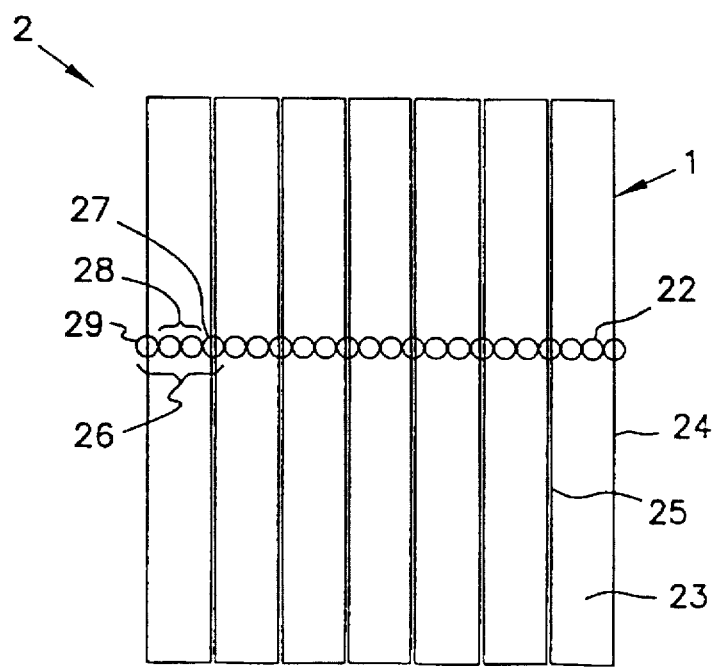
FIG. 6 shows an overhead view of an alternative optical coupling arrangement wherein the pixel to capillary ratio within the array of substantially adjacent coplanar parallel capillaries is 3:1.

In another embodiment of the invention shown in FIG. 6, a group of pixels 26 having a leading pixel 27, a middle group of pixels 28, and a trailing pixel 29, optically coupled to a capillary 1. Specifically, the leading pixel 27 is optically coupled to the first side wall 24 of a capillary 1, the middle group of pixels 28 is optically coupled to an interior portion 23 of a capillary 1, and the trailing pixel 29 is optically coupled to a second side wall 25 of a capillary 1. Preferably, the middle group of pixels comprises two pixels as shown in FIG. 6; most preferably, it comprises one pixel, as shown by implication in FIGS. 4 and 5. In FIG. 6, the optically coupled pixels 26 are graphically projected onto the capillaries 1 in the array 2 for ease of illustration. Two pixels 28 are optically coupled to each capillary interior 23. The pixels 27,29 optically coupled to a side wall 24,25 are shared by adjacent capillaries 1.

The ratio of optically coupled pixels to capillaries is less than about 6:1, preferably equal to about 3:1 and more preferably equal to about 2:1 for a capillary array of substantially adjacent coplanar capillaries. A 2:1 ratio is shown in FIGS. 4 and 5; a 3:1 ratio is shown in FIG. 6. The coplanar parallel capillaries may be arranged in an array comprising one or more subsets of substantially adjacent coplanar capillaries. In that event, the overall ratio of optically coupled pixels to capillaries for the entire array may be greater than 6:1, although for each subset of substantially adjacent coplanar capillaries the ratio is less than about 6:1. The ratio of optically coupled pixels to capillaries need not be an integer ratio. In that event, the number of pixels optically coupled to each capillary in the array may vary (see FIG. 8, described below). Likewise, if the capillaries in the array have variable diameters, the number of pixels optically coupled to each capillary in the array may vary.

Figure 7:
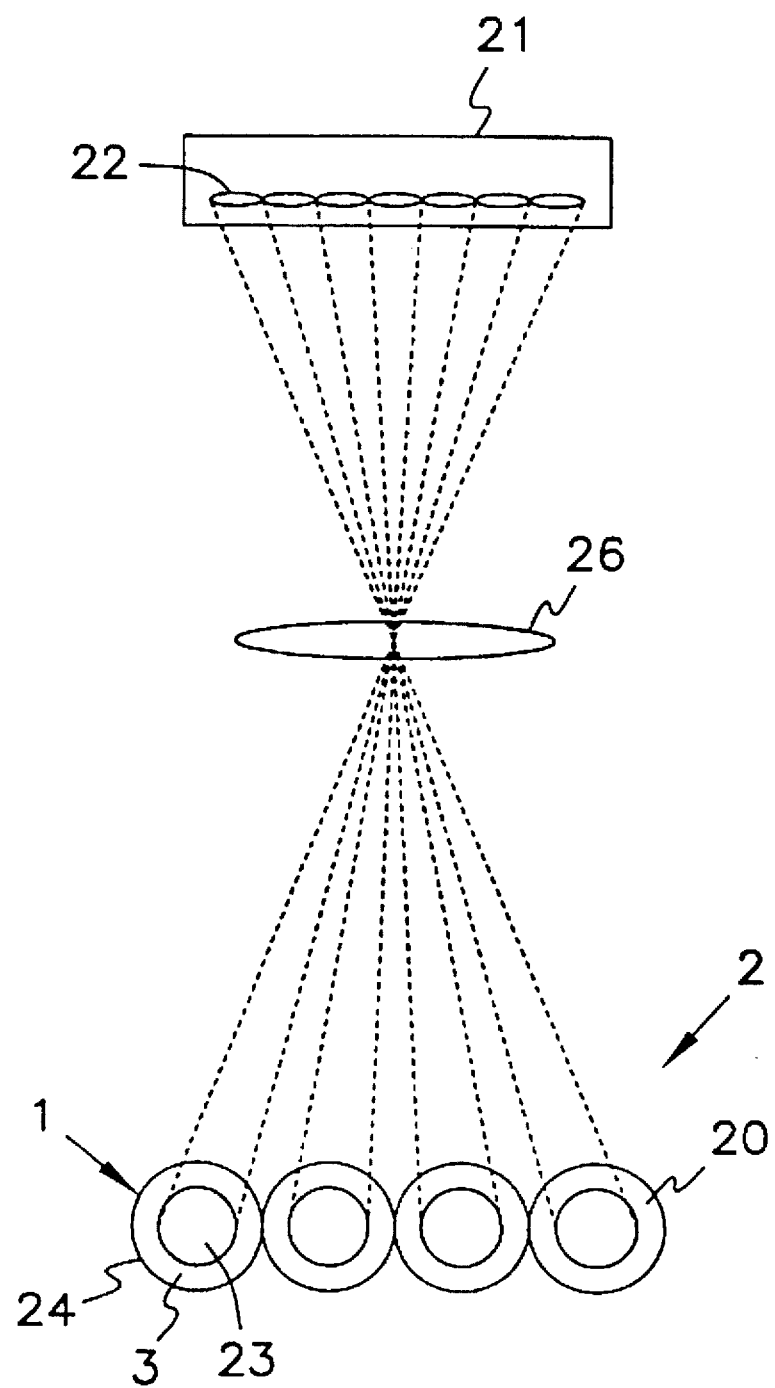
FIG. 7 is a cross-sectional view of a 2:1 optical coupling arrangement with an imaging lens interposed between the pixels and the capillaries that are optically coupled to the pixels.

In another preferred embodiment of the invention (FIG. 7) an imaging lens 26 is interposed between the capillary array 2 and the image array detector 21 used to optically couple the pixels 22 to the capillaries 1. The alignment in FIG. 7 shows a 2:1 ratio of pixels 22 to capillaries 1, wherein every second pixel is optically coupled to a side wall 24 and every pixel in between is coupled to an interior portion 23 of a capillary 1 through the transparent portion 20. The imaging lens 26 may be any lens capable of transforming an image onto the pixels of the image array detector, such as camera lens, for example a 24 mm wide-angle lens (Canon, Tokyo, Japan, Model FD 24 mm F1.4L, 50 mm diameter) or a condenser lens.

The image array detector may be a linear image array detector or a two-dimensional image array detector. Preferably it is a two-dimensional image array detector, more preferably a charge transfer device such as a charge-coupled device (CCD) or a charge-injection device (CID). Most preferably, the image array detector is a CID.

Also provided by the invention is a method for detecting fluorescent target species in a sample using the capillary electrophoresis system described in the preceding paragraphs. According to the method of the invention, a capillary array containing a plurality of coplanar parallel capillaries is provided. The annular wall of each capillary contains a transparent portion for use in optically coupling the interior portion of the capillary to an image array detector. The image array detector may be a linear image array detector or a two-dimensional image array detector. Preferably, the image array detector is a two-dimensional image array detector. More preferably, it is a CCD or a CID, most preferably a CID. The image array detector has linearly aligned pixels located in a plane parallel to the capillary array. The detector is optically coupled to the capillary array such that at least one of the capillaries in the array is optically coupled to less than about six of the linearly aligned pixels. A sample containing a fluorescent target species, preferably a DNA fragment, is introduced into the intake end of the optically coupled capillary such that it migrates through the capillary toward the outflow end. Fluorescence emission from the target species is then induced by irradiating it with a beam of coherent light. Preferably, the irradiating light has a wavelength of about 200–1500 nm, more preferably about 250–800 nm. Fluorescence emission is detected by the image array detector through the transparent portion of the optically coupled capillary using the optically coupled pixels. Preferably, detection is effected at about 20°–30° C.

In a preferred embodiment of the method, the pixels optically coupled to a capillary constitute a group of less than about six pixels, containing a leading pixel, a middle group of pixels, and a trailing pixel (see FIG. 6). Prior to the introduction of a sample, the leading pixel is optically coupled to a first side wall of a capillary, the middle group of pixels is optically coupled to the interior portion of a capillary, and the trailing pixel is optically coupled to a second side wall of the capillary. Preferably, the middle group contains two pixels. More preferably, it contains one pixel.

Figure 8:
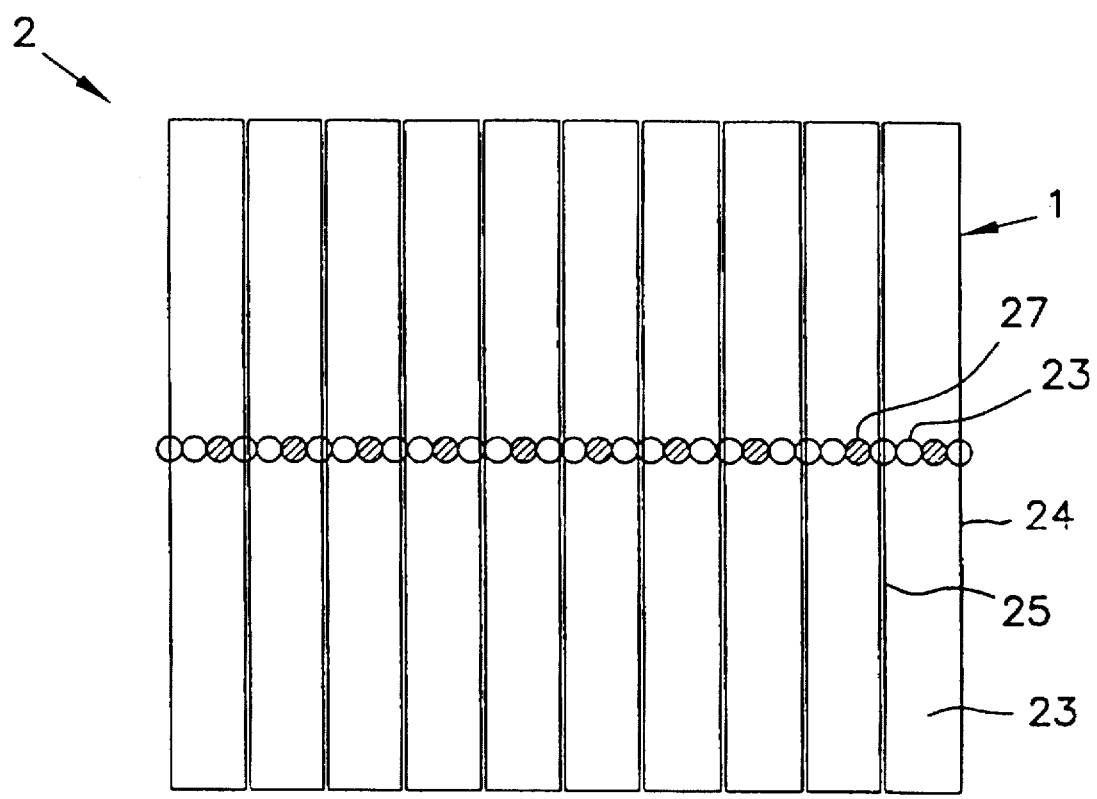
FIG. 8 is an overhead view of an alternative optical coupling arrangement wherein the pixel to capillary ratio within an array of substantially adjacent coplanar capillaries is not an integer ratio.

A further embodiment of the method includes the additional step of selecting one pixel from the middle group of pixels and using that pixel to detect the fluorescence emission from the target species. Where more than one pixel is optically coupled to the interior of a capillary, it is desirable to select only one to analyze and to disregard the others, since the dark current increases with the number of pixels evaluated per capillary, thus increasing background noise. In an array or subarray of substantially adjacent capillaries, ideally only one pixel is optically coupled to each capillary (representing a 2:1 ratio of pixels to capillaries), obviating the need to make a pixel selection. However, in large arrays with many capillaries, it may be of great practical utility to use a higher ratio of pixels to capillaries, to accommodate inconsistancies and variations in capillary packing, annular wall width, and the like. Where higher ratios of pixels to capillaries are used, more than one pixel may be optically coupled to a capillary interior portion. Each of these pixels will produce a signal having an intensity directly proportional to the intensity of light detected. The pixel producing the signal having the greatest intensity when exposed to electromagnetic radiation emanating from the capillary, i.e., the "brightest" pixel, is advantageously selected. Examples of selected pixels 27 are shown by hatched shading in FIG. 8. In FIG. 8, the optically coupled pixels 23 are graphically projected onto the capillaries in the array for ease of illustration. A hatched pixel represents that pixel optically coupled to a given capillary which produces the greatest signal intensity when the capillary contains a fluorescing material as described below. Data from the hatched pixels is used for sample analysis.

Selection of the appropriate pixel from those optically coupled to the interior portion of a capillary may conveniently be made by way of a calibration step. Thus, the method of the invention further includes a calibration step performed prior to introducing the sample. A fluorescing medium, such as a fluorescein solution, preferably a solution containing about $10^{-8}$–$10^{-5}$M fluorescein, or a rhodamine solution, or any convenient fluorescing buffer, is introduced into a capillary. Fluoresence emission is induced from the fluorescing medium by irradiating the medium with a beam of coherent light having a wavelength of about 200–1500 nm, and is detected using the image array detector through the transparent portion of the annular wall. The fluorescence emission is detected by each member of the middle group of pixels optically coupled to the interior of the capillary. The intensity of the signal produced by each pixel in the middle group is compared, the pixel producing the signal with the greatest intensity is selected. The fluorescence emitted by a target species detected by the selected pixel is then used to perform data analysis.

The most preferred image array detector for use in the system and method of the invention is the charge-injection device. Applications of CID are known in the fields of astronomy and atomic spectroscopy (P. Epperson et al., *Anal. Chem.*, 60, 327A (1988)). A CID is a solid-state charge-transfer imaging device (CTD) similar to a CCD, but it has characteristics not shared by CCDs that can be used to great advantage in multiplexed capillary electrophoresis. Where only a single capillary or a small number of capillaries is involved, there is no obvious advantage to using a CID because various photomultiplier tubes, avalanche photodiodes, or CCD cameras are available. However, when a large number of capillaries need to be monitored simultaneously in an array format, the unique features of a CID camera can make a significant difference. Those features include random pixel addressing, flexibility of user programmable architecture (particularly for programming exposure time), large dynamic range, low dark current, anti-blooming imaging, high tolerance to irradiation, high quantum yield over a wide wave-length range, and non-destructive readout.

The "random access" or electronic-windowing function unique to CIDs is especially useful. The term "random access" refers to the special features of a CID that allow it to be calibrated or programmed to read only those pixels focused on a particular region of interest, saving enormous data analysis time and storage requirements compared to a CCD, which offers very little flexibility in the pixel readout. For example, a CID can be calibrated to read only one or more pixels focused on a transparent portion of a capillary through which fluorescent emissions from a target species pass. Thus, the method of the invention further includes using random access programming to select a pixel having the greatest signal intensity from a group of pixels optically coupled to a capillary interior. The sample migration time for the target species is then determined by processing the signal produced by the selected pixel.

Although the CID camera is operated at a pixel-read rate slower than a conventional CCD, it can achieve very high sampling rate with high exposure duty cycle and thus high sensitivity. The advantages are even greater when several spatially separated subarrays need to be read, as the space in between the subarrays need not be read in a CID.

The CID can be further advantageously operated by programming it to utilize different exposure times to detect emissions of variable intensities. Shorter exposure time may be adequate for high intensity emissions, and longer exposure times can be used for lower intensity emissions. For example, a calibration run may be made in a DNA sequencing experiment to determine the approximate migration times of DNA fragments of various lengths. An exposure-time gradient can be then programmed to expose larger, longer running fragments having higher emission intensities for a shorter amount of time than needed for the faster, shorter fragments, thereby improving the signal to noise ratio for the larger DNA fragments while simultaneously reducing the volume of data generated. Thus, the method of the invention further includes using exposure time programming to vary the exposure time for a selected pixel during sample migration substantially inversely with the intensity of fluorescence emission from the target species. The exposure time programming is preferably effected by programming a time exposure gradient, which may be initially determined in a calibration run using DNA fragments of known size and fluorescence intensity, or by programming a feedback loop to automatically vary the exposure time with the fluorescence emission intensity detected by the selected pixel. In a particularly preferred embodiment of the method, both random access programming and exposure time programming are used.

To overcome any sampling rate limitations of a CID due to the fact that the sampling rate is determined by the charge-injection speed as well as the pixel-read rate, the CID can be operated using an asynchronous scanning mode. In an asynchronous scanning mode, the camera shutter is kept open and the subarray is scanned continuously without waiting between frame readouts to move to the next member of the array. The charge in each pixel is cleared individually during each frame without disturbing the other pixels. The duty cycle, frame rate, and charge-clearing time will vary as a function of the size of the subarray.

Preferably, the CID is operated at ambient temperature (20°–30°). This makes it simpler and more compact to incorporate into an automated DNA sequencing instrument. Because there is no need for a liquid-$N_2$ dewar, the CID focal plane array occupies only a very small space.

Nucleotide Identification in DNA Sequencing Experiments—"Base Calling".

When DNA sequencing is performed using fluorescence detection of DNA fragments in a single capillary, multiple dyes with distinct emission spectra are typically used to identify fragments corresponding to the four different bases. Many DNA sequencing detection schemes rely on the use of at least two excitation wavelengths, for example 488 nm and 543 nm (e.g., S. Carson et al., Anal. Chem., 65, 3219–3226 (1993)). However, when more than one beam is used to excite fluorescent species in a single capillary, matching of the migration times by normalization to the relative distance traveled is necessary in order to successfully read a sequence. Furthermore, multiple beams may produce scattered light that causes interference. Detection schemes using a single excitation wavelength and multichannel emissions detected using two or more photomultiplier tubes coupled to narrow bandpass filters have been reported (M. C. Ruiz-Martinez et al., Anal. Chem. 65, 2851–2858 (1993); X. C. Huang et al., Anal. Chem., 64, 2149–2154 (1992); J. M. Prober et al., Science, 238, 336–341 (1987); R. Tomisaki et al., Anal. Sci., 10, 817–820 (1994)), but the use of narrow bandpass filters, which admit light of a given wavelength ±10–30 nm, results in low light throughput, leading to a loss of sensitivity. Moreover, uniform incorporation by the polymerase must also be assumed. A four-dye label DNA sequencing experiment utilizing single wavelength excitation and multiwavelength CCD detection utilizing a spectrometer has also been reported (A. E. Karger et al., Nucl. Acids Res., 19, 4955–4962 (1991)), but low light throughput is a major drawback of this scheme as well.

Figure 9:
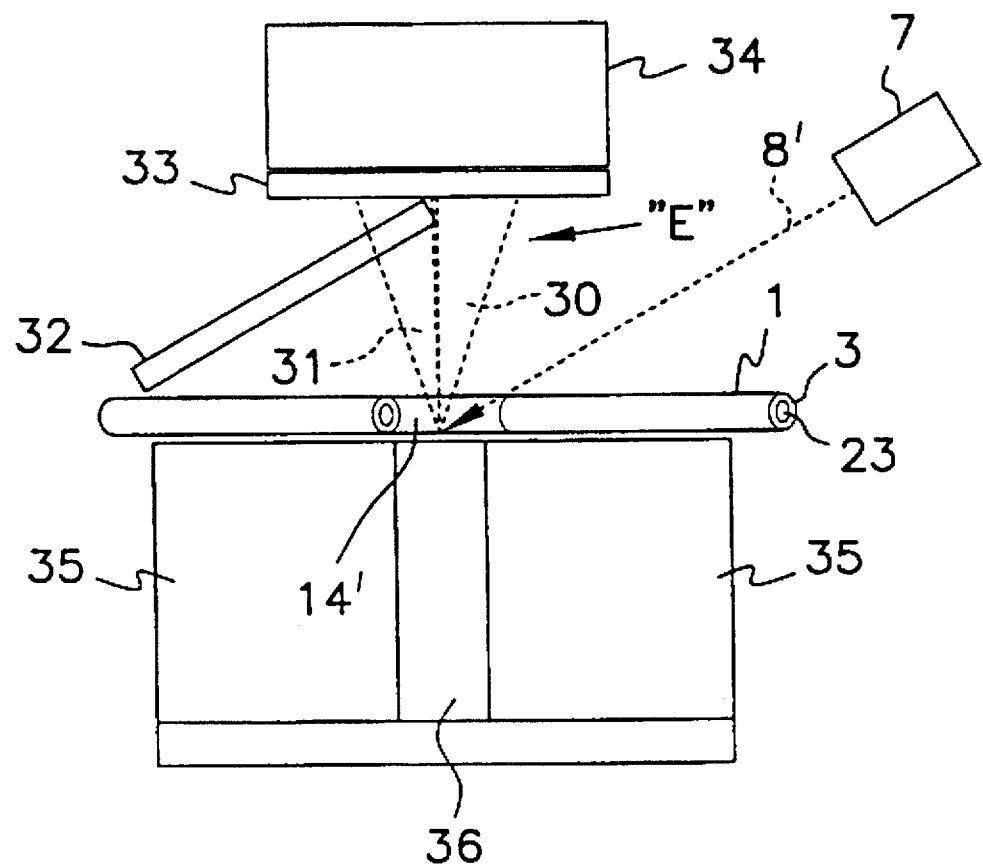
FIG. 9 is a schematic diagram of an optical arrangement used to split a line of induced fluorescence in a group of capillaries into two emission channels.

Accordingly, the present invention provides a capillary electrophoresis system to detect fluorescence emission from a fluorescent target species that utilizes only one excitation wavelength and that utilizes two long-pass filters, described below, to split the fluorescence emission into first and second emission channels. As a result of the splitting, the first and second emission channels contain light having different wavelength ranges. A detector simultaneously detects the fluorescence emission in the first and second emission channels. The invention is especially well-suited for use in DNA sequencing and DNA diagnostics experiments where the target species are DNA fragments, and all four nucleotide bases are detected in a single capillary. As illustrated in FIG. 9 and described in more detail below, a coherent light source 7 is positioned to direct a single beam of coherent light 8 so as to contact the interior portion 23 of at least one capillary 1, which is defined by its annular wall 3. A detector 34 is provided to detect fluorescence emission "E" from a fluorescent target species present in the capillary interior, which emission is split by the first 32 and second 33 long-pass filters into the first 30 and second 31 emission channels, respectively.

The capillary is in fluid communication with a sample containing a fluorescent target species such that the sample is drawn into the capillary, where it is brought into contact with the beam of coherent light. Excitation of target species in a capillary may be effected in any convenient manner, such as through the wall of the capillary, as described below, or axially using fiber optics. When a fluorescent target species is present in the capillary, the beam induces fluorescence emission from the target species.

Preferably, the annular wall of the capillary has a transparent portion through which fluorescence detection is effected, however fluorescence may be detected axially as well, as with one or more optical fibers inserted into the capillary, if an appropriate optical arrangement is used. In a preferred embodiment, the system contains a capillary array of coplanar parallel capillaries, each capillary having a first transparent portion defining a transparent path extending through the capillary array perpendicular to the capillaries. The beam of coherent light is directed along the transparent path. In a particularly preferred embodiment, each annular wall has a second transparent portion for optically coupling the transparent path to a detector, as further described below.

The long pass filters interposed between the target species and the detector are filters that transmit light having a wavelength longer than a stated value. A standard long pass filter with a stated wavelength value transmits about 50% of the light having the stated wavelength value, and decreasing percentages of light having shorter wavelengths, such that virtually no light having a wavelength shorter than about 50 nm below the stated value is transmitted. In contrast, a Raman type long pass filter has an abrupt cutoff. Virtually no light having a wavelength shorter than the stated wavelength of a Raman long-pass filter is transmitted. The use of long-pass filters permits a much greater amount of light to reach the detector than can reach the detector when narrow band filters are used.

Optimal excitation wavelengths and combinations of long-pass filters depend on the particular dyes used to label the DNA fragments in the sequencing reaction. In general, both filters screen out light having a wavelength at or below the wavelength used to excite the target DNA species. Typically, the first filter is selected to screen out stray laser light, i.e., light of a wavelength less than or about equal to the excitation wavelength, and the second filter is selected to screen out light of less than some higher wavelength, the cutoff value being dependent on the labels used to derivatize the DNA fragments.

Accordingly, the first long-pass filter preferably has a wavelength cutoff value such that it transmits less than about 0.1%, more preferably 0.01%, of light having a wavelength about equal to the wavelength of the single beam of coherent light used to induce fluorescence from the target species, and the second long-pass filter preferably has a higher wavelength cutoff value. How much higher depends on the dye labels used and will be readily apparent to one of skill in the art. More preferably, the first long-pass filter is a Raman long-pass filter having a wavelength cutoff value about equal to the wavelength of the single beam of coherent light.

Interposition of the two filters in the path of the fluorescence can be in either order. In a preferred embodiment of the invention, the first filter is positioned immediately adjacent to the detector, and the second filter is positioned between the target DNA species and the first filter, such that it intercepts a portion of the emission that would otherwise have passed directly through the first filter, and such that it is tilted at an angle of about 1°–89°, preferably about 20°–40°, relative to the first filter. The light passing through the second filter subsequently passes through the first filter before contacting the array detector, and constitutes what may be referred to as the "red channel". Light passing only through the first filter may correspondingly be referred to as the "blue channel", as it includes light having shorter wavelengths than that constituting the red channel. The amount of emission intercepted by the second filter can be adjusted to optimize the overall sensitivity of the two channels. Specifically, the ratios of the emissions detected by the two channels, which are used to determine the DNA sequence, are affected by the portion of the overall emission that is allocated to each channel by means of relative filter positioning. The second filter needs to be tilted to shift the image, via refraction, of the light passing through both filters, relative to that passing through only the first filter, to facilitate data analysis. It is particularly advantageous to use as the first filter a Raman long-pass filter which screens out wavelengths less than or about equal to the excitation wavelength and permits full throughput of higher wavelengths.

A preferred detector is a two-dimensional image array detector, especially in multiplexed systems, although first and second linear detectors may also be employed, one for each channel. More preferably, a charge-coupled device (CCD) or a charge-injection device (CCD) is used. In multiplexed systems where detection is effected using a CID or CCD, rectangular filters with dimensions in excess of the array dimensions may be conveniently used to split fluorescence emissions simultaneously induced from target species in multiple capillaries in an array of coplanar parallel capillaries.

A preferred embodiment of the system is shown in FIG. 9. A capillary 1 containing a fluorescent target species is placed on a mount 35 having a groove 36. The groove reduces stray light interference by preventing the reflection of the excitation beam by the mount which would otherwise occur if the groove was not present. A coherent light source 7 is positioned to direct a single beam of coherent light 8' so as to induce fluorescence from the target species through the transparent portion 14' of the annular wall 3 of the capillary 1. The fluorescence emission is split into a first channel 31 and a second channel 30. The first channel 31 contains the fluorescence emission that passes through both the Raman long pass filter 32 and a standard long pass filter 33. The Raman filter 32 is tilted at an angle of about 30° to the planar surface of the detector 34 in order to shift the image. The Raman filter 32 is positioned such that about half of the fluorescence emission from the target species contacts it. The second channel 30 contains that portion of the fluorescence emission that passes only through the standard long pass filter 33. Both channels are detected by a CCD detector 34.

In another preferred embodiment, a 488 nm laser line is used to excite fluorescence in the target DNA species labeled with PRISM™ dyes available from ABD division of Perkin Elmer (Foster City, Calif.). These four dyes have different emission wavelengths but similar excitation wavelengths. A 488-nm Raman long-pass filter is used to eliminate stray laser light. A 610-nm standard long-pass filter is tilted about 30° and covers roughly half the camera lens of a CCD, as shown in FIG. 9. The image is thus split into two emission channels with high light throughput, since long-pass filters rather than narrow band filters are used. Due to the use of the tilted second filter, the shifted image and the direct image automatically have the desired wavelength selections, and there is no time difference between the electropherograms from the two emission channels.

The invention further provides a method for detecting a fluorescent DNA fragment in a sample using the single wavelength excitation/two emission channel detection scheme described above. The invention is especially well-suited for use in DNA sequencing and DNA diagnostics experiments where the target species are DNA fragments, and all four nucleotide bases are detected in a single capillary. A capillary array of coplanar parallel capillaries is provided. Each capillary has an annular wall with a transparent portion optically coupled to a detector. A sample containing a DNA fragment is introduced into the intake end of at least one of the capillaries such that the sample migrates through the capillary toward the outflow end.

Preferably, sample introduction is accomplished using pressure injection, as disclosed in more detail below. Fluorescence emission from the DNA fragment is induced by irradiating the sample with a single beam of coherent light. The fluorescence emission is split by a first and second long pass filter into a first and second emission channel, respectively. Preferred optical arrangements and features of the first and second long pass filters for use in the method of the invention are disclosed above in the description of the capillary electrophoresis system. Fluorescence emission from both channels is detected through the transparent portion of the capillary wall.

Preferably, the detector used in the method of the invention is an image array detector, more preferably a charge-coupled device (CCD) or a charge-injection device (CID). A CID having linearly aligned pixels located in a plane parallel to the capillary is particularly preferred. Less about six of the linearly aligned pixels is optically coupled to at least one of the capillaries. These pixels may constitute a leading pixel, a middle group of pixels, and a trailing pixel. The method further comprises optically coupling a leading pixel to a capillary side wall, a middle group of pixels to the capillary interior, and a trailing pixel to the opposite side wall of the capillary. One pixel may be advantageously selected from each middle group prior to detecting the fluorescence emission. Preferably, this is the "brightest" pixel coupled to the interior of a capillary, as described above. Random access programming may then used to detect the fluorescence emission using the selected pixel. Exposure time programming may be used to vary the exposure time for a selected pixel inversely with fluorescence intensity during sample migration to further enhance resolution. Preferably, the DNA fragment is labeled using a fluorescent dye, such as the PRISM™ dyes (FAM and JOE, which are fluorescein derivatives, and ROX and TAMRA, which are rhodamine derivatives) available from ABD division of Perkin Elmer (Foster City, Calif.).

The method further comprises identifying the sequence of the DNA fragment by graphing the ratio of the emission intensities in the first emission channel vs. the second emission channel as a function of sample migration time to identify nucleotides in the sequence, i.e., to "call the bases". The method contemplates the use of a ratiogram, which is the ratio of the signals from the two emission channels, calculated point by point at each data interval. The ratio of intensities at these two independent channels is independent of concentration, which may vary across the peak, and can thus be advantageously used to sort out unresolved components in otherwise merged peaks.

Also provided by the invention is a method of using pressure injection to introduce samples into the intake end of a capillary in DNA sequencing experiments conducted in a multiplexed capillary electrophoresis system. Specifically, a capillary array of coplanar parallel capillaries is provided, each capillary having an intake end and an outflow end. Pressure is used to inject a sample containing a DNA fragment into the intake end of at least one capillary such that the sample migrates through the capillary toward the outflow end. Typical sample volumes are 0.1 to 50 nl. Fluorescence emission from the DNA fragment is induced by irradiating it with a beam of coherent light. Preferably, the coherent light has a wavelength of about 200–1500 nm, more preferably 250–800 nm. The fluorescence emission from the DNA fragment is subsequently detected by any convenient means.

Figure 15:
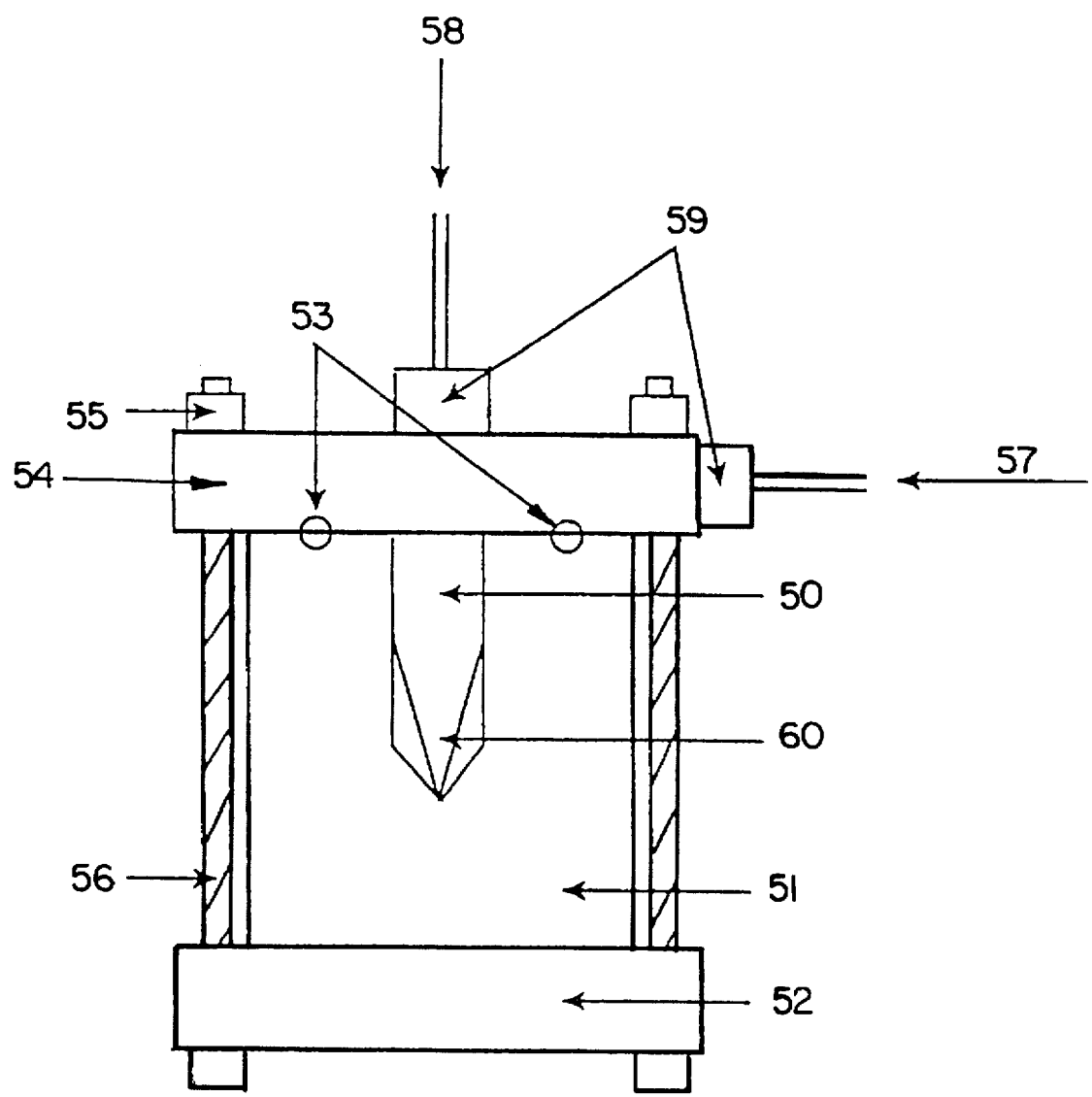
FIG. 15 is a schematic diagram of a pressure injection/flush cell for one capillary.

Pressure injection of the sample containing the DNA fragments is a superior method of sample introduction compared the electromagnetic injection commonly used in DNA sequencing experiments, particularly in a multiplexed environment. It alleviates problems with cross-contamination because an electrode does not have to be brought into contact with the sample. Pressure injection is typically accomplished using a pressure cell to isolate the high pressure environment. The sample container is placed in the pressure cell and the cell is sealed. Pressure may be supplied by gas, such as a nitrogen gas tank, or by a pump or compressed liquid. Preferably, the pressure used to inject the sample is about 50–150 psi (2500–7500 torr), more preferably about 100 psi (5000 torr). The capillaries may be conveniently fanned out at the intake end so as to allow contact with individual pressure cells or sample tubes within a pressure cell. FIG. 15 shows a suitable cell for pressure injection. The pressurized chamber 56 is set into a plexiglas block 51 mounted on a stainless steel surface 52. O-rings 53 provide a seal between the lid 54 and the block 57. A nut 55 and bolt 56 are used to seal the lid 54 in place. The lid 54 contains an inlet 57 for pressurized gas introduction and an outlet 58 for sample injection into the separation capillary, both secured by fittings 59. After the sample is placed in the sample container 60 the cell is sealed and pressurized. Nitrogen gas is applied to inject the sample into the capillary. Vacuum is not a suitable means of pressure injection because it does not support pressures in excess of one atmosphere, about 14 psi (760 torr).

Pressure injection of a sample may be combined with the use of a poly(ethyleneoxide) matrix to carry out electrophoretic separation, as disclosed below. The matrix is typically injected into the capillary using pressures of 100–400 psi (5000–20000 torr). A sample can be subsequently introduced into the capillary using pressure, preferably about 100 psi. At this pressure the sample will cause displacement of the polymer matrix equal to the volume of the sample. However, this small displacement has been found not to adversely affect separation performance.

Sieving Medium. To obtain the best separation efficiency for large molecules in capillary gel electrophoresis, it is important to have matrices with the right mesh size to obtain a suitable sieving effect for the solutes. Also, suppression of the interaction between the capillary wall and solutes is required to achieve separation efficiency. Increasing the capillary lifetime is another important consideration.

Accordingly, the present invention provides a polymer matrix containing poly(ethyleneoxide) (PEO), for use in capillary electrophoresis. Overall, PEO matrices provide several advantages, including easy preparation, better reproducibility, and longer lifetime as compared with cellulose-type matrices. Compared to linear polyacrylamide, PEO is more stable since no further polymerization of these commercial preparations is observed. There are linear polyacrylamide preparations available commercially. However, they are not yet available with a wide range of $M_n$, which turns out to be important for DNA separations, as disclosed below. The matrices described herein are particularly suited to DNA sequencing.

The polymer matrix of the invention is generally of a sufficiently low viscosity so as to enable it to be pushed into 50μm capillaries by pressure. The polymer matrix preferably has a viscosity of less than about 5,000 centipoise, more preferably less than about 2,000 centipoise, measured in a capillary at 1 atm, 25° C., using the Pouiselle equation. In one embodiment of the invention, the matrix is a single polymer matrix prepared from PEO with $M_n$ of between 2,000,000 and 5,000,000 at a concentration of about 2%–3%. This is referred to herein as a "single polymer matrix" because it is prepared from a single commercially available polymer product having the stated number average molecular weight ($M_n$). It is understood that even a commercially available polymer product with a stated $M_n$ is polydisperse; however, these products (e.g., from Aldrich Chemical Co., Milwaukee, Wis.,) show a generally small level of polydispersity around their stated $M_n$ value. Preferably, the single polymer matrix is prepared from PEO with $M_n$ 5,000,000 at a concentration between about 2% and 2.5%. In another embodiment of the invention, the polymer matrix is a mixed polymer matrix prepared from PEO of two or more different polymer products having number average molecular weights between about $M_n$ 300,000 and $M_n$ 8,000,000, at concentrations ranging from 0.5% to 2.0%, as desired for the particular application. The choice of molecular weights and concentrations will be determined by the length of the DNA fragments to be separated. Preferably, the mixed polymer matrix is prepared from either (a) 0.6% each $M_n$ 300,000, 600,000, 1,000,000, 2,000,000, 5,000,000 and 8,000,000 PEO, or (b) 0.7% each $M_n$ 300,000, 600,000, 1,000,000, 2,000,000, 5,000,000 and 8,000,000 PEO. In a particularly preferred embodiment, the mixed polymer matrix is prepared from a binary mix of two different polymer products, i.e., about 1.4% PEO 600,000 $M_n$ and 1.5% PEO 8,000,000 $M_n$. Even more advantageously, the binary matrix can be prepared in a buffer containing about 2-7M urea, more preferably 3-4M urea, most preferably 3.5M urea.

Any convenient detection method may be used to detect target species electrophoretically separated in a capillary electrophoresis system utilizing the polymer matrix of the invention. Fluorescence detection and detection using a mass spectrometer are preferred.

It is routine in the art to apply an internal polymer coating, such as γ-methacryloxypropyltrimethoxysilane and polyacrylamide (S. Hjerten, *J. Chromatogr.*, 347, 191 (1985)), to capillaries prior to use in capillary electrophoresis in order to protect the internal walls from being adversely affected by a high pH buffer environment used in experiments such as DNA sequencing. However, after several runs the protective coating gradually degrades, causing unwanted variations in electroosmotic flow that interfere with the interpretation of result. It was found, however, that the use of a protective internal coating is not the only way to address problems associated with electroosmotic flow. Specifically, good performance and resolution was observed whenever the silanol groups on the internal capillary walls of a capillary were in a protonated state prior to an electrophoretic separation.

Accordingly, an embodiment of the present invention provides a method for detecting a target species in a sample during capillary electrophoresis using a bare capillary that has been treated with acid to protonate the silanol groups on its internal wall. Specifically, a bare capillary having an uncoated fused silica internal wall is brought into contact with acid, preferably 0.01-0.5N hydrochloric acid, more preferably about 0.1N HCl, for a time effective to protonate the silanol groups on the capillary internal wall, typically by flushing for about 2 hours. A sample containing a target species, preferably a fluorescent target species, more preferably a fluorescent DNA fragment, is introduced into the intake end of the capillary such that it migrates through the capillary toward the outflow end. Preferably, the sample is introduced by pressure injection. The sample is then detected by any convenient means, preferably by fluorescence or mass spectrometry.

A polymer matrix, preferably poly(ethyleneoxide), may be placed in the bare capillary immediately prior to introducing the sample, preferably by pressure injection using pressure of about 100-400 psi (5000-20000 torr). Preferably, the polymer matrix solution contains a polymer with a viscosity of less than 5,000 centipoise, more preferably less than about 2,000 centipoise, measured as disclosed above. To maintain a high level of performance, the bare capillaries should be regenerated (reprotonated) often, preferably after every run, whether or not a polymer matrix is used. Thus, the method further includes regeneration of the capillary so as to extend its useful life, and replacement of used polymer matrix with fresh matrix. In a preferred embodiment, the used poly(ethyleneoxide) matrix is removed from bare capillary, and the capillary is flushed with acid to reprotonate the silanol groups, as described above. A fresh solution of poly(ethyleneoxide) matrix in then injected into the bare capillary, and another capillary electrophoresis experiment is performed. These steps can be repeated indefinitely, and multiple experiments can be performed using the same capillary, since the capillary is always regenerated in between runs using the acid wash. This protocol is particularly well suited to DNA sequencing experiments.

The invention further provides a capillary electrophoresis system that includes at least one bare capillary having an uncoated bare fused silica wall containing protonated silanol groups. The protonated capillary can be used in both capillary gel electrophoresis and capillary zone electrophoresis. If capillary zone electrophoresis is employed, the use of a dilute solution of polymer, preferably PEO, to dynamically coat and isolate the capillary walls from the high pH environment (about pH 8-9) of the buffer solution, is recommended to keep the silanol groups protonated as long as possible.

Integrated System. Each of the embodiments of the present invention constitutes a useful improvement in CE technology, particularly as it relates to DNA sequencing. However, it is to be understood that the various embodiments have an additional utility when used in combination in an integrated system. It may, for instance, be necessary to sacrifice the performance of one or more of the critical technologies to achieve a workable compromise for large-scale applications. Such is the case with the use of a CID as a detection device, which is more advantageous than a CCD in a highly multiplexed system, but may not be as efficient as a CCD in a smaller system. Thus, the present invention further provides an integrated CE system containing side-entry excitation geometry and a CID detector, and method for its use in DNA sequencing using a binary PEO polymer matrix and one laser/two emission ratiogram base calling.

Although the invention is directed generally toward use in a multiplexed capillary electrophoresis system, it will be understood by one of skill in the art that aspects of the invention can be advantageously applied in capillary electrophoresis systems containing only one or a few capillaries. For example, the base calling method of the invention, the polymer matrix of the invention, and the use of bare capillaries and capillary regeneration procedure for DNA sequencing can be easily adapted by one of skill in the art to either single or multiple capillary systems, as desired.

Advantages of the invention are illustrated by the following examples. However, the particular materials and amounts thereof recited in these examples, as well as other conditions and details, are to be interpreted to apply broadly in the art of capillary electrophoresis and should not be construed to unduly limit the invention.

EXAMPLES

Example I.

Poly(ethyleneoxide) for High resolution and High Speed Separation of DNA By Capillary Electrophoresis Absorption detection. A commercial instrument (Model 3850 ISCO; Lincoln, Nebr.) was used for all absorption studies. The detection wavelength was set at 260 nm. A 50 µm internal diameter (i.d.), 360 µm outer diameter (o.d.) DB-1 coated GC capillary (J & W Scientific, Folsom, Calif.) with 0.2-µm coating thickness was used without any further modification. The capillary length was 50 cm total with a 32 cm effective length (length to the detector). Electromigration injection was performed for 2 seconds at the running voltage (−10 to −30 kV).

Laser-induced fluorescence (LIF) detection. The experimental setup was similar to that described in P. Wang et al., J. Chromatogr., 608, 73 (1992). Briefly, a high-voltage power supply (Glassman High Voltage, Whitehorse Station, N.J.) was used to drive the electrophoresis. The entire electrophoresis and detection system were enclosed in a sheet-metal box with a high voltage (HV) interlock. An argon-ion laser with 488 nm output from Uniphase (San Jose, Calif.) and 1-mW He—Ne laser with 543.6 nm output from Melles Griot (Irvine, Calif.) were used for excitation. Where the DNA fragments labeled with thiazole orange dimer (TOTO), referred to herein as DNA-TOTO samples, were irradiated using the argon-ion laser, one 535-nm interference filter (Oriel Corp., Stratford, Conn.) was used to block scattered light and to allow the emitted light to reach the photomultiplier tube (PMT). Where the He—Ne laser was used to irradiate DNA-TOTO samples, one RG 610 cutoff filter and one 630-nm interference filter (Oriel Corp., Stratford, Conn.) were used. For DNA labeled with ethidium bromide, referred to herein as DNA-EthB samples, one RG 610 cutoff filter and one 630-nm interference filter were used during irradiation with both types of lasers. The fluorescence signal was transferred directly through a 10-kΩ resistor to a 24-bit A/D interface at 4 Hz (Justice Innovation, Palo Alto, Calif.; Model DT 2802) and stored in a computer (IBM, Boca Raton, Fla.; Model PC/AT 286).

Capillary and reagents. Capillaries (Polymicro Technologies, Phoenix, Ariz.) with 75 µm i.d. (inside diameter) and 365 µm o.d. (outside diameter) were used for fluorescence studies after they were coated with γ-methacryloxypropyltrimethoxysilane and polyacrylamide by Hjerten's method (S. Hjerten, J. Chromatogr., 347, 191 (1985)). All chemicals for preparing buffer solutions and for coating capillaries were purchased from ICN Biochemicals (Irvine, Calif.), except that acrylamide and formamide were from Sigma Chemical (St. Louis, Mo.), and poly (ethyleneoxide) (PEO) was obtained from Aldrich Chemical (Milwaukee, Wis.). Ethidium bromide (EthB) was purchased from Sigma. TOTO (thiazole orange dimer) was obtained from Molecular Probes (Eugene, Oreg.). The concentrations of dyes in the running buffer were 1 µg/ml. φX 174 DNA-Hae III restriction fragment digest was purchased from United States Biochemical (Cleveland, Ohio). pBR 322 DNA-Hae III, pBR 328 DNA-Bgl I+pBR 328 DNA-Hinf I restriction fragment digests were purchased from Boehringer Mannheim Biochemicals (Indianapolis, Ind.).

Methods. The buffer solution used to prepare the PEO matrices (Tris-borate-EDTA, or "TBE") contained equimolar amounts of tris(hydroxymethyl)aminomethane (THAM) and boric acid, with ethylenediaminetetraacetic (EDTA) as a chelating reagent for divalent cations. The resulting concentration of 1× TBE buffer was 89 mM THAM, 89 mM boric acid, and 2 mM EDTA. The pH of the 1× TBE buffer was 8.2 without any further adjustment. The matrix was prepared with poly(ethyleneoxide) (PEO) and TBE buffer solution to the desired concentration. Briefly, PEO was gradually added into the TBE buffer solution in a beaker sitting in a water bath at 85°–90° C. During the addition of PEO, a magnetic stirring rod was used at high speed to produce a well homogenized solution. After addition was complete, the solution was stirred for at least an additional 15 minutes.

Initially, the capillary was pressure-flushed with water, methanol, and water for at least 2 cycles. Then, the capillary was filled with very low viscosity polymer solution (e.g., 0.5% PEO) and run at −10 kV for 10 minutes. Finally, the capillary was refilled with the separation matrix and equilibrated at the running voltage for 15 minutes before sample injection. Air pressure was used to fill the capillary with the polymer solution and the total operation time was no more than 5 minutes. The capillary was used for over 2 weeks with more than 50 runs without any degradation.

The injected concentration of DNA for the mixed polymer separations was 0.83 µg/ml, and electroinjection was performed at −6 kV for 3 seconds. Between each run, the used polymer matrix was flushed out from the capillary, then the capillary was filled with new polymer matrix. Before the injection of the analytes, the capillary was equilibrated at −10 kV for 10 minutes.

Separation performance. To form a sieving medium, the concentration of polymers has to be higher than a certain value called the overlap threshold. Polymer chains then interact with one another to form an entangled solution. The average mesh size (ξ) of the pores formed can be expressed as $$\xi(\Phi) \sim A\Phi^{-0.75} \tag{1}$$

where Φ is the polymer volume fraction and A is a proportionality constant. Because Φ equals $S^{-0.8}$, where S is the size of polymer chain, Eq. (1) can be rewritten as $$\xi(\Phi) \sim AS^{0.6} \tag{2}$$

Hence, in order to create a small mesh, a polymer with short chains should be used, and vice versa. Further, in order to be able to fill the capillary easily with the matrix while keeping the optimal mesh size for good separation, it is desirable to have gel matrices with as low a viscosity as possible.

Electrophoretic separation of a φX 174 DNA-Hae III digest (250 µg/ml) was carried out in matrices prepared from PEO with $M_n$ 300,000 to 5,000,000 at different concentrations. Specifically, separations were carried out using the following matrices prepared with individual polymer products purchased from Aldrich Chemical Co. (Milwaukee, Wis.) having the indicated number average molecular weight ($M_n$) and a low level of polydispersity: (a) 3% $M_n$ 300,000, (b) 3.3% $M_n$ 300,000, (c) 2.75% $M_n$ 1,000,000, (d) 2% $M_n$ 2,000,000, (e) 3% $M_n$ 2,000,000, and (f) 2% $M_n$ 5,000,000. The applied potential during electrophoretic separation was −26 kV. These matrices are referred to herein as "single polymer matrices" in order to distinguish them from "mixed polymer matrices" prepared from two or more polymer products having different number average molecular weights, and from "binary polymer matrices" prepared from two polymer products having different number average molecular weights. It is understood that all polymer products necessarily have a level of polydispersity (deviation of particular polymer chains from the stated number average molecular weight).

For a comparable separation performance, concentrations of short chain polymers in solution (low $M_n$) need to be higher than those with long chains. Increasing the polymer concentration (fixed $M_n$) generally leads to higher resolution, at the cost of an increase in analysis time and increased difficulty in handling the higher viscosity matrix. In this experiment, fragments at 271/281/310 and at 872 bp (base pair) showed anomalous migration. Because molar absorptivity is proportional to the number of base pairs, however, the fragment peaks could be assigned based on peak area (H. M. Wenz, *Nucleic Acids Res.*, 22, 4002 (1994)).

Compared to cellulose-type gel matrices, the resolution between the 271 and 281 pair of fragments was much better using PEO matrices. Also, separation performed using PEO matrices provided highly reproducible results for at least 10 runs without replacement. The reproducibility among different capillaries and different batches of polymers was also excellent.

Figure 10:
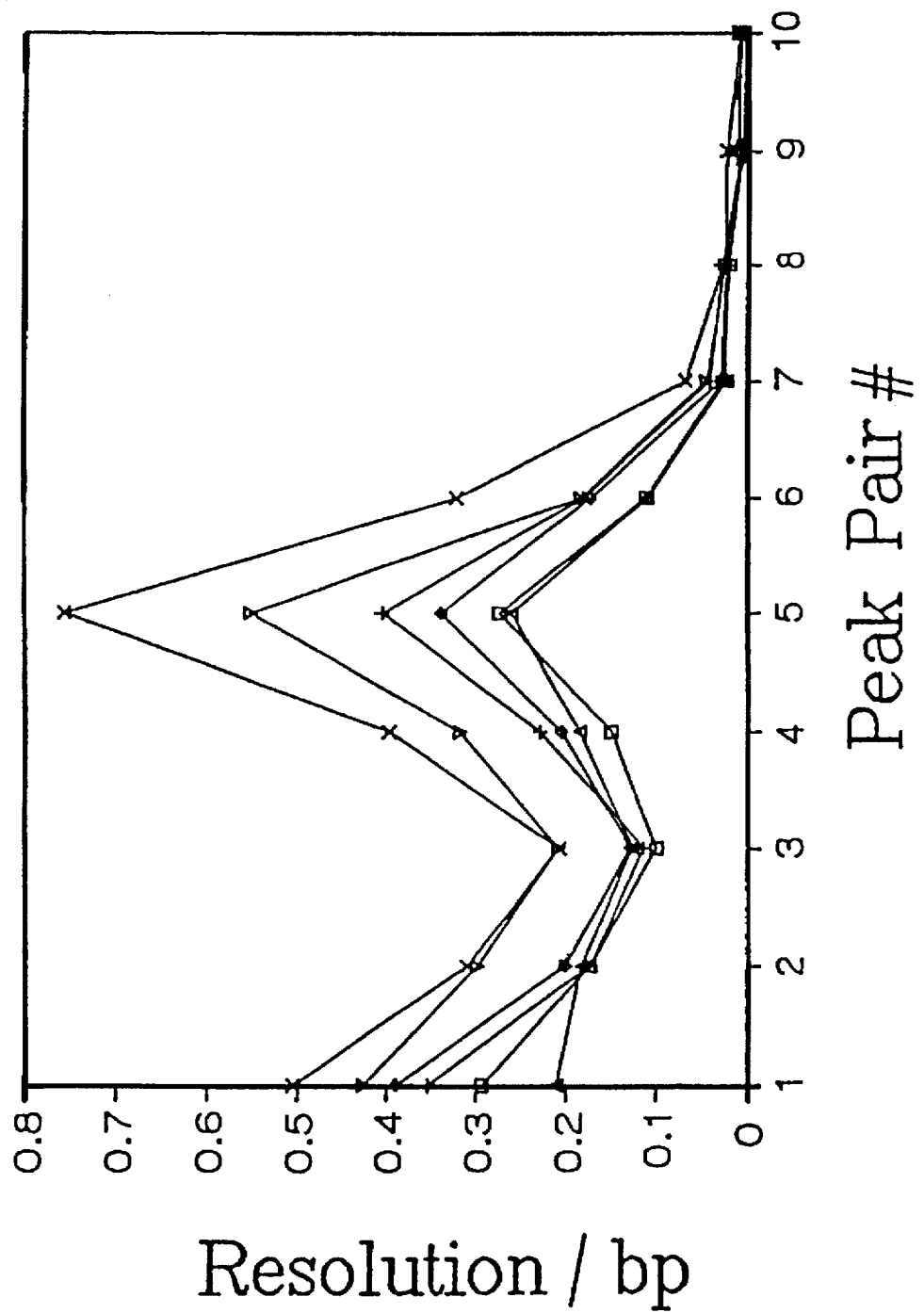
FIG. 10 shows base pair resolution of consecutive DNA fragment peaks in different polymer matrices.

Resolution. Resolution (R) is calculated as $$R = \frac{(2 \ln 2)^{1/2} \Delta t_R}{HW_1 + HW_2} \quad (3)$$

where $\Delta t_R$ is the difference in migration time between the two adjacent peaks, and HW is the full width at half maximum. FIG. 10 shows the change in resolution per base pair for consecutive pairs of fragments as a function of the polymer matrices. The symbols used are: ,3% $M_n$ 300,000;+, 3.3% $M_n$ 300,000; ◊, 2.75% $M_n$ 1,000,000; Δ, 2% $M_n$ 2,000,000; x, 3% $M_n$ 2,000,000; and ∇, 2% $M_n$ 5,000,000. The ordinate axis shows the numerical order of consecutive pairs of peaks. It is evident that matrices prepared from PEO with $M_n$ 2,000,000 at 3% provided the best resolution for DNA fragments. However, this solution was too viscous to be easily forced into 50μm capillaries by pressure. Overall, the best performance should be obtained from PEO with $M_n$ 5,000,000 at a concentration somewhat higher than 2%. Best per-base-pair resolution was observed for DNA fragments in the range 250 to 350 base pairs. The resolution degraded for DNA fragments longer than 600 base pairs.

The strength of the applied electric field also affects separation performance in CE. The shape of the DNA fragments and the degree of disruption of the network of polymers may vary with changes in electric field strength. Heat generated during an electrophoretic separation also increases with electric field strength. It is desirable to run CE at as high an electric field strength as possible to shorten the separation time. For short to medium length DNA fragments, resolution increased as electric field strength was increased from 220 V/cm to 520 V/cm, since longitudinal diffusion was minimized. Resolution degraded substantially at the higher electric field strength of 600 V/cm, however. For longer fragments, the resolution actually decreased as the electric field strength increased. Possible explanations include local heating distortions and large changes both in the shape of DNA and the mesh size of the polymer matrix at increasing electric field strengths.

Effects of intercalating dyes. One advantage of using LIF to monitor DNA separations is that very small amounts of DNA can be detected. Electrophoretic separation of 0.9 μg/ml of φX 174 DNA-Hae digest (11 fragments ranging in length from 72 to 1353 base pair) intercalated with (a) 9.5 μg/ml of TOTO (a dimeric intercalator or "bisintercalator") for at least 20 minutes before the separation, (b) 1 μg/ml of EthB (a monomeric intercalator, or "monointercalator") in the running buffer, and (c) 1 μg/ml of TOTO in the running buffer, were accomplished using a capillary having a total length of 60 cm and an effective length of 52 cm, and an applied potential of −12 kV. It was found that PEO matrices were compatible with both these intercalating dyes for the separation and detection of DNA fragments, but that EthB produced the sharpest peaks and reduced anomalous migration behavior. All 11 fragments were resolved when a dye was incorporated into the running buffer, however, when the digest was intercalated with TOTO prior to separation, only 9 peaks resolved. The separation performance and sensitivity decreased on successive runs whenever the dyes were incorporated into the running buffer. Therefore, it was important that the capillaries be refilled with new polymer solutions after each run. The degradation was worse when TOTO was in the running buffer. Possibly there exist strong interactions between TOTO and the polymer matrix or between the TOTO and the capillary wall.

Separations in single vs. mixed polymer matrices. Polymer matrices were prepared from single-$M_n$ materials as follows: (a) 9% $M_n$ 300,000, (b) 6% $M_n$ 600,000, (c) 3.5% $M_n$ 2,000,000, (d) 2.5% $M_n$ 5,000,000, (e) 2% $M_n$ 8,000,000 and (f) 2.5% $M_n$ 8,000,000. Electrophoretic separation of the 20 fragments contained in an EthB-stained pBR 322 DNA-Hae III digest was accomplished using a capillary having a total length of 50 cm and an effective length of 32 cm, and an applied potential of −10 kV. The 20 fragments ranged in size from 18 to 587 base pairs. Peak assignments were based on relative intensities. Matrices prepared from polymers with low molecular weights required a higher concentration of polymers. It was found to be impossible to separate DNA fragments less than 400 base pairs in matrices prepared from low molecular weight polymers ($M_n$ 300,000), even when a high concentration, up to 15%, was used. The pore size of the matrices was too small to have a sieving effect even for those short DNA fragments. For DNA fragments from 80 to 400 base pairs, better resolution was achieved in matrices prepared from single polymers with higher $M_n$ (e.g., $M_n$ of 600,000 to 2,000,000). However, no single polymer size used alone provided adequate efficiencies over the entire size range.

Drawing from the concept of gradient elution in chromatography, matrices prepared from mixtures of polymer sizes were studied. Mixed PEO matrices were prepared as follows: (a) 1.5% $M_n$ 300,000, 1.8% $M_n$ 2,000,000, 0.7% $M_n$ 5,000,000 and 0.7% $M_n$ 8,000,000; (b) 3.0% $M_n$ 1,000,000 and 1.3% $M_n$ 8,000,000; (c) 1.5% $M_n$ 600,000, 1.0% $M_n$ 1,000,000 and 1.5% $M_n$ 5,000,000; (d) 0.6% each $M_n$ 300,000, 600,000, 1,000,000, 2,000,000, 5,000,000 and 8,000,000; and (e) 0.7% each $M_n$ 300,000, 600,000, 1,000,000, 2,000,000, 5,000,000 and 8,000,000. Electrophoretic separation of the 20 fragments contained in an EthB-stained pBR 322 DNA-Hae III digest was accomplished as described for the single polymer matrices. In the mixed polymer matrices, a polymer network with random pore sizes is formed. The separation performance is different from that obtained using matrices made from single-$M_n$ polymers. This is because the mixed matrices simultaneously provide optimum pore sizes for a large range of DNA fragments. From comparison of the results of DNA mobilities in matrices prepared using single polymers, it was estimated that the average pore size of the mixed polymer matrices is between that made from 2.5% ($M_n$ 8,000,000) and 3.5% ($M_n$ 2,000,000) PEO. While the resolution for the longer fragments was worse in the matrix made from 3.5% PEO ($M_n$ 2,000,000) compared to mixed polymer matrices, the resolution of the short fragments was better. On the other hand, the matrix prepared from 2.5% PEO ($M_n$ 8,000,000) provided slightly higher resolution for DNA fragments from 80 to 400 base pairs compared to the mixed polymer matrices, but the resolution for shorter fragments was worse. For DNA fragments longer than 400 base pairs, relatively higher resolution can be obtained in mixed polymer matrices.

Figure 11:
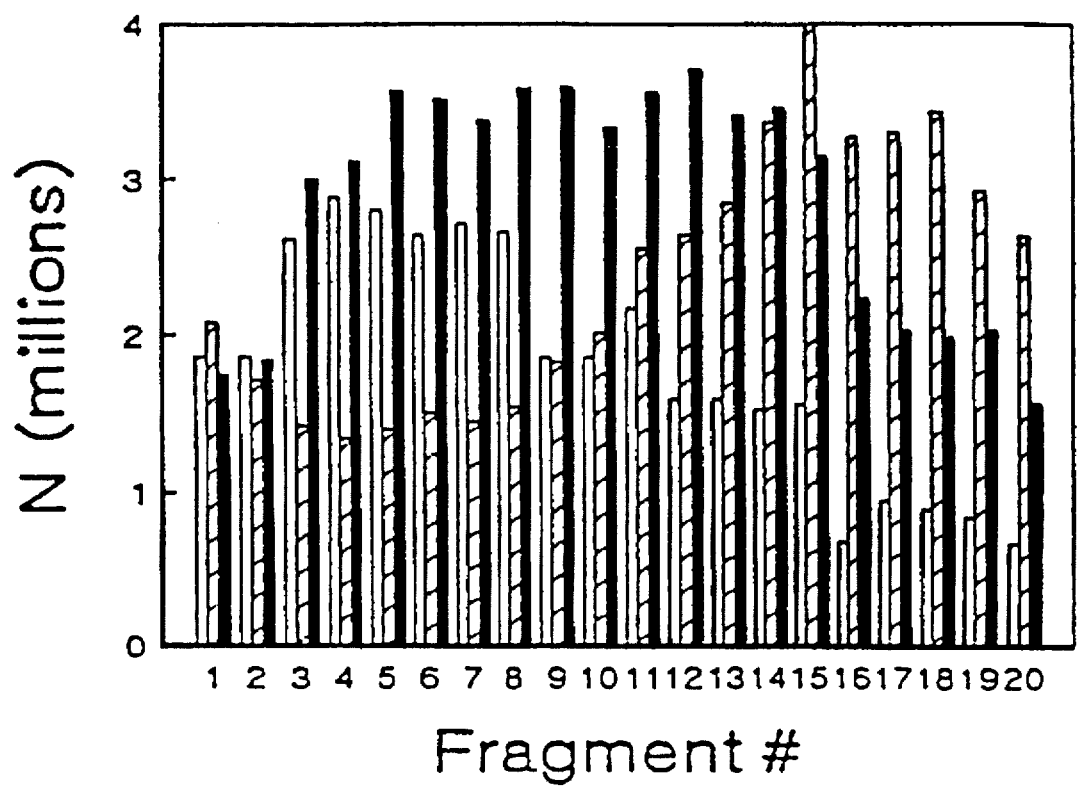
FIG. 11 is a graphical representation of a comparison of the theoretical plate numbers from the electrophoretic separation of a pBR 322 DNA-Hae III digest stained with ethidium bromide.

A representative comparison among the various PEO matrices is given in FIG. 11. Poly(ethyleneoxide) matrices were 6% $M_n$ 600,000 (open bar); 2.5% $M_n$ 8,000,000 (shaded bar); and 0.7% each $M_n$ 300,000, 600,000, 1,000, 000, 2,000,000, 5,000,000 and 8,000,000 (solid bar). Peak assignments (peak number=length of DNA fragment in base pairs) were: 1=18 bp, 2=28 bp, 3=51 bp, 4=57 bp, 5=64 bp, 6=80 bp, 7=89 bp, 8=104 bp, 9=123 bp, 10=124 bp, 11=184 bp, 12=192 bp, 13=213 bp, 14=234 bp, 15=267 bp, 16=434 bp, 17=458 bp, 18=504 bp, 19=540 bp and 20=587 bp. The low-$M_n$ material (6% $M_n$ 600,000) provided a more efficient separation for the shorter DNA fragments whereas the high $M_n$ material (2.5% $M_n$ 8,000,000) more efficiently separated the longer DNA fragments. In contrast, the mixed polymer solution showed good separation of a broad range of DNA fragments. The higher viscosity of the 0.7% solution may limit its utility in capillary array electrophoresis, however, because the matrix inside the capillaries must be readily replaceable. A 0.6% mixed polymer matrix, described below, provided comparable resolution to the single polymer matrices, while retaining a much lower viscosity.

Figure 12:
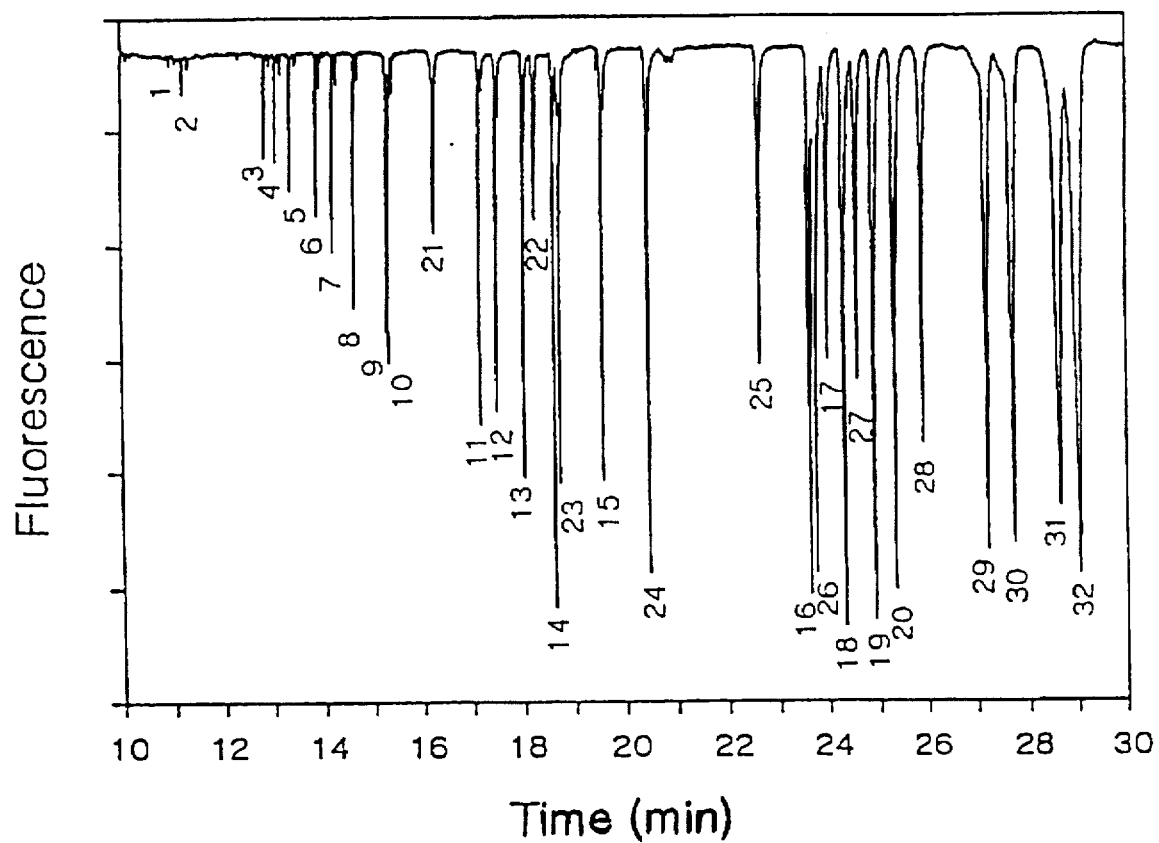
FIG. 12 shows electrophoretic separation of the mixture of pBR 322 DNA-Hae III, pBR 328 DNA-Bgl I, and pBR 328 DNA-Hinf I digests.

FIG. 12 shows the result of the separation of DNA fragments in a mixture of molecular weight markers containing DNA fragment sizes ranging in length from 8 to 2176 base pairs. A mixed PEO matrix (0.6% each $M_n$ 300,000, 600,000, 1,000,000, 2,000,000, 5,000,000 and 8,000,000) was used. Electrophoretic separation was as described for single polymer matrices. Peak assignments (peak number= length of DNA fragment in base pairs) were: 1 to 20 are as in FIG. 11, 21=154 bp, 22=220 bp, 23=234 bp (from pBR 328), 24=298 bp, 25=394 bp, 26=453 bp, 27=517 bp, 28=653 bp, 29=1033 bp, 30=1230 bp, 31=1766 bp, 32=2176 bp. All the fragments were separated in less than 30 minutes. Excellent separation performance was observed among the fragments with 434, 453 and 458 base pairs. The results also show that this matrix can be used to separate certain normal DNA samples from mutated samples, since fragments having identical lengths of 234 base pairs but having different nucleotide sequences (peaks 14 and 23) were well separated.

It should be noted that DNA fragments from standard Sanger reactions are different from the DNA fragments used in these experiments insofar as the Sanger fragments are denatured single-stranded and covalently tagged rather than double-stranded and intercalated with a fluorophore. Separations of Sanger sequencing reaction products are expected to be even more efficient because there will not be a distribution of conformations or fluorophore numbers per DNA fragment. The highly reproducible polymer matrices developed here for high-resolution separation of restriction fragment digests or PCR products should be of value for DNA typing as well as DNA sequencing.

Example II

High-Speed DNA Sequencing by using Mixed Poly (Ethyleneoxide) Solutions in Uncoated Capillary Columns Laser-induced fluorescence detection (LIF). The experimental setup was similar to that described in Example I, except that 1-mW He—Ne laser with 543.6-nm output from Melles Griot (Irvine, Calif.) was used for excitation. Two RG610 filters (Oriel Corp., Stratford, Conn.) were used to block scattered light.

Capillary and reagents. Capillaries were obtained and some were coated as described in Example I. All chemicals for preparing buffer solutions and for coating capillaries were purchased from ICN Biochemicals (Irvine, Calif.), except that acrylamide and formamide were from Sigma Chemical (St. Louis, Mo.) and poly(ethyleneoxide) was obtained from Aldrich Chemical (Milwaukee, Wis.). Fuming hydrochloric acid was obtained from Fisher (Fairlawn, N.J.). Polyacrylamide solution (10% solution in water, 700,000 to 1,000,000 $M_n$) was obtained from Polysciences (Warrington, Pa.). A calibration standard of PGEM/U DNA, prepared by cycle sequencing using commercial four-color terminators and Taq polymerase was obtained from Nucleic Acid Facilities (Iowa State University, Ames, Iowa).

Gel and buffer preparations. The 1× buffer solution was prepared by dissolving tris(hydroxymethyl)aminomethane (THAM), boric acid, ethylenediaminetetraacetic acid (EDTA) and urea in deionized water, producing a solution containing 89 mM THAM, 89 mM boric acid, 2 mM EDTA, and 3.5M urea, pH adjusted to 8.2.

The sieving matrix was prepared by gradually adding 1.5 g 8,000,000 $M_n$ poly(ethyleneoxide) (PEO) and 1.4 g 600,000 $M_n$ PEO in 100 ml buffer solution at 50°–60° C. During the addition of PEO, a magnetic stirring rod was used at a high setting to enhance the dissolution of the polymer powder. After the addition was complete, the solution was stirred for another 30 minutes. Then, the solution was degassed in an ultrasonic bath for 30 minutes.

Capillary wall treatment. A bare fused silica capillary (i.e., a capillary without any added internal coating), typically 45 cm total length (35 cm effective length) was flushed with methanol for 10 minutes and then 0.1N HCl for 2 hours, then filled with a very low-viscosity polymer solution (e.g., 0.5% PEO), then filled with the polymer matrix with a syringe. The filled capillary was equilibrated at the running voltage (12 kV) for 10 minutes before sample injection. The DNA sample was denatured by heating in a denaturing solution (5:1 formamide-50 mM aqueous EDTA solution) at 95° C. for 2.5 minutes, and the injection was performed at 6 kV for 12 seconds. Between runs, the used polymer matrix was flushed out of the capillary with high pressure (400 psi, 20×103 torr, 3 minutes), and rinsed with 0.1N HCl for 15–30 minutes before filling with new polymer matrix.

Base calling. Nucleotide identification in DNA sequencing experiments, i.e., "base calling", was performed using the ratio of emission intensities recorded through two different optical filters as described in Example V. Independent confirmation was accomplished by comparison with data obtained on a commercial DNA sequencer (Applied Biosystems, Inc., Foster City, Calif.).

Novel sieving medium. A direct comparison between PEO and 6% T non-crosslinked polyacrylamide was made. (In nomenclature commonly used in the art, T represents the percentage of total acrylamide, and C represents the percentage of cross-linker.) The test sample was a DNA (PGEM/U) fragment ladder prepared by the Iowa State University Nucleic Acid Facility using the standard dye-labeled terminators (Applied Biosystems, Inc., Foster City, Calif.) and Taq polymerase. The sample preparation procedure was not altered in any way from that used to produce samples for the commercial DNA sequencing instrument (Applied Biosystems, Inc., Foster City, Calif.). The injected sample was identical in concentration and composition to those suggested for loading into the commercial instrument. The matrix used for DNA sequencing consisted of 1.4% PEO 600,000 $M_n$, 1.5% PEO 8,000,000 $M_n$, 1× TBE (pH 8.2), 3.5M urea. Intermediate $M_n$ polymers (see Example I) were not needed; apparently the polymers at the two extremes of the size range can entangle in such a way to form the intermediate pore sizes as well. This binary matrix provided very similar performance to the 0.7% multiple polymer matrix (see Example I) but had even lower viscosity (1,200 centipoise at room temperature, measured in a capillary at 1 atm, 25° C., using the Pouiselle equation) than the 0.7% mixture. All experiments in this example were performed using this particular binary matrix.

Figure 13:
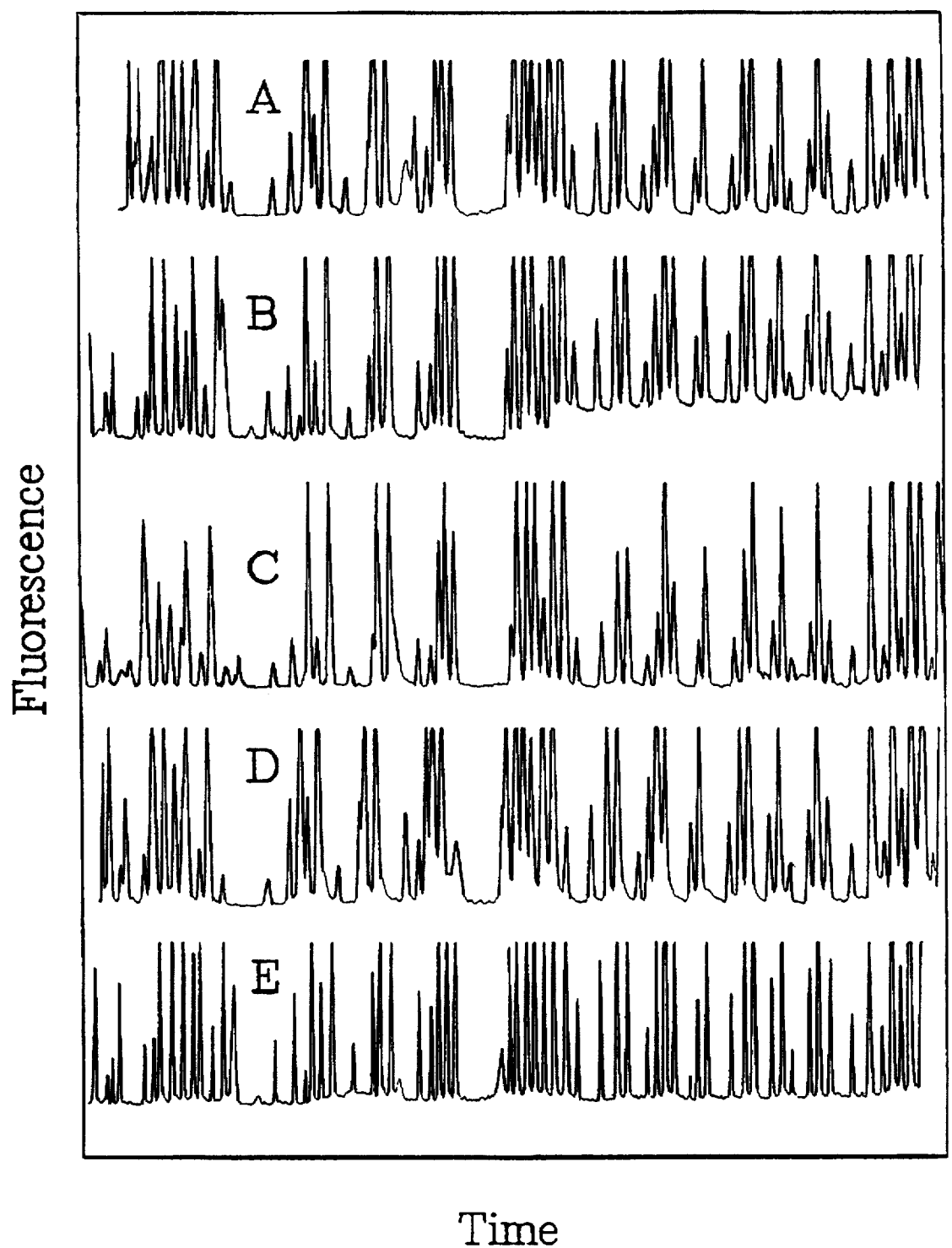
FIG. 13 shows electrophoretic separation of PGEM/U DNA fragments from the Sanger DNA sequencing reaction from base 28 to base 108.
Figure 14:
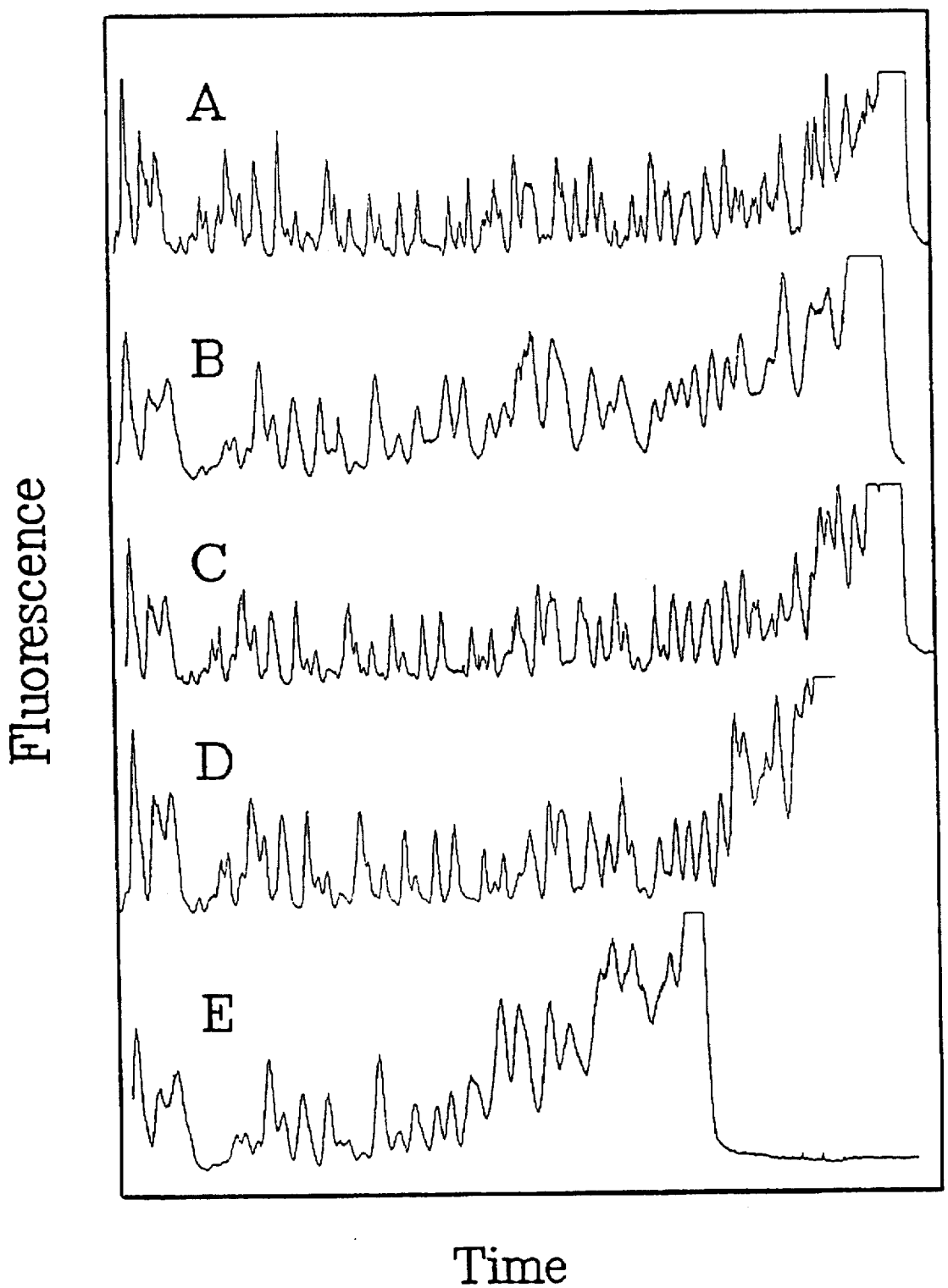
FIG. 14 shows electrophoretic separation of PGEM/U DNA fragments from the Sanger DNA sequencing reaction from base 420 upwards.

Commercial non-crosslinked polyacrylamide (10% T solution, 700,000 to 1,000,000 $M_n$) was diluted to form a 6% T, 1×TBE, 3.5M urea matrix. This solution had a measured viscosity of 4,900 centipoise at room temperature (measured as above). Otherwise, identical conditions were used throughout. Excitation by a He—Ne laser at 543 nm and 2 RG610 long-pass filters selected primarily the cytosine (C) and thymidine (T) fragments from the Sanger DNA sequencing reaction. Lyophilized DNA samples were denatured by heating in a 5:1 formamide-50 mM aqueous EDTA solution at 95° C. for 2 minutes. Electrokinetic injection was performed at 6 kV for 12 seconds and the separation was run at 13 kV. The results are shown in FIGS. 13 and 14 for the regions of 24–108 bp and greater than 420 bp DNA fragments, respectively. The time span of the abscissa is different in each of the panels. In FIG. 13 (covering DNA fragments between 24–108 base pair in length), panel A shows a PEO matrix in a coated capillary (14–19 minutes); panel B shows a polyacrylamide matrix in a coated capillary (37–55 minutes); panel C shows a PEO matrix in a fresh bare capillary (15–20.3 minutes); panel D shows a PEO matrix in an HCl-reconditioned bare capillary (6th run, 9.5–13 minutes); and panel E shows a polyacrylamide matrix in a bare capillary (2nd run, 14.5–26.5 minutes). In FIG. 14 (covering DNA fragments longer than 420 base pair in length), panel A shows a PEO matrix in coated capillary (39–52 minutes); panel B shows a polyacrylamide matrix in coated capillary (111–129 minutes); panel C shows a PEO matrix in fresh bare capillary (40–52 minutes); panel D shows a PEO matrix in an HCl-reconditioned bare capillary (6th run, 26–33 minutes); and panel E shows a polyacrylamide matrix in a bare capillary (2nd run, 60–69.5 minutes). The ordinate of each electropherogram was adjusted to roughly match the others and to emphasize the small peaks, as those cause the most problems in base calling due to overlap and inadequate signal to noise ratio (S/N). All peaks were on scale; they were merely truncated in the figures to allow plotting one on top of another. The abscissa of each electropherogram has also been adjusted to plot the same base-pair region in each case.

Comparison of panels A and B of FIG. 13 shows that for the short fragments, PEO provided a resolving power quite close to that of polyacrylamide. The major difference was separation speed. The PEO plot (panel A) was from 14 to 19 minutes while the polyacrylamide plot (panel B) was from 37 to 55 minutes. This is due to the higher viscosity of the polyacrylamide matrix. Very striking was the difference in separation for the large fragments, FIG. 14, panels A and B. The PEO matrix (panel A) clearly provided better resolution and may even be extending the convergence limit to longer fragments. In the middle range (108–420 bp, data not shown), there was a one-to-one correspondence between the resolution of DNA fragments in PEO compared to that in polyacrylamide, although some degradation was already evident in the polyacrylamide runs for DNA fragments longer than 320 bp.

A reasonable explanation for the differences in performance is that the maximum length of the polyacrylamide polymer is not sufficient to form dynamic pore sizes large enough for the large DNA fragments. In fact, a PEO molecule of the same Mn should be longer than polyacrylamide because of the specific atomic arrangement along the backbone. The same is true when PEO is compared with any other polymer that has been used for CE sieving. A polymeric material related to PEO is poly(ethyleneglycol) (PEG). Structurally, PEG is almost identical to PEO; but the starting monomer and the polymerization process are different. The latter is probably the main reason why commercial PEG preparations are not available out to the millions of daltons at which PEO can be purchased, and why PEG is not a suitable non-crosslinked matrix for capillary electrophoresis.

Column treatment protocol. Even when the sieving medium is replaced after every run to allow repeated usage of the capillaries, the protective coating (S. Hjertén, J. Chromatogr., 347, 191–198 (1985)) on the internal wall of the capillary gradually degrades. Attempts have been made to regenerate the coating after several runs by repolymerization of polyacrylamide in situ (S. Hjertén, J. Chromatogr., 347, 191–198 (1985)). However, original performance was not reproducibly restored in this manner. Other attempts have involved omitting the polyacrylamide coating in the first place (H. Swerdlow et al., Electrophoresis, 13, 475–483 (1992), M. Starita-Geribaldi et al., Electrophoresis, 14, 773–781 (1993)). For example, the silanol groups on the fused-silica wall can be irreversibly covalently modified by treating the capillary with 3-methacryloxypropyltrimethoxysilane (silanization) and the capillaries can be used without further polymerization with polyacrylamide. The electroosmotic flow was indeed substantially reduced using such capillaries, as judged by the migration times of the primer peak and the high MW convergence peak. However, the separation efficiency was compromised to the extent that sequencing of DNA fragments longer than 200 bp was not possible.

Because the main purpose of coating the capillary column is to eliminate electroosmotic flow (EOF), alternative approaches directed toward elimination of EOF were considered. To determine if DNA sequencing could be performed on a bare fused-silica column, i.e., whether the sieving polymer alone would effectively coat and isolate the capillary walls, commercial bare fused silica capillary columns were therefore washed with methanol and immediately thereafter, the polymer matrix was introduced into the bare capillaries and a DNA sequencing run was initiated.

DNA separations in bare capillary columns are shown in FIGS. 13, panel C (DNA fragments of 24–108 bp in length) and FIG. 14, panel C (greater than 420 bp in length) for the PEO mixed-polymer matrix. Comparison of panels A (coated capillaries) and panels C (uncoated capillaries) in FIGS. 13 and 14 reveal that there is practically no difference in the electropherograms with or without a coating on the capillary wall. Even the actual migration times are almost identical. This is the first demonstration of DNA sequencing in CE without a bonded coating on the column wall. Unfortunately, while these results can be reproduced for a new capillary column, the resolution invariably starts to degrade after one or two runs. The migration times became progressively longer and the peaks associated with the longest fragments became unrecognizable. Replacing the capillary array after every run is of course not a viable option for high-throughput DNA sequencing.

Thus, the column was flushed with deionized water, methanol, buffer solution, or 1M NaOH, plus combinations of these in an attempt to regenerate the surface characteristics of the column. In no case was the original performance restored, however. It was discovered, however, that the original column surface characteristics could be restored by flushing the column in between runs with acid (0.1N HCl).

The performance of a bare fused-silica CE column in separating DNA fragments after 6 cycles of PEO fill, DNA electrophoresis, pressure removal of PEO, and 0.1N HCl conditioning is shown in panels D of FIGS. 13 and 14 (showing separation of DNA fragments of 24–108 bp in length and greater than 420 bp in length, respectively). There is no obvious difference in resolution between this electropherogram and those for coated column/PEO (panels A of FIGS. 13 and 14) or for a fresh bare column/PEO (panels C of FIGS. 13 and 14). There are slight random variations in migration times, but no systematic change over time. Because no bonded coating was used, there was nothing to degrade. Thus, the column should in principle last indefinitely. This is the first demonstration of extended usage of a CE capillary for DNA sequencing.

A surprising result is that the migration times observed in the HCl-treated capillaries are much shorter than those found for any polymer matrix/surface preparation, either disclosed here or in the literature. The unexpected advantage to the use of HCl-treated, uncoated columns is that DNA fragments having lengths of 28–420 bp eluted within a time span of only 16 minutes for an average rate of 25 bp/minutes. This is faster by a factor of 3–5 compared to reported results using non-crosslinked polyacrylamide in coated capillaries.

Finally, the performance of a non-crosslinked polyacrylamide matrix in a bare fused-silica capillary was evaluated (panels E of FIGS. 13 and 14). Resolution for the short fragments (panel E, FIG. 13) is the best of all the systems studied here, but the resolution of fragments longer than 420 bp (panel E, FIG. 14)) is the worst. This electropherogram is actually the second run on the bare column, indicating that degradation is slower than for the case of the PEO matrix on a bare column. There was still gradual degradation due to an increase in electroosmotic flow, as the first run started 0.5 minutes earlier and ended 10 minutes earlier. This is consistent with the fact that polyacrylamide is a more viscous matrix, so it takes longer for the ions in the bulk medium to titrate the surface silanol groups to the same extent. The HCl reconditioning procedure was not effective after a column was filled with polyacrylamide.

System integration. In anticipation of the need to flush, recondition, and refill the capillary columns after each of many runs and the need to inject multiple samples separately into the array, a pressure cell suitable for these operations was developed. The pressure needed to fill a capillary with this relatively low-viscosity sieving matrix is only about 100–400 psi ($5 \times 10^2$–$20 \times 10^3$ torr), depending on the time allowed for each operation. The cell shown in FIG. 15 has been used for single-capillary operation in most of the experiments described above. For 100 capillaries in a bundle, the exit end can be gathered together to form a close-packed group only 2 mm in diameter. This can go through the same fitting as shown in FIG. 15 to implement the same recycling process. Pressure injection assists in avoiding cross contamination of the sample from the electrodes, and assists in avoiding the need to make electrical contacts with each sample vial in a large array entirely.

Example III

Optimization of Excitation and Detection Geometry for Multiplexed Capillary Array Electrophoresis of DNA Fragments Side-Entry Excitation. The schematic diagram of the experimental arrangement is shown in FIG. 1. An air-cooled argonion laser (Uniphase, San Jose, Calif., model 2213-150ML) operating simultaneously at several visible lines was used for excitation. The wavelength of the laser was chosen by an interference filter or a glass prism. When using a glass prism, the setup allows multiple-color excitation. The laser beam was focused by a 10-cm focal length lens (Edmund Scientific Co., Barrington, N.J.). The range over which the beam diameter remained smaller than 75 µm was 1.5 cm. This was confirmed by translating a photodiode (Hamamatsu Corp., Middlesex, N.J.) across the beam in conjunction with a 5-µm pinhole. The output of the photodiode was monitored by a digital multimeter (Keithley Instruments, Cleveland, Ohio). Two mirrors (Melles Griot, Irvine, Calif.) were used to adjust the direction of the laser beam to become parallel to the plane of the capillary array and to pass through the centers of the capillaries.

Fused-silica capillaries (Polymicro Technologies, Phoenix, Ariz., Model TSP075150, 75 µm i.d., 150 µm o.d., total length 50 cm, effective length 35 cm) were mounted by adhesive tape (3M water-proof SCOTCH Brand Tape, St. Paul, Minn.) on a polished aluminum surface in a close-pack configuration. The 1-cm detection windows were created by removing the external polyimide coating with boiling sulfuric acid. The capillaries were immersed in water in the liquid cell. A translational stage was used for fine adjustment of the position of the cell in order to place the focal point of the laser at the center of the array.

CCD detection system. The camera head (CH-220 thermoelectrically cooled/liquid-circulation heat dissipation, Photometrics TH7883-PM) was cooled to −40° C. It was mounted on top of the array, facing downward. There were 384×576 pixels, each being square with 23-µm edges. The camera electronics unit (CE-200) contained an analog-to-digital converter (ADC) providing 14 bits of precision, at a conversion gain that was software controllable.

The camera controller (CC-200) contained a 68000 processor, image-frame RAM (12 MB), firmware ROM, an IEEE-488 interface to a host personal computer, a "mouse" port, and interface circuitry for a video monitor (RS-170). The RS-170 subsystem and the mouse provided feedback to the experimenter during both equipment alignment and data acquisition. The capillary array in the detection region was imaged onto the CCD sensor through a 24-mm wide-angle lens (Canon, Tokyo, Japan, Model FD 24mm F1.4L, 50 mm diameter). Different sets of filters were placed in front of the lens in different experiments.

The software for CCD image data acquisition was obtained from Photometrics (Tucson, Ariz.). Data analysis was performed off-line, using software written in Turbo Basic (Borland)). During data acquisition, all images were stored in the cache memory, which were later transferred to the hard drive. The maximum image number was determined by the amount of RAM and the size of each frame. For 100 capillaries, by binning 3 consecutive pixels along each capillary, the pixel number for each frame was only 200.

Focus adjustment. To provide the most efficient imaging, each capillary was imaged to a width of 2 CCD pixels. With 75 µm i.d. and 150 µm o.d. capillaries tightly packed side-by-side in an array, alternate pixels traced out the liquid cores of the capillaries. The adjacent capillary walls, which represented useless information, were imaged onto the intervening pixels.

Achieving the best focus was simplified by the use of the RS-170 video monitor. A series of images were obtained and displayed on the video monitor to allow slight adjustments of the focus each time. For final adjustment, two bare columns filled with $10^{-10}$M fluorescein were used on both sides of the array. The best achievable focus results in the least number of pixels and the strongest signal for each capillary.

Sensitivity test. The 488-nm laser line (about 25 mW) was selected by a glass prism for excitation. Five capillaries were packed side by side in the liquid side-entry cell. The running buffer was 10 mM phosphate at pH 9.5. Electrophoretic separation was conducted at −20 kV using a high voltage power supply (Spellman, Plainview, N.Y., Model UHR50PN50). Samples containing $9.0 \times 10^{-11}$M fluorescein were introduced by electrokinetic injection for 3 seconds. Two cut-off filters (Melles Griot, Model OG550) were used in front of the CCD camera to reject stray light. Data acquisition was initiated 1 minute after the start of electrophoresis.

Fluorescence detection of DNA size markers. The laser line at 514 nm (3 mW) was chosen to illuminate the analytes. A RG610 cutoff filter and a 630-nm interference filter (Oriel Corp., Stratford, Conn.) were used to reduce scattered light. Signals were detected by the CCD camera at the rate of 1 Hz with 0.8 second exposure time. Nine capillaries divided into 3 groups of 3 were lined up along the laser beam. The center 3 capillaries were at the beam waist of the laser (the focal point, i.e., the location on the beam with the narrowest diameter). The other two groups were at the edges, 0.75 cm each from the beam waist. The capillaries were coated as described in Example I. The total lengths of the capillaries were 50 cm and the effective lengths were 35 cm or 40 cm. Among each group, the capillary in the middle was made longer than the other two to produce a different set of migration times. The high-voltage power supply was operated at −10 kV.

The running buffer was 1×TBE (89 mM Tris., 89 mM boric acid, 2 mM EDTA) with 1 µg/ml of ethidium bromide (Sigma Chemical Co., St. Louis, Mo.). The polymer matrix was a solution of 0.6% each poly(ethyleneoxide) (PEO) of $M_n$, 300,000, 600,000, 1,000,000, 2,000,000, 5,000,000 and 8,000,000, respectively (individual polymer products obtained from Aldrich Chemical Co., Milwaukee, Wis.). A pBR 322 Hae III DNA restriction digest (Boehringer Mannheim Biochemicals, Indianapolis, Ind.) was diluted with deionized water and injected at 10 kV from the negative high voltage side for 3 seconds. Before injection, the capillaries were equilibrated at 10 kV for 10 minutes. After each run, the used polymer matrices were flushed from the capillaries. The capillaries were then filled with a fresh polymer solution.

Separation of DNA sequencing ladder. The 488-nm laser output at 10 mW was used for excitation. A 488-nm interference filter was used to eliminate the plasma lines. Two OG515m (Oriel Corp., Stratford, Conn.) cut-off filters were used to discriminate against the laser line. One capillary from the center group in the arrangement above was selected for the separation (−10 kV).

Buffer and polymer matrices were the same as above except 5M urea was added. DNA sequencing test samples (PGEM/U) were prepared from the Sanger reaction according to standard protocols (Applied Biosystems, Inc., Foster City Calif., DyeDeoxy Terminators and cycle sequencing with Taq polymerase) in the DNA Facility of Iowa State University (Ames, Iowa). A 1.7-µl denaturing solution (the ratio of EDTA to formamide=1:5) was added to the sample vial. This was immersed in a water bath (90°–100° C.) for 3 minutes to denature the DNA. The sample was injected at −3 kV for 12 seconds.

Results. In a sensitivity test of the system, the fluorescence signals from an injection of $9.0 \times 10^{-11}$M fluorescein into each capillary were easily detected. The detection limit was determined by extrapolation to be at the low picomole (pM) level. It was independently confirmed that the system response was linearly dependent on concentration in this range. Compared to results obtained using an earlier setup (K. Ueno et al., *Anal. Chem.*, 66, 1424 (1994)), there was at least 100× improvement. In the previous setup, the laser was distributed into a thin line to cover 100 capillaries. Taking into account the portions of the laser beam wasted on the spacer grooves and those falling outside the array, less than 0.5% of the laser power in that setup actually irradiated each capillary. In the setup used in this example, the laser sequentially passed through all the capillaries. Because of the low concentration of the DNA samples ($10^{-10}$M), even though dyes with very high absorption coefficients ($10^5$) were used as tags, the laser power after traversing one capillary was reduced by less than 0.0001%. Thus, the laser power available to each successive capillary does not decrease much due to absorption of the DNA samples in the preceding capillaries. This allows the use of lower power lasers, reducing the danger of photobleaching the target species.

An important concern here is light scattering and refraction by the cylindrical capillary walls. Immersing the capillaries in water, which roughly matches the refractive index of the capillaries (1.45), was discovered to be the solution to the light scattering and refraction problem. Electrophoretic separation of pBR 322 Hae III fragments (0.125 µg/ml) was accomplished using an argon-ion laser (514 nm, 3 mW) and electrokinetic injection (3 seconds at −10 kV). The digest contained fragments of sizes (in bp) 51, 57, 64, 80, 89, 104, 123, 124, 184, 192, 213, 234, 267, 434, 458, 504, 540 and 587. Refraction and scattering were greatly reduced compared to operation in air. Fairly even signals from all the capillaries were obtained. The variation in the detection limit obtained from the 3 groups spaced 0.7 cm apart (see FIG. 7) were within a factor of 2, which was not surprising due to the different spot-size of the laser at each location. Because the dimension of the capillary is at the micron level, maintaining the flatness of the array so that the laser can pass through the centers of the capillaries is important for producing uniform signal levels for the array. Even better match in the refractive index is possible by selecting the appropriate immersion fluid, but this was found to be unnecessary.

Cross-talk between the separation channels is another important issue, especially for a multiplexed detection system. Fluorescence light refracted from the walls of the adjacent capillaries causes cross-talk. After repeated experiments, it was found that cross-talk can be further reduced by this optical design and good alignment of capillaries. For example, if one capillary (150-µm o.d.) is focused down to the size of only one pixel of the CCD, cross-talk cannot be avoided. However, if the image size of one capillary covers 2 pixels so that the liquid core exactly matches one pixel, and the adjacent pixels are matched to capillary walls, no cross-talk is observed.

Electrophoretic separation of pBR 322 Hae III DNA fragments (0.05 µg/ml) was accomplished using an argon-ion laser (514 nm, 3 mW) and electrokinetic injection (3 seconds at −10 kV). Fluorescence was detected from 7 consecutive pixels spanning 3 consecutive capillaries. The liquid cores of the capillaries corresponded to the second, fourth and sixth pixel. The third pixel was shared by the first and second capillaries. The fifth pixel was shared by the second and third capillaries. Even though cross-talk was observed in these two pixels, the second, fourth and sixth pixels, which corresponded to the centers of the 3 capillaries, were completely free from cross-talk. The higher intensities of the peaks in these 3 pixels further confirmed that they represented the capillary centers. These results were accomplished by refractive index matching via immersion of the capillaries in water, combined with good focus and alignment for all the capillaries in the array.

Electrophoretic separation of PEGM/U DNA fragments from the Sanger sequencing reaction was accomplished using an argonion laser (488 nm, 10 mW) and electrokinetic injection (12 seconds at −3 kV). One capillary in the center group was monitored. The sample was prepared following the commercial protocol with Taq polymerase and dye-labeled terminators. The sample preparation procedure was not altered in any way from that used to produce samples for the commercial DNA sequencing instrument (Applied Biosystems, Inc., Foster City, Calif.). The injected sample was identical in concentration and composition to those suggested for loading into the commercial instrument. The excitation and emission wavelengths produced fluorescence signals primarily from the adenosine (A) and guanine (G) Sanger sequencing fragments. Less of the longer fragments were injected because of electrokinetic bias and inefficiencies in the polymerase reaction. The frame rate for data acquisition was 1 Hz (0.8 s exposure). The data rate was limited by the nonlinear reaction of the CCD shutter when the overhead time went down to 0.1 second. The time resolution was adequate for this particular DNA separation, as indicated by the shapes and spacings of the early-eluting peaks. For even faster separations, however, the data rate needs to be increased. With 0.8 second exposure, the sensitivity of the system was adequate for actual DNA sequencing runs. In fact, sensitivity was limited by background fluorescence from the polymer matrix and not from insufficient fluorescence intensity from the DNA fragments. It was confirmed that fragments can be separated and detected out to 450 bp in length with 0.5-second exposure times.

The data rate for the new generation of CCD, even in the high-sensitivity, slow-scan mode, can be down to the millisecond per frame level. So, the use of a CCD detector is feasible even when the separation speed is further increased. It was confirmed that the CCD shutter can be kept open during the entire separation while the frames are read out at constant intervals. Even with the relatively slow data-read rate (50 kHz), there was no observable smearing of the information as the charges are shifted down the CCD columns. For 100 capillaries (200 pixels), the total time for shifting an entire CCD column was only 4 milliseconds, which is short compared to the exposure time. The frame rate of the camera can thus be reduced to 0.6 seconds for 0.5-second exposure times. A drawback is that entire sub-arrays must be read from these older versions of CCD. When the setup is modified to allow two or more laser lines in excitation (K. Ueno et al., *Anal. Chem.*, 66, 1424 (1994)), it is more advantageous to use a CID detector as described in Example IV, which allows random access of the data, or to use the newer versions of CCD cameras that allow reading from isolated subarrays.

Example IV

Evaluation of the Potential of a Charge Injection Device for DNA Sequencing By Multiplexed Capillary Electrophoresis Materials and Methods. The array detector used was the SCM5000E scientific grade CID camera system (CID Technologies Inc., Liverpool, N.Y.). The system included a controller and a camera head. The camera head contained a 512H×512V imager which was installed in a dewar chamber to provide for cooling the camera with liquid nitrogen. The system can also be operated at ambient temperature. The system was connected to a 486 DX/33MHz host computer (Electra, Ames, Iowa). All commands and configuration parameters to operate the camera system were programmable from the host computer. The CID operation protocol was developed using the CIDTEC standard function libraries. These are libraries of subroutines provided with the CID. To develop the operating protocol, the appropriate subroutines were selected and joined together using a subroutine in C language using Microsoft Quick C 2.5 as the compiler.

A Nikon F/1.4 lens (Nikon 28-mm focal length wide-angle) was attached to the CID camera head. For different magnification factors, a Nikon extension tube was connected between the CID lens mount and the lens.

To operate the camera in the vertical direction, the head assembly was placed downward on a 9"×9"×1" aluminum plate. The lens mount and the lens protruded from underneath the plate through a cut hole. The aluminum plate was supported with four 1" diameter scaled bronze poles. Each pole can slide through a 1" diameter hole at the corner of the plate and can be tightened by a screw, so that the camera can be adjusted to the desired height. To make the camera more stable, the upper part of the dewar chamber was clamped between two pieces of half-circle aluminum plates. One of the half-circle plates was attached to two bronze poles which were fixed onto the main aluminum plate.

A U-shaped capillary holder was fixed on a translational stage which was attached to a magnetic stage. A capillary was placed horizontally across the U-shaped holder. One or more capillaries can be placed in parallel onto the holder. For separating the DNA samples, a capillary column was coated with polyacrylamide and filled with a matrix made from a mixture of poly(ethyleneoxide) (PEO) polymers, trisborate-EDTA (TBE) buffer solution and 5M urea. Detailed procedures for the preparation of polyacrylamide-coated capillaries, buffers and separation matrix are reported in Examples I and II. A 45 cm long, 360 μm o.d., and 75 μm i.d. capillary was used in this example. A 1-cm section of the polyimide coating was burned off using sulfuric acid 30 cm from the injection end to form a detection window. The capillary was filled with water and then with the polymer matrix under 400 psi pressure provided by a compressed nitrogen gas tank. Two 10-ml vials containing TBE buffer were put at both ends of the capillary. Samples were injected at −9 kV for 6 seconds. To run electrophoresis, −9 kV was applied at the injection end of the capillary with the other end grounded. After the capillary was filled with the polymer matrix but before a sample was injected, the capillary was pre-run for 10 minutes to stabilize the baseline. After each separation, the matrix was pushed out of the capillary by compressed $N_2$. The capillary was rinsed with water and filled with fresh matrix again for the next separation. The replacement procedure usually took about 20 minutes. To preserve the capillary while not in use overnight or over several days, the capillary was rinsed with water and blown dry.

Excitation was provided by the 488-nm line from an air-cooled argon-ion ($Ar^+$) laser (Uniphase, San Jose, Calif.). A 488-nm line filter was placed in front of the laser head to remove plasma emission. The laser line was focused onto the capillary with a 10-cm lens (Melles Griot) from the horizontal direction. The position of the camera was adjusted to a proper height so that the image of the inner bore of the capillary was totally focused onto one pixel on the CID imager, and image of the capillary side walls was focused onto the adjacent pixels in the row. A 515-nm long-pass glass filter with or without a short-pass interference filter at 540 nm was used to discriminate against scattered laser light.

Results. The purpose of this experiment was to evaluate the operation of a CID camera for use in highly multiplexed capillary electrophoresis for DNA sequencing. Therefore, only one capillary was used in this example; however, a 100-capillary array can be accomodated without further modification.

1. Hardware. In multiplexed capillary electrophoresis, in order to achieve the highest sampling rate and to skip over irrelevant pixels, only one row of pixels which contained the images of the illuminated windows of the capillary array was scanned. In this example, the capillary was clamped between two halves of a U-shaped holder for mechanical rigidity. Because there were no moving parts in the setup, after focusing, the image of each capillary was maintained on the same pixel throughout many cycles of manipulation, such as filling with the matrix, matrix replacement, and sample injection. By focusing each capillary onto a total of two pixels, the CID camera can accommodate up to 250 capillaries. Alternate pixels represent the capillary bore and the capillary walls, respectively. In this work, 75 μm i.d.× 360 μm o.d. capillaries were used for ease of handling. This does not affect the evaluation of the CID camera.

When a laser beam irradiates a capillary array, the illuminated path can be focused along an imager row or an imager column. The two orientations may result in different subarray readout rates. In CCDs, the readout rate was different if one directs an n×1 subarray along the parallel registers compared to the same subarray along the serial registers. To appreciate the difference in a CID camera, one needs to understand the subarray scanning sequence of the CID imager. When the camera begins to read a subarray, it first resets the horizontal (H) and vertical (V) scanners. The V-scanner slews to the first row in the subarray. The H-scanner then slews to the first column in the subarray. The whole row (line) was then read out. The V-scanner then did a line increment to slew to the second row in the subarray. The H-scanner was reset and again slews to the first column of the subarray. This loop was repeated until all of the pixels in the subarray was read. If the subarray was oriented along a column, the imager needs to go through n times of horizontal slewing, n times of H-scanner reset and n−1 times of line increment in order to read out all the pixels. Although the slew rate of the CID camera is as high as 5 MHz, the time spent in repeated slewing is not negligible when n is large and the n×1 subarray is not at the edge of the imager. For example, when the camera is operated at 9 kHz pixel rate, if a 400×1 subarray is located at the 250th column between the 51st row to the 450th row, the experimentally measured subarray readout time is 47 milliseconds for row orientation and 86 milliseconds for column orientation.

Even though it is slower than the row orientation, the column orientation is preferred in cases where spatial crosstalk in a CID imager is significant. This could occur where, for example, background fluorescence is substantially reduced from the levels reported in these experiments, as where the polymer matrix has been purified of fluorescent contaminants. Row-column cross-talk increases linearly with signal level while column-column cross-talk remains insignificant until the signal level approaches saturation. The row-column cross-talk in an unilluminated pixel was only 0.11% of the signal in the illuminated region even for the early model CID. In the current model CID system, spatial cross-talk, if any, is not found to interfere with the measurement of laser-induced fluorescence in the CE system.

It is because the SCM5000E CID system employs a pseudo-random scheme to achieve random access that led to such a subarray readout rate difference. In future models, truly random access mechanism will be implemented. The difference between the two orientations will then be eliminated.

2. Noise. For CID cameras, the limit of detection is determined by background fluctuations, integration time, duty cycle, read-noise, dark current and quantum yield at the specific wavelength range. Under different conditions, the predominant noise source is different. The CID is a noisy detector compared to the CCD. With single read, the read-noise is 250 electrons (e) while the read noise of a typical CCD is 5–10 e. Since read-noise decreases with the square-root of the number of reads, with 100 nondestructive readouts, the noise is reduced to 25 e, which is still higher than that of the CCD. However, this does not mean that one can obtain better limit of detection by using the CCD camera for a specific situation. In fact, other factors play more important roles in determining the limit of detection of LIF detection in multiplexed CE.

Baseline noise was plotted as a function of the number of nondestructive readouts. First, the camera was operated at liquid-$N_2$ temperature without exposure but with 1000 milliseconds integration time (dark count, 1 second integration). Because liquid-$N_2$ cooling basically eliminates dark current, the measured baseline noise was only read-noise, which decreased linearly with the square-root of the number of nondestructive readouts. The same measurements were then made at ambient temperature. The entire curve was raised by 2 units. When the nondestructive readout number increased, the contribution of dark noise increased due to the prolonged pixel dwell time. The curve reached a minimum after 36 nondestructive readouts and rose after 64 nondestructive readouts. This is why at ambient temperature, multiple nondestructive readouts are beneficial only within a limited range. On-column LIF detection for CE at room temperature with 20 mM sodium phosphate buffer was then measured (1 second integration). The exposure time was 1000 milliseconds and the camera was operated in the snapshot mode. When nondestructive readouts were fewer than 25, the baseline noise was dominated by read-noise. After that, the baseline noise was determined by background fluorescence and dark noise. The final experiment involved on-column LIF detection at ambient temperature in a polymer-matrix-filled capillary (0.45 second integration). The camera was operated with 450 milliseconds exposure time. With anything more than 4 nondestructive readouts, there was no further reduction in baseline noise as the nondestructive readout number increases. This means that background noise (matrix fluorescence) was comparable to the read-noise. So, for on-column LIF detection in DNA sequencing with polymer matrices, if one compares CID with CCD, the larger read-noise of the CID is no longer a major concern.

3. Sensitivity. CID cameras have high quantum yields over a wide spectral range. The typical quantum yield is higher than that of the best photomultiplier tubes (PMTs) and higher than or comparable to that of a typical CCD. Therefore, by cooling the camera to liquid nitrogen temperature to suppress dark current and by applying multiple nondestructive readouts to reduce read-noise, CIDs are expected to be at least as sensitive as PMTs and conventional CCDs.

The limit of detection of the camera at liquid nitrogen temperature for CE measurements was found to be $10^{-12}$M of fluorescein with 20 mW excitation. This was determined by injecting standard solutions of fluorescein (dissolved in buffer to avoid electrokinetic injection bias) electrokinetically at +12 kV for 4 seconds and running electrophoresis in a 2 mM phosphate buffer, pH 9.5, at +12 kV. The limit of detection was defined as the (extrapolated) concentration that produced S/N=2 (peak-to-peak) after verification that the signal was linearly dependent on concentration in that range. The camera ran in the snapshot mode with 1000 milliseconds integration time and 100 nondestructive readout. The pixel containing the image of the irradiated point of the capillary was read before and after an exposure. Then the charge was cleared. The net signal was the difference of the two readouts. The limit of detection was also measured at different laser excitation powers up to 20 mW, and was found to be inversely proportional to the laser power in this range.

The sensitivity of the CID camera was also tested when it was operated at ambient temperature. The camera was operated in the snapshot mode with 1000 milliseconds integration and single readout. The limit of detection was $10^{-11}$M of fluorescein estimated from the peak heights and the standard deviation of the baseline as described above. The baseline noise under this condition was 9.9 counts (gain=250), which was 10× higher than that for liquid-$N_2$ cooling and with 100 nondestructive readouts. Accordingly, the limit of detection degraded by a factor of 10 due to increased dark current.

4. Operation modes. For high-speed DNA separation, the sampling rate needs to be at least 2 Hz. Unlike in CCD where pixels are scanned by destructive readout, in CID, a separated charge-injection step is needed to clear the pixels. Therefore, the sampling rate of the CID is determined not only by its pixel-read rate, but also by the charge-injection speed.

To test the system, the camera was run at liquid-$N_2$ temperature in the snapshot mode with 1000 milliseconds integration time. Charge injection was carried out by applying 100 cycles of global injection. Unfortunately, due to insufficient charge-injection efficiency, the CE peaks and the baseline were distorted and quantitative information was lost. Even following 100 cycles of global charge injection with 20 cycles of subarray injection, the integrated charge was still incompletely cleared. It has been suggested by the manufacturer that 800 millisecond continuous global injection be applied in order to achieve complete charge injection. Such a delay is impractical for operating the camera at a reasonable sampling rate for CE.

Alternatively, one can keep integrating the signal without clearing the charge. The continuously integrated signal is read at the desired sampling rate. The actual integrated signal during each frame period is obtained by difference. When the overall signal approaches either digitization or pixel-well saturation, the charge is cleared and the cycle is repeated. In this mode, charge-injection need not be complete because the signal for each frame is based on a difference. However, there are disadvantages to operating the CID camera in this manner. First, because the absolute standard deviation of repeated measurement of the same signal is proportional to the signal level, the noise level in different parts of the reconstructed electropherogram will be different. Second, because the signal for each frame is the calculated difference of two readouts, the read noise is increased by a factor of the square-root of 2. Third, in a case such as DNA sequencing, there are hundreds of peaks in each run and the temporal spacing between adjacent peaks is very short. There is also a large background signal from the polymer matrix. So, after only a few peaks, the accumulated charge needs to be cleared. Because each charge-injection cycle needs an additional readout, such an operation decreases the duty cycle.

An asynchronous scanning mode may be used to overcome the above limitation. For example, to read a 400×1 subarray at 9 kHz pixel-read rate, if each pixel needs to be read 9 times per frame, the total readout time will be 400 milliseconds. With a frame rate of 2 Hz in the snapshot mode, the exposure duty cycle is only 20%. If one keeps the shutter open all the time and keeps scanning the subarray continuously without waiting between two frame readouts, the actual exposure time will be 399 milliseconds or an exposure duty cycle of 99.75%. The 400 pixels are exposed and read at different times, i.e., asynchronously. Although the same principle can also be applied to the CCD, when the subarray is nxm (n>1, m>1), blurring may occur in the CCD because the charge in a pixel is shifted and not confined within a fixed location like a CID.

To clear the charge for each frame, one needs to apply subarray charge injection. The charge in each pixel is cleared individually during each frame without disturbing the other pixels. It took more than 3.5 milliseconds to clear the charge in a pixel completely by subarray charge injection. Although the exposure duty cycle can still be above 99% for a 400×1 subarray, the frame rate cannot be higher than 0.65 Hz, which is marginal for high speed DNA sequencing.

Fortunately, charge injection was more efficient at ambient temperature than at liquid-$N_2$ temperature. At ambient temperature, 100 cycles of global injection, which takes only 2.8 milliseconds, can completely clear all levels of integrated charge.

Dark noise of the CID is generally lower than that of the CCD because of the difference in pixel structure of the two kinds of imagers. The dark noise of the CID is not serious even at ambient temperature. With 1000 millisecond integration per frame, the dark noise was 2.0 to 2.6 counts (gain=250). With 10 second integration per frame, the dark noise was 8.1 to 8.3 counts (gain=250), which is still lower than the single-read noise. It took about 40 seconds for dark current to saturate the digitization scale (gain=250). Therefore, if the CID is operated at ambient temperature, dark current is not the major source of noise for the case of matrix-filled capillaries, where background fluorescence is significant.

After optimization, the operation sequence as shown in Table 1 was established for a gain setting of 250. The time for each step was also measured. The subarray configuration was set by assuming a two-channel system as in K. Ueno et al., *Anal. Chem.*, 66, 1424 (1994). The scheme of two 200×1 subarrays was for a 100-capillary array. The scheme of two 500×1 subarrays was for a 250-capillary array. Because the CID has 512×512 pixels, as many as 256 capillaries can be set up by focusing each capillary onto two pixels.

TABLE I

Sequence of CID operation for LIF detection in multiplexed capillary array

| Operation step | Timing for each step | |
|---|---|---|
| | 100 array | 250 array |
| Global charge injection | 3 ms | 3 ms |
| Exposure | 448 ms | 384 ms |
| Read subarray A | 23 ms | 58 ms |
| Transfer data to XMS | 3 ms | 5 ms |
| Read subarray B | 23 ms | 58 ms |

TABLE I-continued

Sequence of CID operation for LIF detection in multiplexed capillary array

| Operation step | Timing for each step | |
|---|---|---|
| | 100 array | 250 array |
| Transfer data to XMS | 3 ms | 5 ms |
| Repeat above steps | 500 ms/frame | 500 ms/frame |
| Transfer data from XMS to hard disk after run | 5 min for 7200 frames | 10 min for 7200 frames |
| Duty cycle for the first pixel in subarray A | 90% | 77% |
| Duty cycle for the last pixel in subarray B | 99% | 99% |

In the axial direction of the capillaries, if the fluorescence images cover more than one pixel each, there is no need to read all these pixels and combine the intensities because the measurement is background-noise limited. For the same reason, if one uses a CCD for detection, there is no need to bin several pixels. Binning unilluminated or less intense pixels with the most intense pixel in fact decreases S/N because the total dark current is increased.

In standard CCDs, if two separated lines (n×1 subarrays) need to be read, the pixels between these two lines also need to be read. This tremendously increases the number of pixels to be read and thus the volume of data to handle. The further apart the two lines are, the more pixels need to be read. In contrast, in CID, only the subarrays or pixels containing useful information are selectively read. If the two laser lines need to be located far from each other for optimal optical coupling, the sampling rate is not affected because the number of pixels to be read does not change.

5. Timing of CID operation. The SCM5000E CID system can run with a pixel-read rate of 8.8 kHz to 100 kHz, which corresponds to a gain of 255 to 0. Gain defines the digitization sensitivity of the camera. At different read rates, the pixels require the same amount of light to saturate. In other words, the same amount of light produces the same number of charge carriers in a pixel independent of digitization gain. But the digitization sensitivity for this amount of charge carriers is different at different read rates. The faster the camera reads, the less sensitive is the digitization process. In addition, read-noise increases rapidly when the camera reads faster than 33 kHz. Below 33 kHz, the read-noise is relatively constant. As shown in Table 1, the readout time was short compared to exposure time even when the camera was reading at the slowest rate. Therefore, the camera was operated at 9 kHz, which is selected by setting the gain to 250, so that the digitization sensitivity is maintained at the highest level available.

In the operation sequence shown in Table 1, the exposure duty cycle for each pixel was different because their actual exposure times were slightly different. For the first pixel in the first subarray, the duty cycle was 90% because the exposure time for this pixel was only 448 milliseconds. For the nth pixel to be read, it gained an extra (n−1)*110 microsecond exposure time while the camera reads the first (n−1) pixels. For the last pixel, the actual exposure time was 494 milliseconds and the duty cycle was 99%. The result indicates that it is advantageous to keep the shutter open. If the camera operates at 10-Hz frame rate, the duty cycles for the first pixel and the last pixel to be read are 55% and 95%, respectively, which are excellent taking into account the very fast sampling rate.

The flexible reading mode of CID has additional advantages. If the light intensity is higher at one side of the capillary array than at the other side due to absorption or light scattering, the corresponding subarray can be scanned from the side where the light intensity is higher so that S/N is more even across the capillary array. If the capillary array is illuminated by a Gaussian-shaped light profile, the fluorescence from the center of the capillary array may saturate the middle pixels before the pixels on the sides have accumulated sufficient charge. To accommodate this, the middle pixels can be read with shorter integration times and the pixels on the sides can be read after longer integration times.

A side-by-side comparison of electrophoretic separations of DNA fragments from a Sanger reaction following (a) the optimized sequence of CID operation, as shown in Table I, column I and (b) using a commercial DNA sequencing instrument (Applied Biosystems, Inc., Foster City, Calif.), was made. The test sample was the set of DNA fragment ladder (PGEM/U DNA) prepared by the Iowa State University Nucleic Acid Facility using the standard dye-labeled terminators (Applied Biosystems, Inc., Foster City, Calif.) and Taq polymerase. A 515-nm long-pass filter was used in fluorescence detection. The sample preparation procedure was not altered in any way from that used to produce samples for the commercial DNA sequencing instrument (Applied Biosystems, Inc., Foster City, Calif.). The injected sample was identical in concentration and composition to those suggested for loading into the commercial instrument. The test sample was independently analyzed (sequenced on the commercial instrument) and was found to be well-behaved. The sensitivity and temporal resolution of the optimized sequence of CID operation (Table 1) was found to be clearly sufficient for DNA sequencing applications.

6. Exposure-time gradient. In DNA separation by CE, different sizes of fragments migrate at different velocities. Their residence times at the detection window are different. The larger fragments elute later and stay at the detection window longer. In addition, peaks of the larger fragments become broader because of a loss in separation efficiency. If the camera runs at the same frame rate throughout, the peaks of the larger fragments contain more data points than those of the shorter fragments. However, if the camera runs at a slower frame rate to monitor a larger fragment, the total fluorescence from that fragment can be concentrated into fewer sampling points. This is analogous to changing the shift rate to fit the migration velocity in the time-delay integration mode. The S/N will thus be improved. This is very useful because the larger fragments in a DNA sequencing sample are typically at lower concentrations than the shorter fragments due to the nature of the polymerase reaction. In addition, the peak intensity of a fragment is inversely proportional to its migration time due to electrokinetic injection bias. With the flexibility of the user programmable features of the CID, the exposure time can be changed dynamically during electrophoresis to account for the migration velocity differences of the DNA fragments.

Figure 16A:
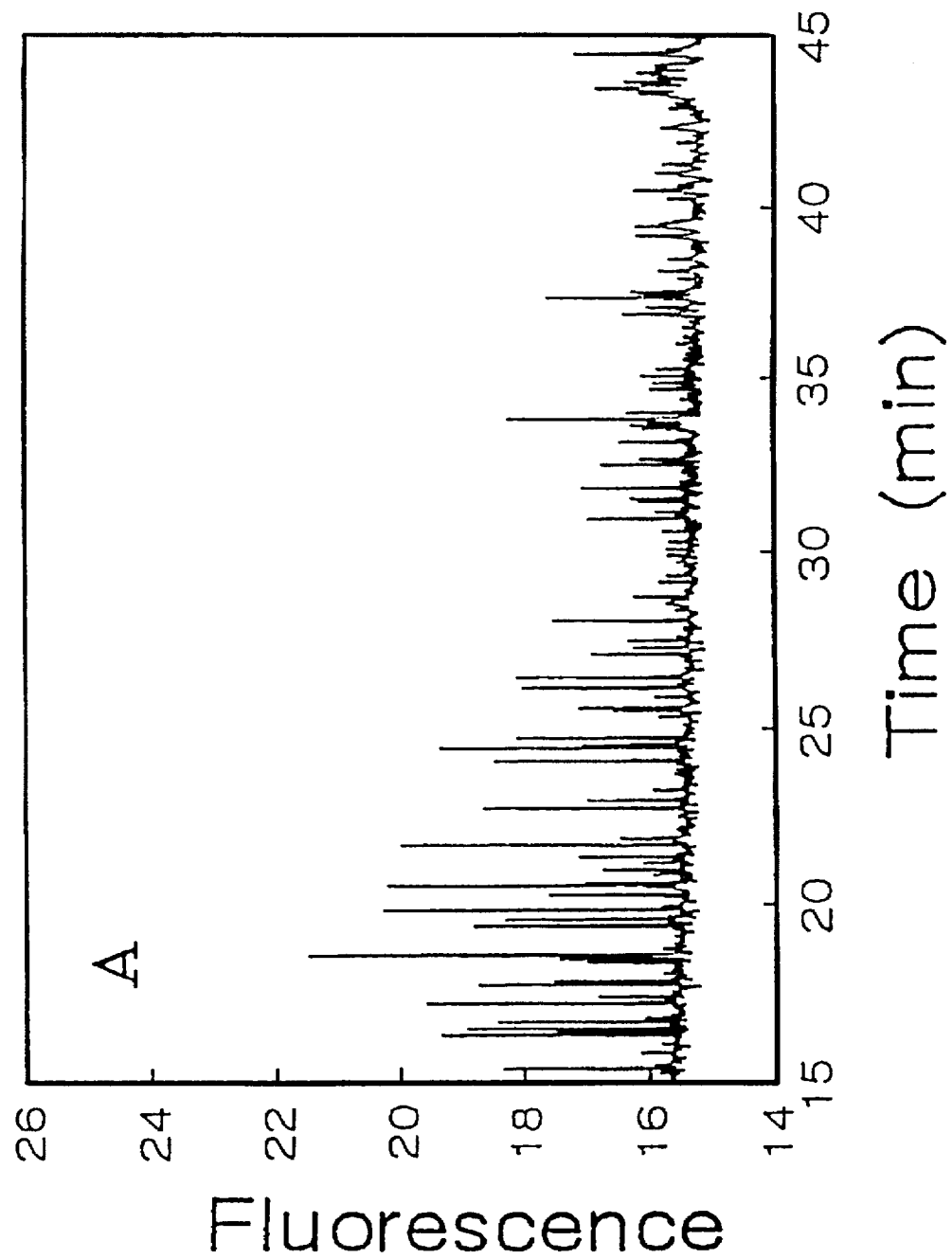
FIG. 16A shows CID detection of DNA fragments after a Sanger DNA sequencing reaction without using an exposure-time gradient.
Figure 16B:
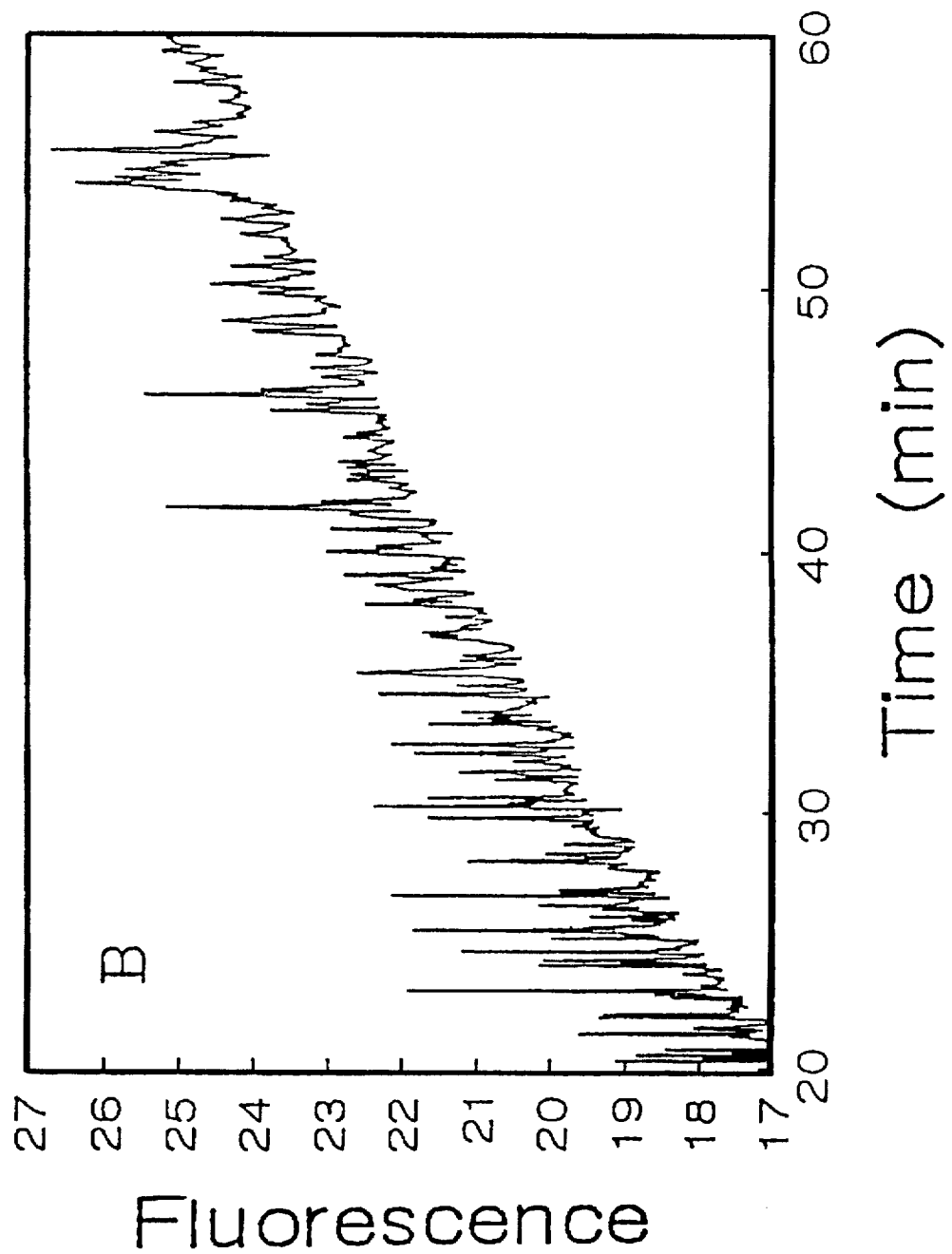
FIG. 16B shows CID detection of DNA fragments after a Sanger DNA sequencing reaction using an exposure-time gradient.

The exposure time can be programmed to as fine as several microseconds. In these applications, a linear exposure-time gradient was adequate. To achieve a finer gradient, the relation between exposure time and migration time can be fit to a numerical function derived from experimental data, and adjust the exposure time according to the fitted function in real time. To demonstrate this, the same separation of DNA sequencing fragments was monitored through a band-pass filter to reduce the number of peaks and to reduce the signal levels. It is clear that the S/N was improved for the large fragments after implementing exposure-time gradient (FIGS. 16A and 16B). A 515-nm long-pass plus a 540-nm short-pass filter were used in fluorescence monitoring to deliberately reduce the number of peaks and decrease the S/N. Although, there is a sloping baseline in FIG. 8B, because the background is also integrated for progressively longer periods, this can be easily corrected after the run.

7. Data manipulation. There are several ways to save and process the pixel data from a camera. The data during the run can be stored in RAM or onto the hard disk of the host computer. To store in RAM, the data size of each frame should be small. Otherwise the installable extended memory of a typical desktop computer will not be enough to store the data of a complete run. The speed advantage of storing data during the run in RAM is obvious. Also, the computer does not have to re-read the large number of image files of thousands of frames from a hard disk in order to convert the image files into corresponding electropherograms during post-run data processing, which takes hours of computer time.

The data size generated in each run using a CID is small. For a 1-hour run at 2-Hz frame rate in a 100 capillary array with two detection channels, only 1.44 MB data is generated. If one uses the multiple-wavelength fluorescence detection system (dispersing the fluorescence over 100 pixels and compressing 10:1 by binning) for a 100 capillary array, the number of pixels to be stored per frame will be 2000, and the volume of data generated will be 14.4 MB. When the CID camera reads a subarray, pixel data is transferred to the base memory or extended memory of the host computer. For a two-color 100-capillary array, only 400 pixels are to be read. For a desktop computer with 16 MB extended memory available, 20000 frames can be stored as integer numbers. If the camera is operated at a 2-Hz framerate, this is equivalent to 2.7 hours, longer than typical CE sequencing runs. For a 250 capillary array, the maximum available run time will be 1.1 hours. Even this is close to the estimated 1.5 hours required to read 500 bases in DNA sequencing using capillary electrophoresis in linear polyacrylamide. By using exposure-time gradient, the number of data points will be further reduced to allow 1.5-hours of data to be comfortably stored in 16 MB. Also, the image of one capillary occupies two pixels, with the centers of two adjacent capillaries being focused onto alternating pixels. The pixel between these two pixels corresponds to the capillary walls and contains useless information. The data size can therefore be further reduced by 50% by skipping over the void pixels. Finally, up to 64 MB can be allocated for data storage in a desktop computer. Therefore, the present system can be easily adapted to several hundred or a thousand capillaries in an array.

In this system, pixel data for a frame is first transferred to the base memory of the host computer. If multiple nondestructive readouts are applied, the average intensity for each pixel is calculated and only the averaged pixel data is saved. After electrophoresis is complete, the electropherogram for each capillary is built up by directly reading the intensities of the corresponding pixel in all of the frames from the extended memory. The reorganized data for all of the capillaries are then saved to hard disk in binary format, which can be directly processed with standard chromatography software such as ChromPerfect (Justice Innovations, Palo Alto, Calif.). Alternatively, one can use built-in peak-finding algorithms to integrate the peaks while the data is still in memory in order to save data processing time.

By using two spatially separated excitation laser beams, the labeled DNA fragments can be excited twice to achieve two-channel, twocolor base calling without the need to split the image. However, the appearance time of the same DNA fragment at the two channels is different. Thus, it is necessary to convert the time scale of one channel to match that of the other channel in order to do base calling. For the case in which the frame rate does not change, time-scale correction can be accomplished simply by multiplying the time scale of the first channel by the ratio of the effective length at the second channel to that at the first channel. After time-scale correction, the migration time of a peak in the two channels can be matched accurately. With exposure-time gradient, time-scale correlation for the two channels becomes more complicated but entirely tractable with the proper conversion algorithm. The important condition for accurate correlation of the time scales of the two channels is to keep the whole capillary at the same temperature and to make sure that the coating and the polymer matrix in the capillary is uniform, because time-scale correction is based on the assumption that a DNA fragment migrates along a capillary with constant velocity.

Example V

Two-Color Base Calling Schemes for DNA Sequencing Based on Standard Four-Label Sanger Chemistry Set forth below is a scheme for use in nucleotide identification in DNA sequencing, i.e., "base calling", that is elegant and highly accurate, independent of concentration (incorporation rate for the polymerase), useful even for very poorly resolved peaks (potentially permitting extension of base calling to larger fragments and/or sacrificing some resolution for speed in the separation), requires minimal computation (improving speed and decreasing effort for data processing), and is compatible with the high light-throughput optics for excitation/emission described elsewhere herein.

Separation. Fused-silica capillaries 45–60 cm long with 75 µm i.d., 150 µm or 360 µm o.d. (Polymicro Technologies, Inc., Phoenix, Ariz.) were used for separation. The inner wall of the capillary was coated with polyacrylamide or treated with 0.1M HCl as described in Examples I and II. The sieving matrix was prepared by dissolving 1.5% of 8,000,000 $M_n$ poly(ethyleneoxide) (PEO) and 1.4% of 600,000 $M_n$ PEO in running buffer, which was 1× TBE with 3.5M urea. DNA sequencing samples (PGEM/U) were prepared from the Sanger reaction according to standard protocols (Applied Biosystems, Inc., Foster City, Calif., DyeDeoxy Terminators and cycle sequencing with Taq polymerase) in the DNA Facility of Iowa State University. Capillaries were filled using a 5-ml syringe (Becton Dickinson & Co., Franklin Lakes, N.J.) for 10–15 minutes by applying pressure at the syringe with a metal clamp. After a run was completed, the matrix was pushed out with compressed $N_2$ gas at 300 psi (15×10$^3$ torr) (within 2 minutes) or with a 100-µl syringe (Hamilton Company, Reno, Nev.) (within 30 seconds). Before flushing, the TEFLON tubing which was used to connect the capillary to the pressure devices was first filled with water so that the capillary would not become clogged by dried particles. Two 20-ml glass sample vials containing the running buffer were used as buffer reservoirs. The matrix-filled capillary was prerun for 10 minutes before injection. Injection was at −9 kV to −12 kV for 20 seconds or 15 seconds, depending upon the length of the capillary. Electrophoresis was run by applying −9 kV to −15 kV at the injection end via a high-voltage power supply (Spellman, Plainview, N.Y.).

Experimental setup. The overall setup was similar to that described in Example IV but with a different capillary mount and new spatial arrangement of optical filters to accommodate either two-beam excitation or one-beam excitation. A capillary was mounted on an aluminum block of 1.6 cm (W)×6.0 cm (L)×6.5 cm (H). Two 0.3-cm wide, 3-cm deep grooves were cut across the width the mount to form two optical channels. The deep grooves helped to reduce background noise from scattered light. The two channels were placed 0.9 cm apart to reduce interference of scattered light between the two detection channels when the two-wavelength, two-beam excitation scheme was employed. The capillary was placed flat on the mount across the grooves and taped tight to it (Scotch tape, 3M, St. Paul, Minn.). The CID camera was set up above the capillary mount so that the capillary was oriented along the CID imager columns as described in Example IV. The mount was wide enough to accommodate as many as 100 capillaries with 150 μm o.d.

An air-cooled Ar$^+$laser (Uniphase, San Jose, Calif., Model 2213–150ML) with multi-line emission was used for excitation. The 488-nm and 514-nm lines were separated with a glass prism. For two-wavelength, two-beam excitation, two 0.5-cm detection windows 1.2 cm apart were formed on the capillary by burning off the coating with boiling sulfuric acid. The detection windows were placed at the detection channels aligned with the grooves on the aluminum mount. The 488-nm beam and 514-nm beam were focused with 10-cm focal length lenses (Oriel, Stratford, Conn.) from the same side of the capillary mount. The edges of the two lenses were trimmed off to allow placing them side by side with the centers of the lenses in the light paths. The laser beams were perpendicular to the capillary and the CID camera. A 5 cm×8 cm×2 mm quartz plate was placed 4 mm horizontally above the capillary. On the quartz plate, a 600-nm high precision interference long pass filter (Ealing Electro-optics, South Natick, Mass.) and a RG610 glass filter (Schott Glass, Duryea, Pa.) was placed on top of the 514-nm excitation channel. A 0.5-inch diameter 488-nm Raman-edge filter (Physical Optics, Torrance, Calif.) was placed on top of the 488-nm excitation channel.

For one-wavelength, two-beam excitation, the 488-nm beam was split into two with a beam splitter (Melles Griot, Irvine, Calif.) to illuminate both detection windows. Beam focusing and filter setting were the same as that in the two-wavelength, two-beam excitation scheme.

For one-wavelength, one-beam excitation, only one 488-nm beam was focused onto the capillary. The image of the illuminated region was split into two by a tilted glass plate or an optical filter (FIG. 9). To set up this system, the relative positions of the CID camera and the capillary were first aligned so that the image of the detection window could be focused onto the center part of the imager. A 63-mm diameter 488-nm Raman-edge filter (Kaiser Optical Systems, Ann Arbor, Mich., Model Notch-Plus) was attached onto the camera lens (Nikon 28/1.4 AFD, filter size 72 mm). A 5 cm×5 cm×3 mm RG610 filter (Schott Glass) was tilted at 30° relative to the focal plane of the camera. With the top edge of the RG610 filter parallel to the laser beam and facing toward the center of the field of view, the filter was translated until the top edge of the filter passed about 0.5 cm beyond the detection window. Light originating from the half of the field of view which was covered by the filter (red channel) was thus shifted toward the side of the filter. Emission was thus focused as one image which was 9 CID imager rows away from the original image. Light originating from the other half of the field of view (blue channel) was focused as before. The distance between the two images can be changed by adjusting the tilt angle of the RG610 filter.

The RG610 filter served the dual purposes of image displacer and optical filter. The RG610 filter also blocked the strongest scattered laser light, which forms a fan perpendicular to the capillary array. This is very important in reducing scattered light background at the blue channel. Although the scattered laser light hitting the RG610 filter produced some fluorescence, the fluorescing part of the RG610 filter was out of focus and did not cause significant background in the image area in the CID detector. For critical focusing, the difference in effective optical pathlengths for the light in the two halves of the field of view can be compensated with a quartz plate. The quartz plate can be tilted at the same angle as the RG610 filter and covers the other half of the field of view in the same way as the RG610 filter.

CID operation was described in Example IV. Data analysis is carried out by using a chromatographic software package known as "CP" (ChromPerfect, Justice Innovations, Palo Alto, Calif.) and QuattroPro for DOS (Borland, Scotts Valley, Calif.).

Peak-height ratios. The spectral properties of the four standard dye labels (FAM, JOE, ROX and TAMRA, ABD Division of Perkin Elmer, Foster City, Calif.) for the Sanger reaction were distinguished with a peak-height ratio coding method when two long-pass filters were used for the two spectral channels. For one capillary, two electropherograms were generated, each corresponding to one spectral channel. Integration results from standard chromatographic software were saved in ASCII files. Only migration times and peak heights were imported into a worksheet for base calling. Migration time was used as the index to match the peaks of the same base at the two spectral channels.

Different combinations of filters were examined for their abilities to discriminate the 4 labels. The Raman-edge filter let through more light (which is always desirable) and discriminated better between adenosine (A) and guanine (G) DNA fragments compared to a 515-nm long-pass cutoff filter. On the other hand, a 610-nm long-pass cutoff filter discriminated better between cytosine (C) and (T) DNA fragments compared to a 600-nm filter and was chosen even though the latter let through more light. The best combination turned out to be the 488-nm Raman-edge (RE) filter and RG610 filter. Both filters allowed all bases to be detected at both spectral channels. The peak-height ratio was thus calculated for all bases. The major advantage of using long-pass filters is that optical throughput is maximized. This is important because the detection limit determines how far one can read the bases in a given sequencing run.

Figure 17:
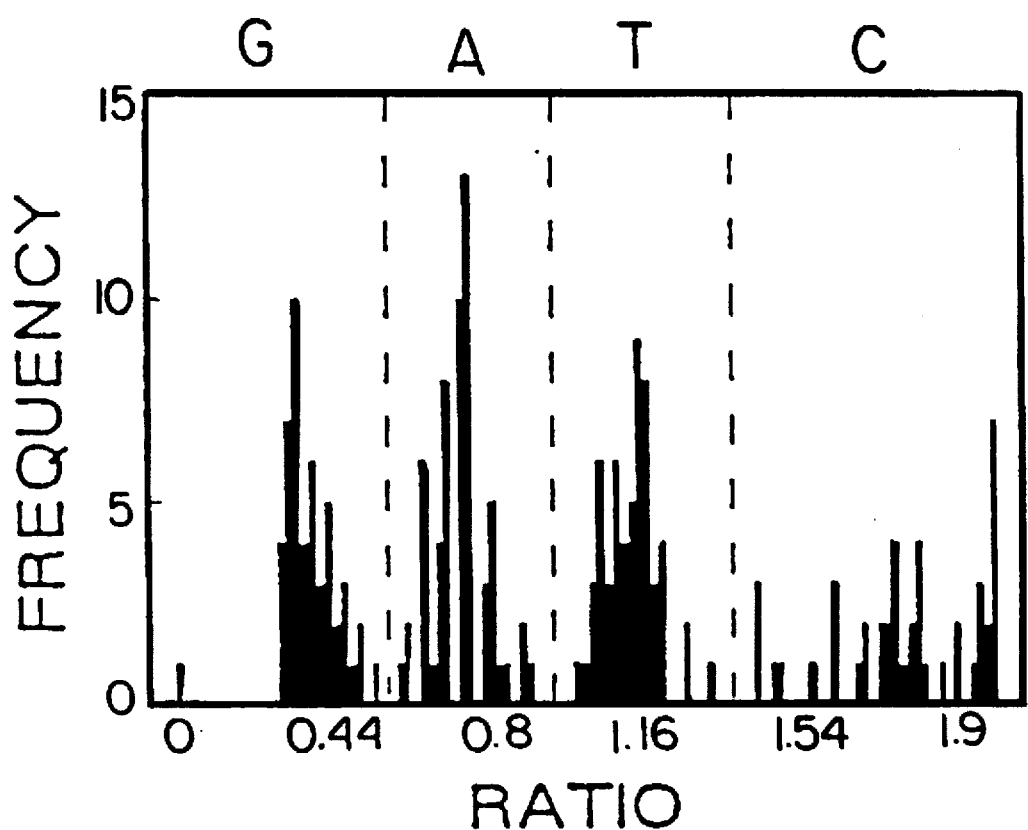
FIG. 17 is a histogram depicting clustering of peak-height ratios for the four dye labels in a Sanger DNA sequencing experiment.
Figure 18:
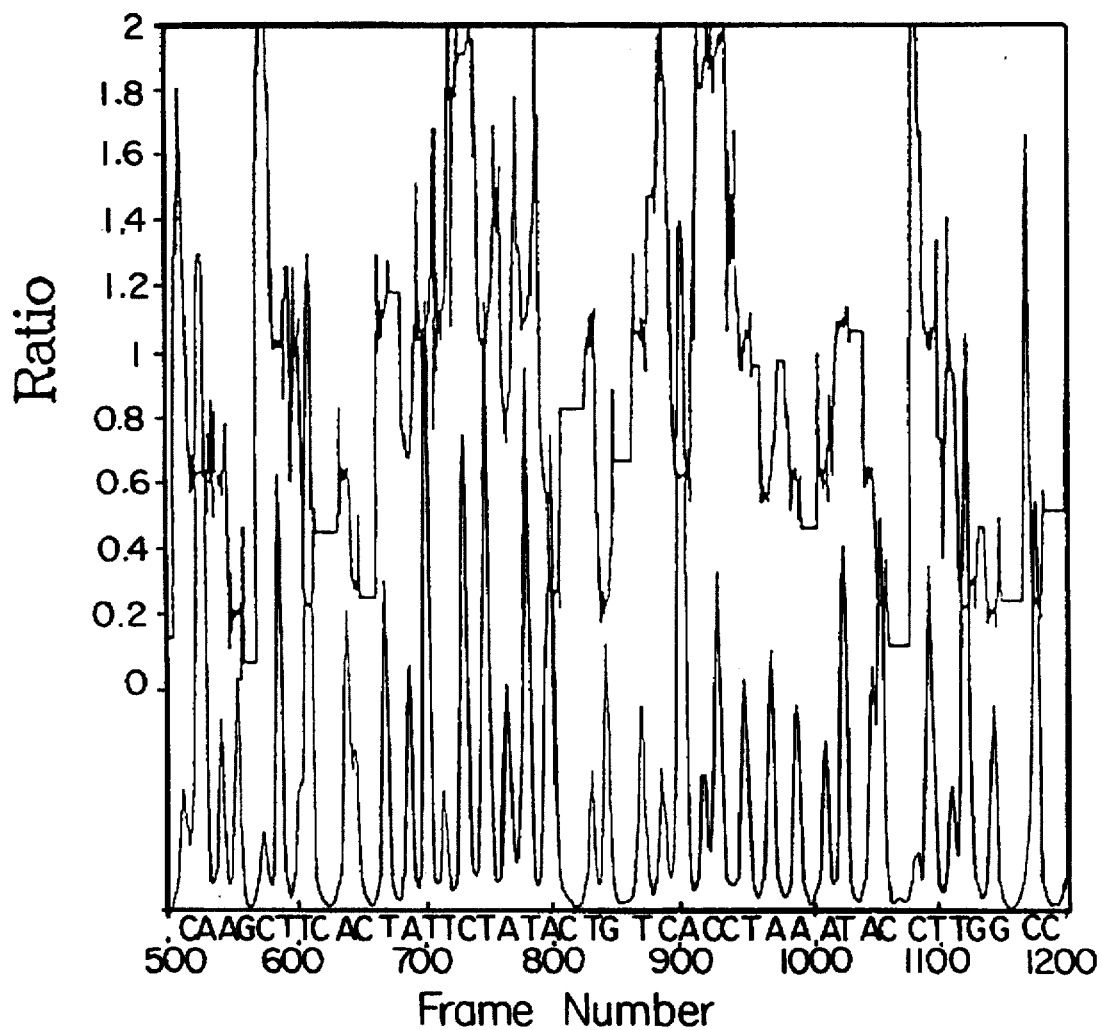
FIG. 18 shows a ratiogram (top, heavy line) used for base calling (i.e., nucleotide sequence identification) in a DNA sequencing analysis.

A histogram was built from the peak-height ratios. In order to establish the criteria to call bases (i.e., determine the nucleotides represented by the DNA fragments produced in a DNA sequencing experiment) with good certainty, only the peaks within good separation resolution range were used in the calibration step. Peaks within 250 bp length met this requirement. The peaks fell into four distinct clusters (FIG. 17). Dashed lines were demarcation points for nucleotide base identification (base calling). The excitation wavelength used was 488-nm, and fluorescence emission was detected using 610-nm vs. 515-nm long-pass filters. Three ratios were determined from the locations of the gaps between the four clusters, namely $R_1$, $R_2$, $R_3$. A formula was set in the spreadsheet to call all the bases automatically with $G<R_1$, $R_1<A<R_2$, $R_2<T<R_3$, and $R_3<C$. Standard deviations of the peak-height ratios were calculated for all of the same kind of bases within the readable base-pair range. The boundaries of the four clusters, i.e., $R_1$, $R_2$, $R_3$, were thus defined with certainty at least as high as 99.7% (±3σ). As long as the optical setup does not change, the base calling criteria, which is simply the $R_1$, $R_2$, $R_3$ values, will not change. A series of unknown DNA samples can then be sequenced in the calibrated system up to the readable length.

When an electropherogram is analyzed with the CP software package, integration starts at the very front edge of the first peak and ends at the trailing edge of the last peak. In this case, CP determined the correct baseline in the entire range without the need for manual intervention. The rising baseline due to exposure time gradient did not affect the ability of CP to choose the proper baseline. But CP did not detect all of the peaks automatically, missing some partially resolved peaks (R<1.0). This was the primary cause of sequencing errors.

In two-wavelength, two-beam excitation, base calling was based upon differences in fluorescence spectra as well as in absorption spectra. It also provided better S/N for the 2 rhodamine labels (FAM and JOE). DNA fragments were excited twice as they passed through the two detection windows. However, scattered 514-nm light introduced extra background at the 488-nm channel where the RE filter was used because the RE filter did not block 514-nm light. Careful alignment and proper setup was necessary in order to minimize the interference. It was necessary to physically isolate the two channels by placing a shield between them. The physical isolation was especially important when the capillary array was immersed in refractive-index matching liquid because Rayleigh and Raman scattering is much stronger in liquid than in air. Scattered laser light not only distributed around the outside of the capillary, but also propagated within the capillary by internal reflection due to the differences of refractive index among the matrix, the capillary wall and air. It was found to be beneficial to leave several millimeters of polyimide coating between the two detection windows. The coating absorbed scattered laser light that propagated from one detection channel along the capillary to the other detection channel.

All the miscalled bases in the two-wavelength, two-beam excitation mode had features where the adjacent peaks were not resolved and were thus assigned inaccurate peak heights or missed entirely by the standard chromatographic software. However, visual inspection of the raw data revealed shoulders or unusually broad peaks corresponding to 1.0>R>0.5 in the separation.

Two aspects of this base calling scheme could be improved. Matching of the migration times by normalization to the relative distance traveled depends on having uniform velocities (temperature, matrix homogeneity) along the entire capillary. The two laser beams also produced scattered light that can interfere with each other (514 nm laser line transmitted by the Raman-edge filter) and decrease the S/N. So, the 488 nm laser line was used alone. All four standard dye labels absorb at 488 nm, although not all four do so equally efficiently. At first, the two-window approach was retained but the output from one laser was split to favor the red channel (passing through the 610 nm filter) in order to compensate for the lower absorption of those 2 dye labels. The results were essentially the same as those obtained by using 2 wavelengths in excitation. The advantages were lower stray light (no 514 nm present) and simplicity in using a single-line laser. Matching the migration times from the two channels was still necessary, however.

A better solution was to use only one laser and one excitation window. Superficially, this seems inadequate for base calling using the four dye labels of the Sanger reaction. FIG. 9 presents an elegant solution that splits the image into two emission channels with maximum light throughput. There was then no need to convert the time scales of the two electropherograms obtained at the two spectral channels in order to match the peaks of a DNA fragment at the two spectral channels. This simplified data analysis and improved the accuracy of nucleotide identification. When a CID detector was used and exposure-time gradient was applied (see Example IV), the one-beam excitation scheme also eliminated the chances of peak mismatch caused by nonuniform distribution of temperature or voltage along a capillary. This is because peak matching in the two-beam excitation scheme relies on the assumption that a DNA fragment migrates along a capillary with constant velocity. More important, the one-beam excitation scheme provided the freedom of operating the system at any gradient mode necessary to enhance resolution or detectability, such as by using exposure-time gradient, temperature gradient and voltage gradient, or combinations of these gradient methods.

By using the one-wavelength, one-beam excitation mode, within 330 bp, base calling accuracy was 99.3%, i.e., only two errors occurred. One G was missed among the four Gs between 51 bp and 54 bp. The other error occurred at 317 bp where A was miscalled as T. For fragments longer than 250 bp, extra care is needed because resolution and S/N is reduced. When partially resolved peaks are split by software, the position of splitting is critical. Some of the peaks are resolved in one spectral channel but unresolved in the other. When base calling proceeded to 353 bp, accuracy decreased to 97.1%. Although S/N was still sufficient for integration beyond 353 bp, it was not practical to call bases further because that is roughly the limit of confidence for the Taq-catalyzed Sanger reaction.

Ratiograms. The base calling procedure based on the one excitation laser/two emission wavelength data described above was subsequently further improved. Instead of relying on software to identify peaks and determine peak heights at each channel, a "ratiogram" was generated, which is the ratio of signals from the two channels calculated point by point at each data interval. Similar ratiograms have been used in liquid chromatography to determine peak purity when using diode array detectors or rapid-scan multiwavelength detectors. Software is in fact included in several commercial instruments. The idea is that the ratio of intensities at two independent wavelengths is independent of concentration (which varies across the peak), and can be used to sort out the unresolved components in the merged peaks. As long as the overall S/N is good, even peaks with resolution R<0.5 can in many cases be identified by noting the ratios at the leading edge and at the falling edge of the merged peak. The usual electropherogram is still needed to determine where the ratios are meaningful and where the signals are at the noise level and are therefore meaningless. However, peaks need not be resolved by the chromatography software and errors in determining peak heights (when unresolved) are avoided.

FIG. 12 shows a ratiogram plotted on top of the electropherogram obtained through the RE filter, which records all peaks regardless of the label. The horizontal lines are artifacts to prevent division errors when S/N is too low to determine a meaningful ratio. The raw signal from the 488 nm excitation/Raman edge filter is plotted below (light line). The called bases are typed on the abscissa. The accuracy was 99% through 340 bases. Note the feature at marker 800. It was clearly broader than the surrounding features, indicating an overlapping set of fragments. The ratiogram clearly shows that the leading edge was "A" and the trailing edge was "G" in character. So, even though this feature led to base calling error in the peak-height scheme using chromatography software, it was correctly called in this novel scheme. Other noteworthy portions are the regions around markers 600 and 1180, where partially resolved features were correctly called in a similar fashion.

Defining the baseline for the peaks is important for accuracy. All 3 errors (<340 bp) occurred in one stretch around 260 bp where the simple baseline-selection algorithm resulted in negative values for some of the fluorescence intensities in the 488-nm cutoff channel. Similarly, there was a series of errors around 350 bp where there was insufficient background subtraction. Refinement in the software should allow accurate base calling for DNA fragments in excess of 400 bp in length, since the peak resolution there is still better than 0.5.

The complete disclosures of all patents, patent documents, and publications are incorporated herein by reference, as if individually incorporated. The foregoing detailed descriptions and examples have been given for clarity of understanding only. It will be appreciated by those skilled in the art that various modifications can be made to the above described embodiments of the invention without departing from the essential nature thereof. The invention is intended to encompass all such modifications within the scope of the appended claims.

What is claimed is:

1. A capillary containing a polymer matrix comprising about 0.5%–3% poly(ethyleneoxide) having $M_n$ of about 300,000–8,000,000, wherein the capillary comprises an uncoated internal wall having protonated silanol groups.

2. The capillary of claim 1 wherein the polymer matrix is a binary polymer matrix comprising about 1%–2% poly(ethyleneoxide) having $M_n$ of about 600,000 and about 1%–2% poly(ethyleneoxide) having $M_n$ of about 8,000,000.

3. The capillary of claim 1 wherein the protonated silanol groups are formed by treating the uncoated internal capillary wall with acid prior to placement of the polymer matrix in the capillary.

4. The capillary of claim 1 wherein the polymer matrix is a binary polymer matrix.

5. The capillary of claim 4 wherein the binary polymer matrix comprises a poly(ethyleneoxide) having $M_n$ of about 600,000 and a poly(ethyleneoxide) having $M_n$ of about 8,000,000.

6. The capillary of claim 1 wherein the polymer matrix is a mixed polymer matrix comprising about 0.6%–0.7% each poly(ethyleneoxide) having $M_n$ of about 300,000, 600,000, 1,000,000, 2,000,000, 5,000,000 and 8,000,000.

7. A capillary containing a binary polymer matrix comprising about 1%–2% poly(ethyleneoxide) having $M_n$ of about 600,000 and about 1%–2% poly(ethyleneoxide) having $M_n$ of about 8,000,000.

8. The capillary of claim 7 wherein the capillary comprises an uncoated internal wall prior to placement of the polymer matrix therein.

9. The capillary of claim 8 wherein the uncoated internal capillary wall comprises protonated silanol groups.

10. The capillary of claim 9 wherein the protonated silanol groups are formed by treating the uncoated internal capillary wall with acid prior to placement of the polymer matrix in the capillary.

11. A capillary containing a polymer matrix comprising two or more different polymers having $M_n$ of about 300,000–8,000,000, wherein the capillary comprises an uncoated internal wall having protonated silanol groups.

12. The capillary of claim 11 wherein each of the polymers is present in a concentration of about 0.5–2.0%.

13. The capillary of claim 12 wherein the polymer matrix comprises a poly(ethyleneoxide) having $M_n$ of about 600,000 and a poly(ethyleneoxide) having $M_n$ of about 8,000,000.

14. The capillary of claim 11 wherein the protonated silanol groups are formed by treating the uncoated internal capillary wall with acid prior to placement of the polymer matrix in the capillary.

15. A capillary containing a mixed polymer matrix comprising about 0.6%–0.7% each poly(ethyleneoxide) having $M_n$ of about 300,000, 600,000, 1,000,000, 2,000,000, 5,000,000, and 8,000,000.

16. The capillary of claim 15 wherein the capillary comprises an uncoated internal wall prior to placing the polymer matrix therein.

17. The capillary of claim 16 wherein the uncoated internal capillary wall comprises protonated silanol groups.

18. The capillary of claim 17 wherein the protonated silanol groups are formed by treating the uncoated internal capillary wall with acid prior to placement of the polymer matrix in the capillary.

19. A capillary containing a polymer matrix comprising poly(ethyleneoxide) having $M_n$ of about 300,000–8,000,000, wherein the capillary comprises an uncoated internal wall having protonated silanol groups.

20. A capillary containing a binary polymer matrix comprising poly(ethyleneoxide) having $M_n$ of about 600,000 and poly(ethyleneoxide) having $M_n$ of about 8,000,000.

* * * * *

UNITED STATES PATENT AND TRADEMARK OFFICE
CERTIFICATE OF CORRECTION

PATENT NO.: 5,695,626
DATED: December 9, 1997
INVENTOR(S): Edward S. Yeung et al.

It is certified that error appears in the above-identified patent and that said Letters Patent is hereby corrected as shown below:

On the title page,

Item [75], delete "Huan-Tsang Chang" and insert --Huan-Tsung Chang--.

Signed and Sealed this

Eighteenth Day of May, 1999

Attest:

Q. TODD DICKINSON

*Attesting Officer*   *Acting Commissioner of Patents and Trademarks*